US012566501B2

(12) United States Patent
Su et al.

(10) Patent No.: US 12,566,501 B2
(45) Date of Patent: Mar. 3, 2026

(54) MOTION MONITORING METHODS AND SYSTEMS

(71) Applicant: SHENZHEN SHOKZ CO., LTD., Guangdong (CN)

(72) Inventors: Lei Su, Shenzhen (CN); Xin Zhou, Shenzhen (CN); Meiqi Li, Shenzhen (CN); Fengyun Liao, Shenzhen (CN)

(73) Assignee: SHENZHEN SHOKZ CO., LTD., Shenzhen (CN)

( * ) Notice: Subject to any disclaimer, the term of this patent is extended or adjusted under 35 U.S.C. 154(b) by 314 days.

(21) Appl. No.: 18/183,923

(22) Filed: Mar. 14, 2023

(65) Prior Publication Data

US 2023/0233103 A1     Jul. 27, 2023

Related U.S. Application Data

(63) Continuation of application No. PCT/CN2021/081931, filed on Mar. 19, 2021.

(51) Int. Cl.
G06F 3/01          (2006.01)
A61B 5/00          (2006.01)
(Continued)

(52) U.S. Cl.
CPC ............ G06F 3/015 (2013.01); A61B 5/1116 (2013.01); A61B 5/296 (2021.01); A61B 5/397 (2021.01);
(Continued)

(58) Field of Classification Search
CPC ...... G06F 3/015; G06F 18/2415; G06F 1/163; G06F 1/1684; G06F 2218/08; G06F 3/011; G06F 3/017; G06F 17/18; A61B 5/1116; A61B 5/296; A61B 5/397; A61B 5/7225; A61B 5/14551; A61B 5/0816; A61B 5/1121; A61B 5/1123; A61B 5/113; A61B 5/7253; A61B 5/7278; A61B 5/6803;
(Continued)

(56) References Cited

U.S. PATENT DOCUMENTS

2004/0117212 A1     6/2004  Kong et al.
2009/0012381 A1     1/2009  Kuramori et al.
(Continued)

FOREIGN PATENT DOCUMENTS

CN     104706359 A     6/2015
CN     104720821 A     6/2015
(Continued)

OTHER PUBLICATIONS

International Search Report in PCT/CN2021/081931 mailed on Dec. 22, 2021, 8 pages.
(Continued)

*Primary Examiner* — Jeffrey G. Hoekstra
(74) *Attorney, Agent, or Firm* — METIS IP LLC

(57)          ABSTRACT

A motion monitoring method (500) is provided, which includes: obtaining a movement signal of a user during motion, wherein the movement signal includes at least an electromyographic signal or an attitude signal (510); and monitoring a movement of the user during motion based at least on feature information corresponding to the electromyographic signal or the feature information corresponding to the attitude signal (520).

20 Claims, 20 Drawing Sheets

(51) Int. Cl.

| | | |
|---|---|---|
| *A61B 5/11* | (2006.01) | |
| *A61B 5/296* | (2021.01) | |
| *A61B 5/397* | (2021.01) | |
| *G06F 18/2415* | (2023.01) | |
| *G16H 40/67* | (2018.01) | |
| *G16H 50/20* | (2018.01) | |

(52) U.S. Cl.
CPC ........ *A61B 5/7225* (2013.01); *G06F 18/2415* (2023.01); *G16H 40/67* (2018.01); *G16H 50/20* (2018.01)

(58) Field of Classification Search
CPC ..... A61B 5/7257; A61B 5/726; A61B 5/7405; A61B 5/7455; A61B 2562/0219; A61B 5/0022; A61B 2505/09; A61B 5/6804; A61B 5/7207; A61B 5/7246; A61B 5/725; A61B 5/7275; A61B 5/318; A61B 5/02055; A61B 5/02438; A61B 5/08; A61B 5/14542; A61B 5/24; A61B 5/389; A61B 5/1118; A61B 5/6802; A61B 5/746; A61B 5/11; A61B 5/6801; A61B 5/0205; A61B 5/1455; A61B 2560/0223; G16H 40/67; G16H 50/20; A63B 71/06
See application file for complete search history.

(56) References Cited

U.S. PATENT DOCUMENTS

| | | |
|---|---|---|
| 2009/0319459 A1 | 12/2009 | Breazeal et al. |
| 2011/0118621 A1 | 5/2011 | Chu |
| 2013/0116580 A1 | 5/2013 | Liu et al. |
| 2013/0173764 A1 | 7/2013 | Kami |
| 2014/0135960 A1 | 5/2014 | Choi |
| 2014/0207017 A1 | 7/2014 | Gilmore et al. |
| 2015/0045699 A1 | 2/2015 | Mokaya et al. |
| 2015/0106025 A1 | 4/2015 | Keller et al. |
| 2015/0272482 A1 | 10/2015 | Houmanfar et al. |
| 2017/0135640 A1 | 5/2017 | Gunasekar et al. |
| 2017/0224985 A1* | 8/2017 | Debur ................. A61N 1/0452 |
| 2017/0231521 A1 | 8/2017 | Axelrod |
| 2018/0024635 A1 | 1/2018 | Kaifosh et al. |
| 2018/0047157 A1 | 2/2018 | Sinha et al. |
| 2018/0121713 A1 | 5/2018 | Guo et al. |
| 2019/0046067 A1 | 2/2019 | Du et al. |
| 2019/0343459 A1 | 11/2019 | Korzinov et al. |
| 2020/0054931 A1 | 2/2020 | Martin et al. |
| 2020/0155018 A1 | 5/2020 | Igami |
| 2020/0302236 A1 | 9/2020 | Gao et al. |
| 2020/0310541 A1 | 10/2020 | Reisman et al. |

FOREIGN PATENT DOCUMENTS

| | | |
|---|---|---|
| CN | 105635669 A | 6/2016 |
| CN | 105705092 A | 6/2016 |
| CN | 105796112 A | 7/2016 |
| CN | 105797350 A | 7/2016 |
| CN | 105997064 A | 10/2016 |
| CN | 106073793 A | 11/2016 |
| CN | 107115114 A | 9/2017 |
| CN | 107320095 A | 11/2017 |
| CN | 107349594 A | 11/2017 |
| CN | 107361773 A | 11/2017 |
| CN | 207071088 U | 3/2018 |
| CN | 108143409 A | 6/2018 |
| CN | 108209910 A | 6/2018 |
| CN | 108211308 A | 6/2018 |
| CN | 108211309 A | 6/2018 |
| CN | 108211310 A | 6/2018 |
| CN | 108566520 A | 9/2018 |
| CN | 108983954 A | 12/2018 |
| CN | 109068081 A | 12/2018 |
| CN | 109191588 A | 1/2019 |
| CN | 109330609 A | 2/2019 |
| CN | 110109532 A | 8/2019 |
| CN | 110327048 A | 10/2019 |
| CN | 110443309 A | 11/2019 |
| CN | 110472611 A | 11/2019 |
| CN | 110478883 A | 11/2019 |
| CN | 110569775 A | 12/2019 |
| CN | 110609621 A | 12/2019 |
| CN | 110638444 A | 1/2020 |
| CN | 111028317 A | 4/2020 |
| CN | 111317446 A | 6/2020 |
| CN | 111803061 A | 10/2020 |
| CN | 111938656 A | 11/2020 |
| CN | 112214109 A | 1/2021 |
| CN | 112472042 A | 3/2021 |
| JP | 2003339908 A | 12/2003 |
| JP | 2010246636 A | 11/2010 |
| JP | 2011103914 A | 6/2011 |
| JP | 2012024521 A | 2/2012 |
| JP | 3181442 U | 2/2013 |
| JP | 2014002655 A | 1/2014 |
| JP | 2016150119 A | 8/2016 |
| JP | 2017143911 A | 8/2017 |
| JP | 2018083014 A | 5/2018 |
| JP | 2019030520 A | 2/2019 |
| JP | 2020103653 A | 7/2020 |
| JP | 2020155961 A | 9/2020 |
| WO | 2018214522 A1 | 11/2018 |

OTHER PUBLICATIONS

João Lopes et al., Hand/arm gesture segmentation by motion using IMU and EMG sensing, 27th International Conference on Flexible Automation and Intelligent Manufacturing, 11: 107-113, 2017.
The Extended European Search Report in European Application No. 21930919.2 mailed on Jan. 3, 2024, 10 pages.
Notice of Reasons for Rejection in Japanese Application No. 2023528497 mailed on May 7, 2024, 12 pages.
The Communication Pursuant to Article 94(3) EPC in European Application No. 21930919.2 mailed on Sep. 11, 2025, 6 pages.
First Office Action in Brazilian Application No. BR1120230067634 mailed on Oct. 2, 2025, 8 pages.
First Office Action in Chinese Application No. 202180070833.3 mailed on Jan. 22, 2026, 17 pages.

* cited by examiner

100

<u>130</u>

400

Figure 5:
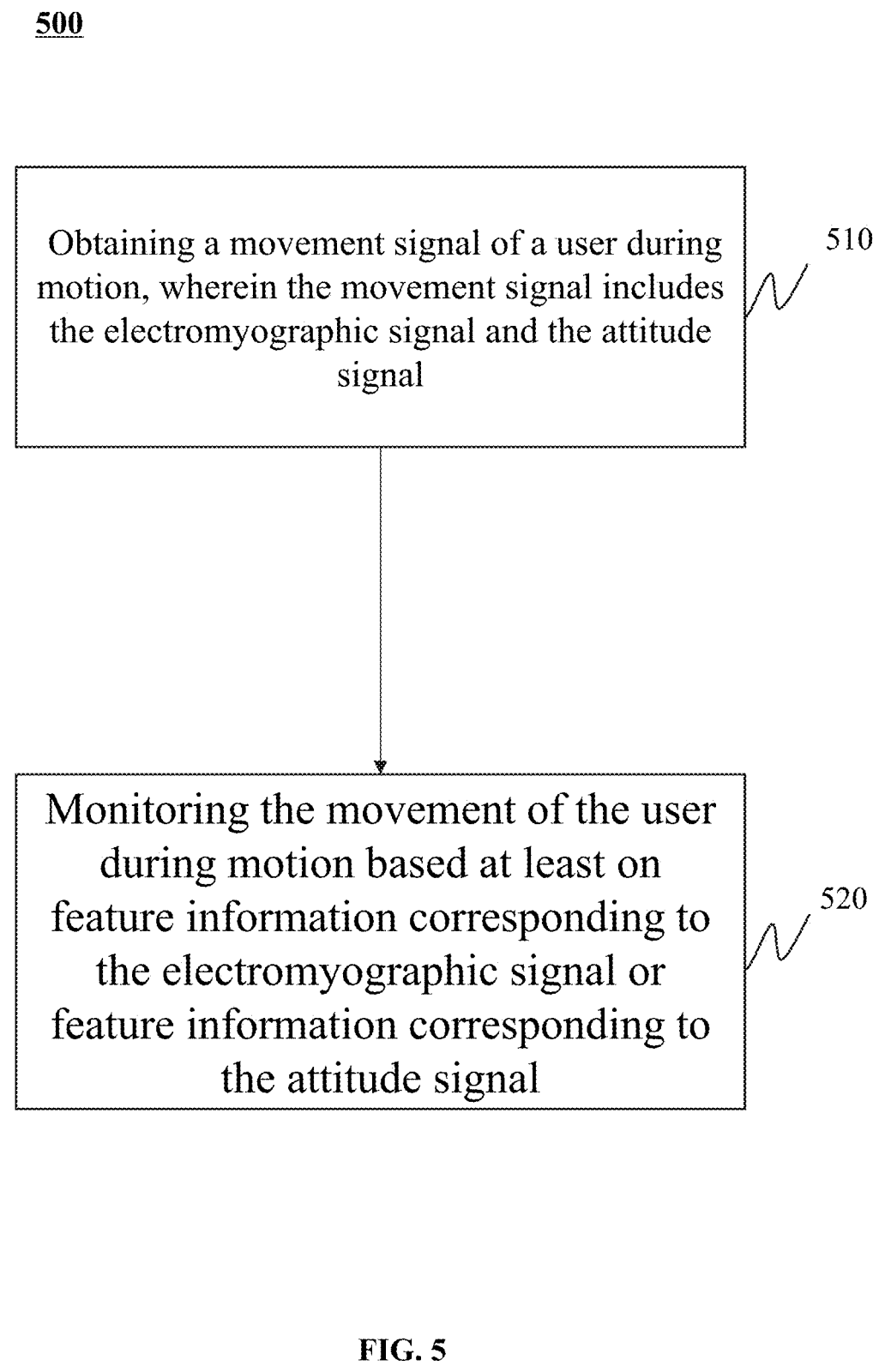

500

Obtaining a movement signal of a user during motion, wherein the movement signal includes the electromyographic signal and the attitude signal    510

Monitoring the movement of the user during motion based at least on feature information corresponding to the electromyographic signal or feature information corresponding to the attitude signal    520

Figure 6:
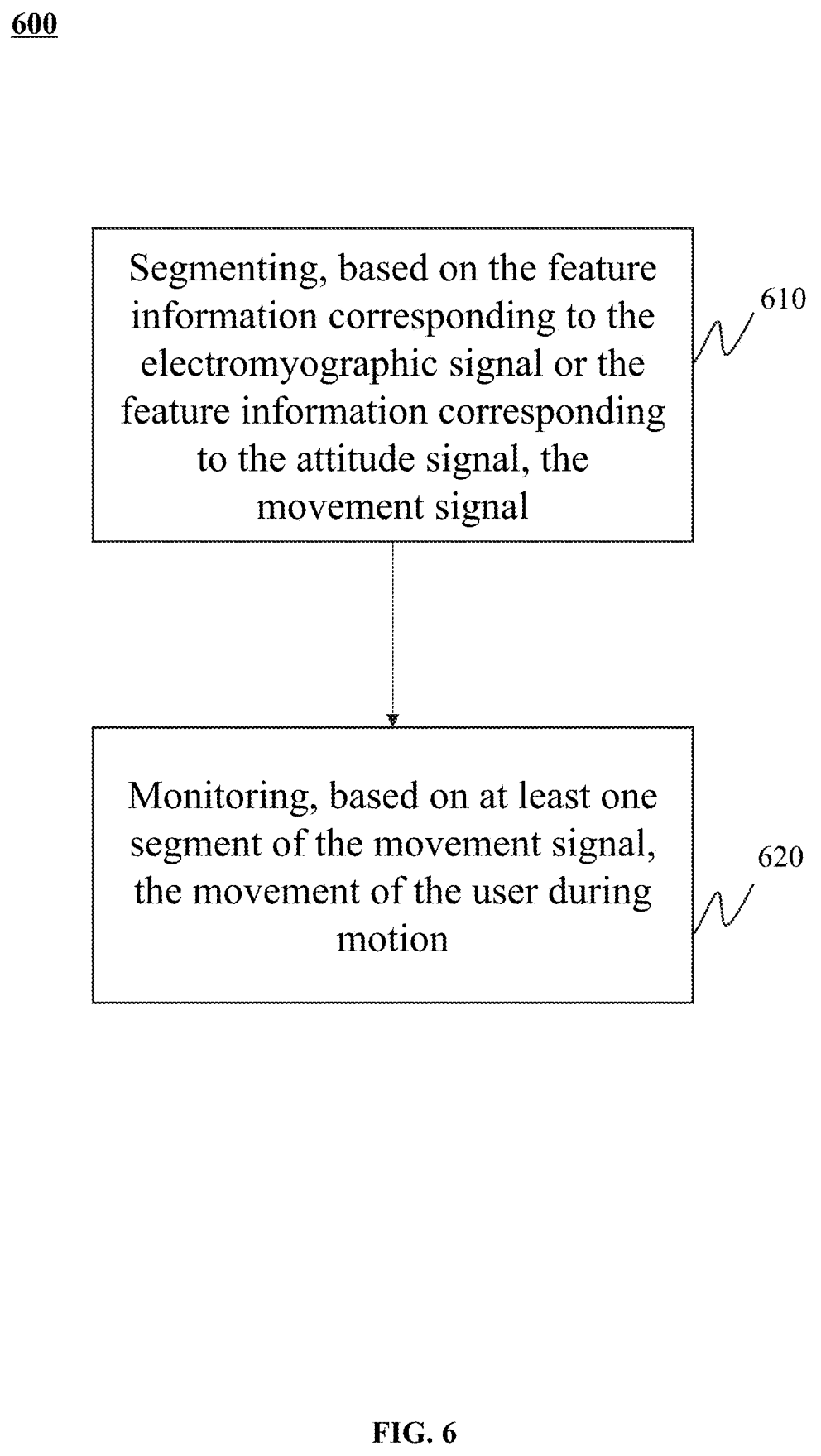

Segmenting, based on the feature
information corresponding to the
electromyographic signal or the
feature information corresponding
to the attitude signal, the
movement signal

610

Monitoring, based on at least one
segment of the movement signal,
the movement of the user during
motion

Determining, based on a time domain window of the electromyographic signal or the attitude signal, at least one target feature point from within the time domain window according to a preset condition    710

Segmenting, based on the at least one target feature point, the movement signal    720

Figure 9:
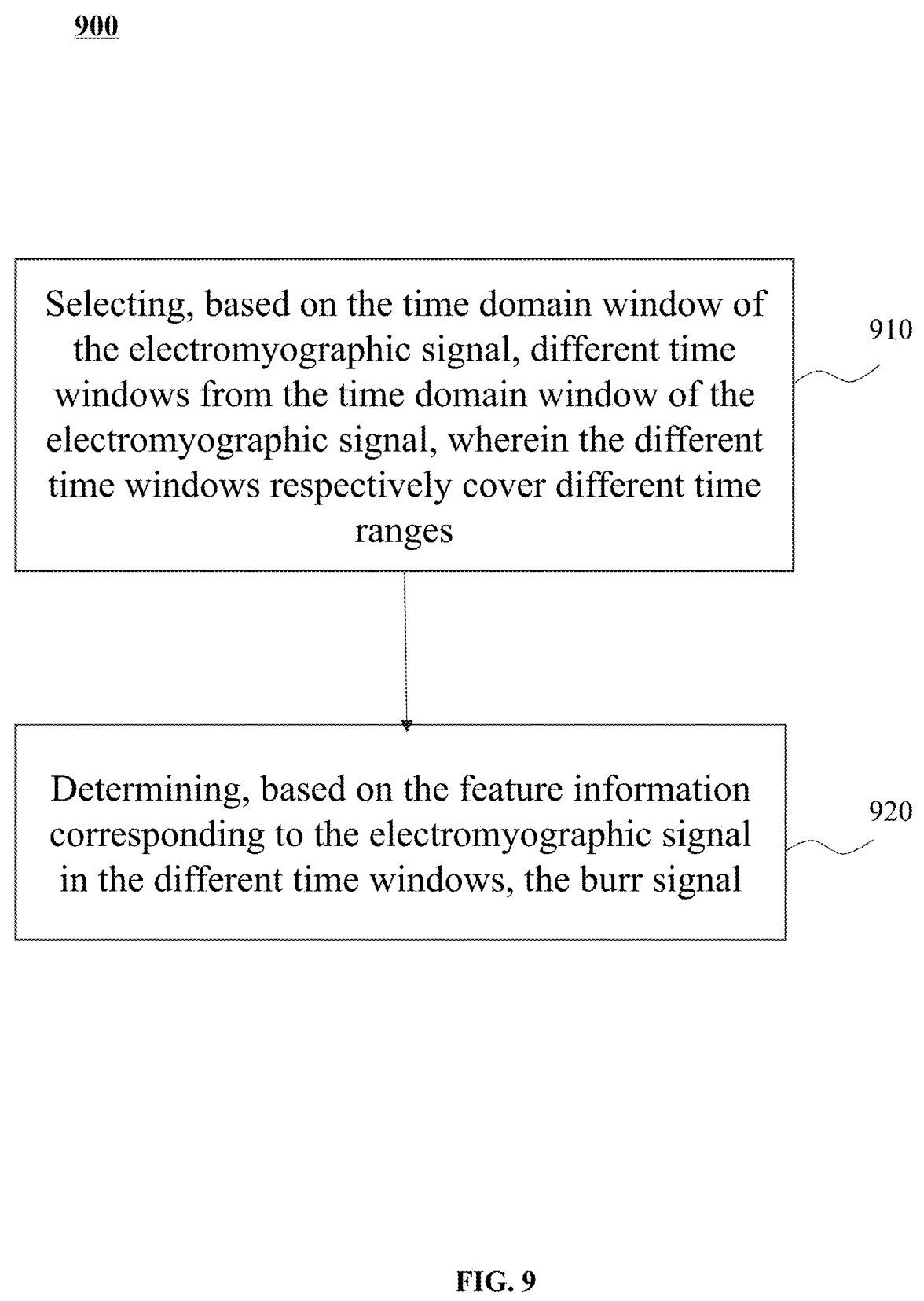

Selecting, based on the time domain window of the electromyographic signal, different time windows from the time domain window of the electromyographic signal, wherein the different time windows respectively cover different time ranges    910

Determining, based on the feature information corresponding to the electromyographic signal in the different time windows, the burr signal    920

Figure 11:
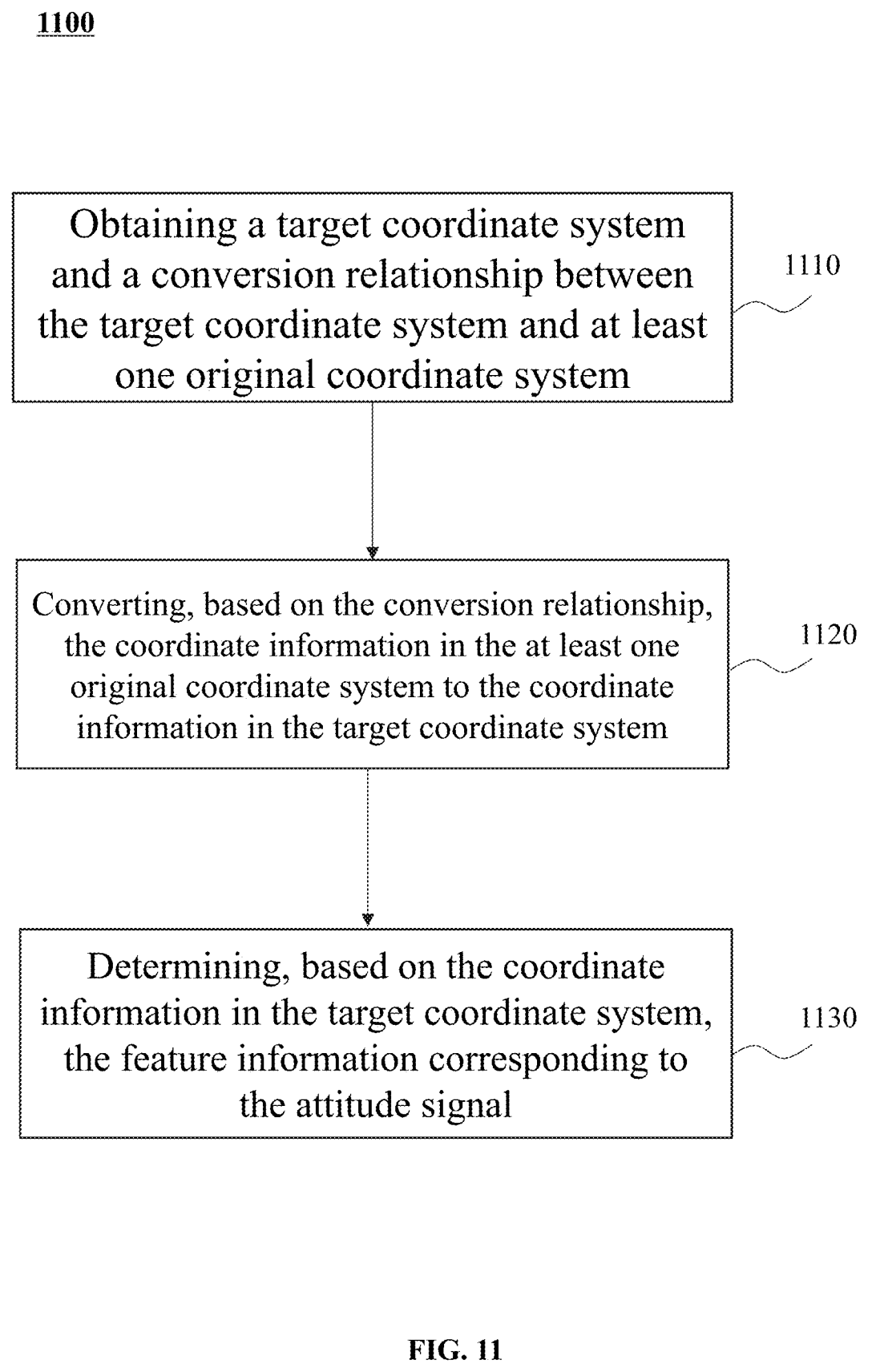

Obtaining a target coordinate system and a conversion relationship between the target coordinate system and at least one original coordinate system          1110

Converting, based on the conversion relationship, the coordinate information in the at least one original coordinate system to the coordinate information in the target coordinate system          1120

Determining, based on the coordinate information in the target coordinate system, the feature information corresponding to the attitude signal          1130

Figure 12:
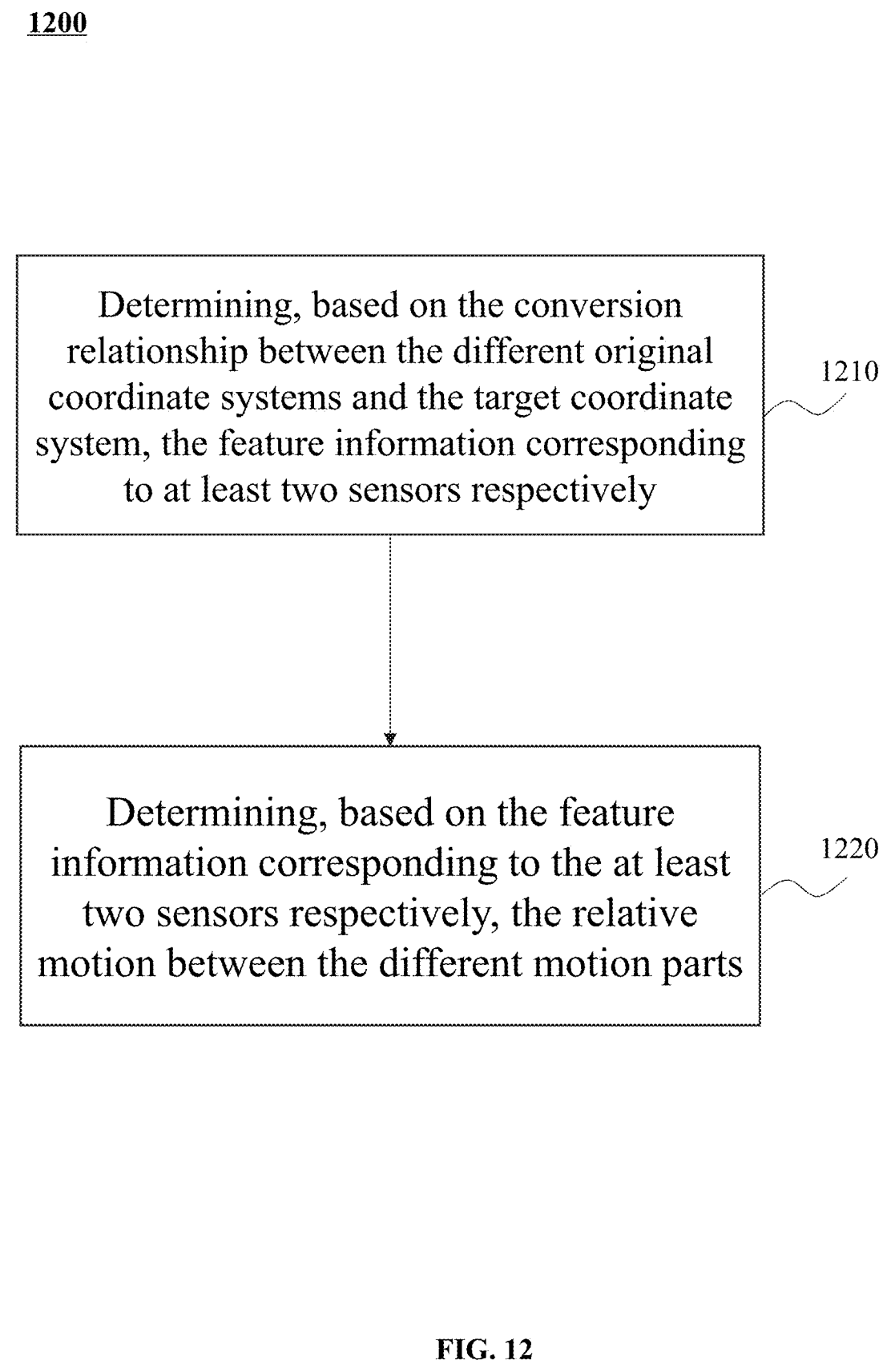

Determining, based on the conversion relationship between the different original coordinate systems and the target coordinate system, the feature information corresponding to at least two sensors respectively          1210

Determining, based on the feature information corresponding to the at least two sensors respectively, the relative motion between the different motion parts          1220

Figure 14:
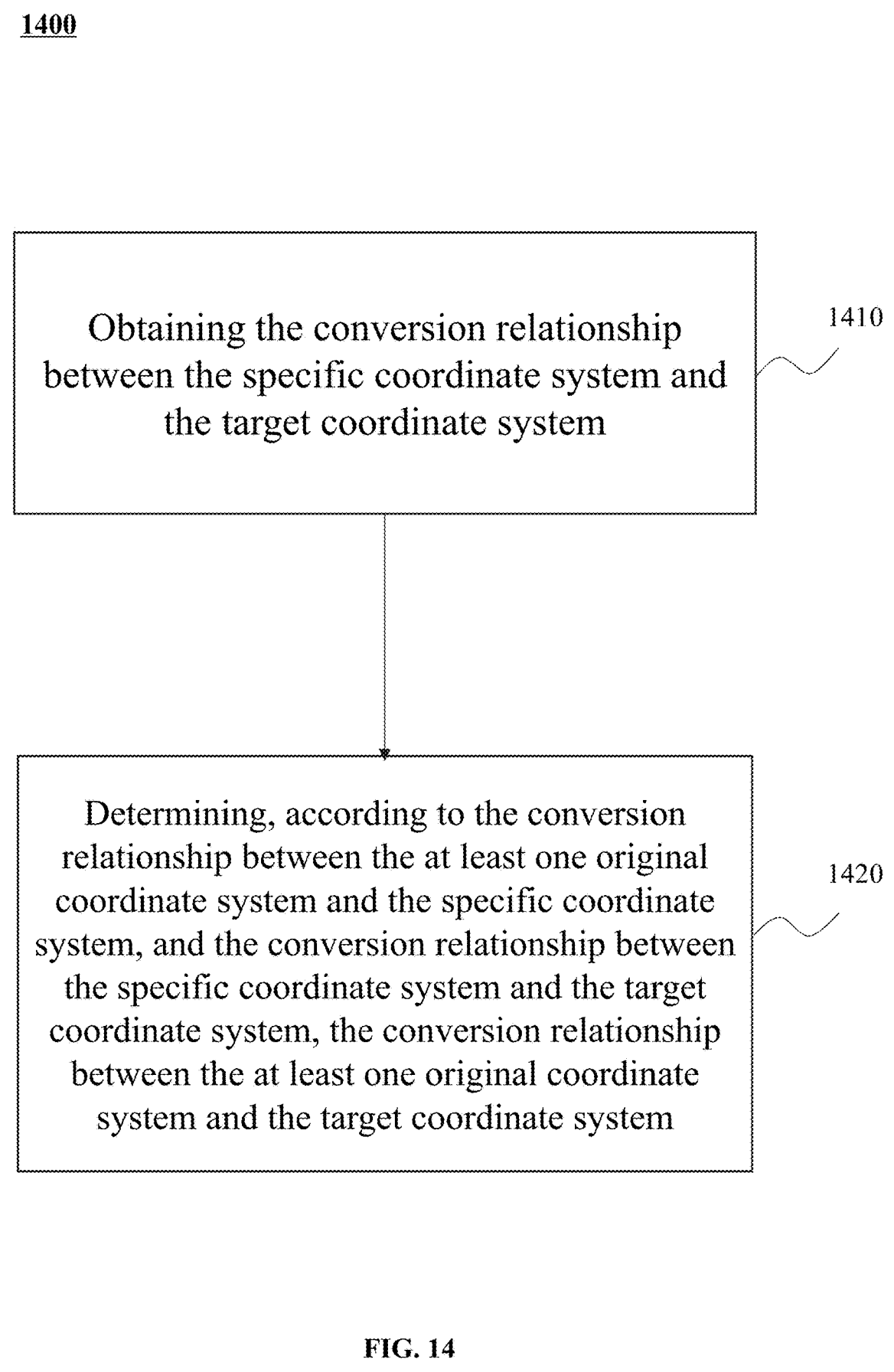

Obtaining the conversion relationship between the specific coordinate system and the target coordinate system          1410

Determining, according to the conversion relationship between the at least one original coordinate system and the specific coordinate system, and the conversion relationship between the specific coordinate system and the target coordinate system, the conversion relationship between the at least one original coordinate system and the target coordinate system          1420

Figure 19:
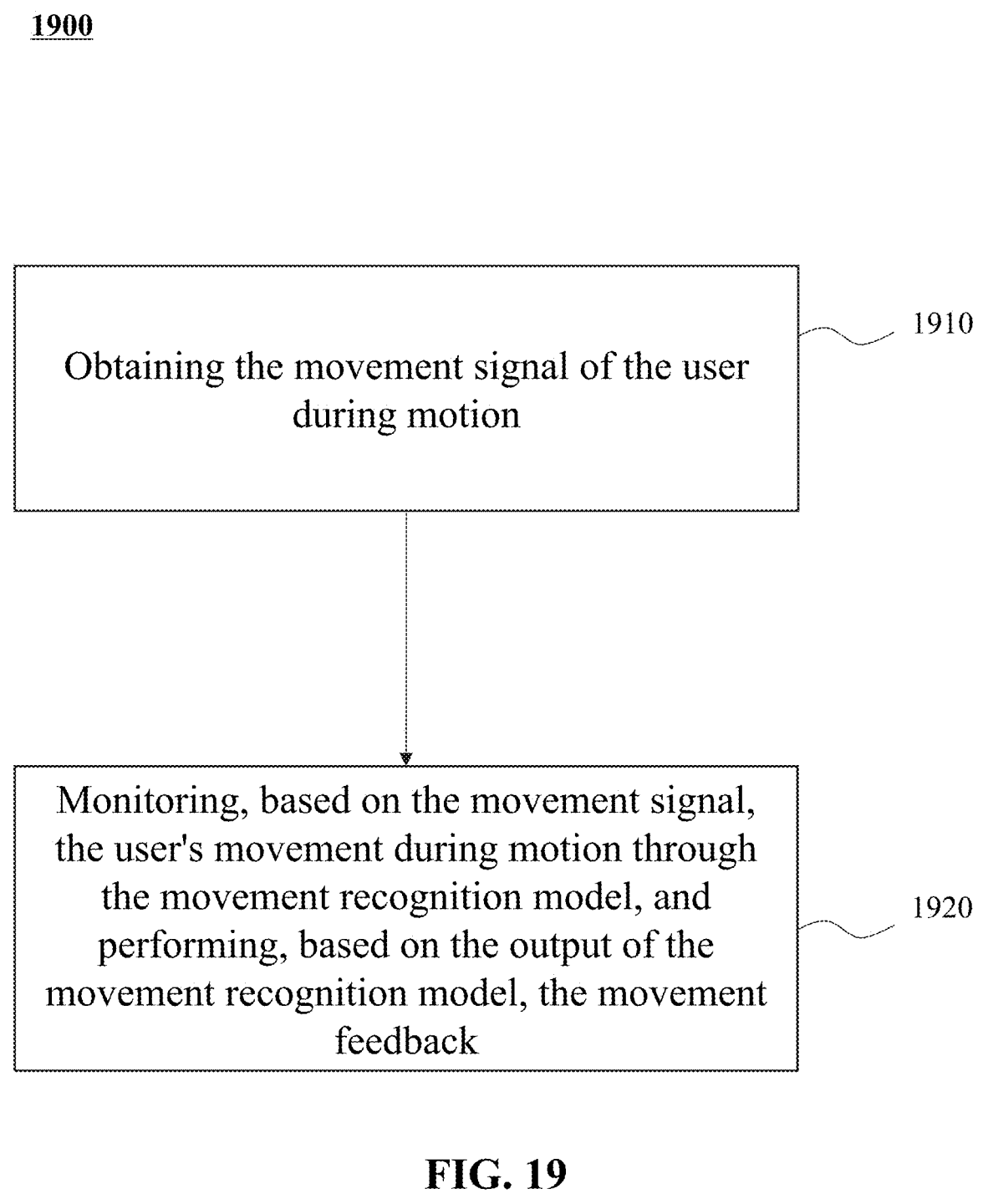

Obtaining the movement signal of the user during motion     1910

Monitoring, based on the movement signal, the user's movement during motion through the movement recognition model, and performing, based on the output of the movement recognition model, the movement feedback     1920

MOTION MONITORING METHODS AND SYSTEMS

CROSS REFERENCE TO RELATED APPLICATIONS

This application is a Continuation of International Patent Application No. PCT/CN2021/081931, filed on Mar. 19, 2021, the entire contents of each of which are hereby incorporated by references.

TECHNOLOGY FIELD

The present disclosure relates to a technical field of wearable devices, and in particular, to a motion monitoring method and system.

BACKGROUND

With people concerned about scientific exercise and physical health, motion monitoring devices are developing tremendously. At present, the motion monitoring devices mainly monitor some of the physiological parameter information (e.g., heart rate, body temperature, step frequency, blood oxygen, etc.) of a user during motion, but cannot accurately monitor user's movement and provide feedback on the movement. In practical scenarios, a process of monitoring and feeding the users' movement back often requires the participation of live professionals. For example, the user in the fitness scenario can only correct their movement under the guidance of a fitness instructor.

Therefore, it is desirable to provide a motion monitoring device that can guide a person's motion and thereby helping the user achieve more scientifically exact exercises.

SUMMARY

According to the embodiments of the present disclosure, a motion monitoring method is provided, including: obtaining a movement signal of a user during motion, the movement signal including at least an electromyographic signal or an attitude signal; and monitoring, at least based on feature information corresponding to the electromyographic signal or feature information corresponding to the attitude signal, a movement of the user during motion.

In some embodiments, the monitoring, at least based on feature information corresponding to the electromyographic signal or feature information corresponding to the attitude signal, a movement of the user during motion: segmenting, based on the feature information corresponding to the electromyographic signal or the feature information corresponding to the attitude signal, the movement signal; and monitoring, based on at least one segment of the movement signal, the movement of the user during motion.

In some embodiments, the feature information corresponding to the electromyographic signal includes at least frequency information or amplitude information, and the feature information corresponding to the attitude signal includes at least one of an angular velocity direction, an angular velocity value, an acceleration of an angular velocity, an angle, displacement information, and stress.

In some embodiments, the segmenting, based on the feature information corresponding to the electromyographic signal or the feature information corresponding to the attitude signal, the movement signal includes: determining, based on a time domain window of the electromyographic signal or the attitude signal, at least one target feature point from the time domain window according to a preset condition; and segmenting, based on the at least one target feature point, the movement signal.

In some embodiments, the at least one target feature point includes one of a movement start point, a movement middle point, and a movement end point.

In some embodiments, the preset condition includes a change in the angular velocity direction corresponding to the attitude signal, the angular velocity corresponding to the attitude signal being greater than or equal to an angular velocity threshold, a changed value of the angular velocity value corresponding to the attitude signal being an extreme value, the angle corresponding to the attitude signal reaching an angular threshold, and the amplitude information corresponding to the electromyographic signal being greater than or equal to one or more electromyographic thresholds.

In some embodiments, the preset condition further includes the acceleration of the angular velocity corresponding to the attitude signal being continuously greater than or equal to an acceleration threshold of the angular velocity for a first specific time range.

In some embodiments, the preset condition further includes an amplitude corresponding to the electromyographic signal being continuously greater than the one or more electromyographic thresholds for a second specific time range.

In some embodiments, the monitoring, at least based on feature information corresponding to the electromyographic signal or feature information corresponding to an attitude signal, a movement of the user during motion includes: pre-processing the electromyographic signal in a frequency domain or a time domain; obtaining, based on the pre-processed electromyographic signal, the feature information corresponding to the electromyographic signal; and monitoring, according to the feature information corresponding to the electromyographic signal or the feature information corresponding to the attitude signal, the movement of the user during motion.

In some embodiments, the pre-processing of the electromyographic signal in a frequency domain or a time domain includes: filtering the electromyographic signal to select components of the electromyographic signal in a specific frequency range in the frequency domain.

In some embodiments, the pre-processing of the electromyographic signal in a frequency domain or a time domain includes: performing a signal correction process on the electromyographic signal in the time domain.

In some embodiments, the performing a signal correction processing on the electromyographic signal in the time domain includes: determining a singularity in the electromyographic signal, wherein the singularity corresponds to an abrupt signal of the electromyographic signal; and performing the signal correction processing on the singularity in the electromyographic signal.

In some embodiments, the performing the signal correction processing on the singularity in the electromyographic signal includes removing the singularity, or correcting the singularity according to a signal around the singularity.

In some embodiments, the singularity includes a burr signal, the determining the singularity in the electromyographic signal includes: selecting, based on the time domain window of the electromyographic signal, different time windows from the time domain window of the electromyographic signal, wherein the different time windows respectively cover different time ranges; and determining, based on the feature information corresponding to the electromyographic signal in the different time windows, the burr signal.

In some embodiments, the method further includes determining, based on the attitude signal, the feature information corresponding to the attitude signal, wherein the attitude signal includes coordinate information in at least one original coordinate system; determining, based on the attitude signal, the feature information corresponding to the attitude signal includes: obtaining a target coordinate system and a conversion relationship between the target coordinate system and the at least one original coordinate system; converting, based on the conversion relationship, the coordinate information in the at least one original coordinate system to coordinate information in the target coordinate system; and determining, based on the coordinate information in the target coordinate system, the feature information corresponding to the attitude signal.

In some embodiments, the attitude signal includes coordinate information generated by at least two sensors, the at least two sensors are located at different motion parts of the user and correspond to different original coordinate systems, the determining, based on the attitude signal, the feature information corresponding to the attitude signal includes: determining feature information corresponding to each of the at least two sensors based on the conversion relationship between different original coordinate systems and the target coordinate system; and determining, based on the feature information respectively corresponding to the at least two sensors, a relative motion between the motion parts of the user.

In some embodiments, the conversion relationship between the at least one original coordinate system and the target coordinate system is obtained by a calibration process, the calibration process includes: constructing a specific coordinate system, the specific coordinate system being related to an orientation of the user during the calibration process; obtaining first coordinate information of the at least one original coordinate system when the user is in a first pose; obtaining second coordinate information of the at least one original coordinate system when the user is in a second pose; and determining the conversion relationship between the at least one original coordinate system and the specific coordinate system according to the first coordinate information, the second coordinate information, and the specific coordinate system.

In some embodiments, the calibration process further includes: obtaining a conversion relationship between the specific coordinate system and the target coordinate system; and determining, according to the conversion relationship between the at least one original coordinate system and the specific coordinate system as well as the conversion relationship between the specific coordinate system and target coordinate system, the conversion relationship between the at least one original coordinate system and the target coordinate system.

In some embodiments, the target coordinate system changes as the user's orientation changes.

According to another aspect of the present disclosure, a method of training a movement recognition model is provided, including: obtaining sample information, the sample information including a movement signal of a user during motion, the movement signal including at least feature information corresponding to an electromyographic signal and feature information corresponding to an attitude signal; and training, based on the sample information, the movement recognition model.

According to another aspect of the present disclosure, a motion monitoring and feedback method is provided, including: obtaining a movement signal of a user during motion, wherein the movement signal includes at least an electromyographic signal and an attitude signal; and monitoring, based on feature information corresponding to the electromyographic signal and feature information corresponding to the attitude signal, a movement of a user by a movement recognition model, and providing, based on an output of the movement recognition model, a movement feedback.

In some embodiments, the movement recognition model includes a trained machine learning model or a preset model.

In some embodiments, the movement feedback includes at least one of sending a prompt message, stimulating a movement part of the user, and outputting a motion record of the user during motion.

BRIEF DESCRIPTION OF THE DRAWINGS

The present disclosure is further illustrated in terms of exemplary embodiments, and these exemplary embodiments are described in detail with reference to the drawings. These embodiments are not limiting. In these embodiments, the same number indicates the same structure, wherein:

FIG. 5 is a flowchart of an exemplary motion monitoring method according to some embodiments of the present disclosure;

FIG. 6 is a flowchart of an exemplary process for monitoring a movement of user motion according to some embodiments of the present disclosure;

FIG. 7 is a flowchart of an exemplary process for segmenting a movement signal according to some embodiments of the present disclosure;

FIG. 9 is a flowchart of an exemplary process for preprocessing an electromyographic signal according to some embodiments of the present disclosure;

FIG. 11 is a flowchart of an exemplary process for determining feature information corresponding to an attitude signal according to some embodiments of the present disclosure;

FIG. 12 is a flowchart of an exemplary process for determining relative motion between different motion parts of a user according to some embodiments of the present disclosure;

FIG. 14 is a flowchart of an exemplary process for determining a conversion relationship between an original coordinate system and a target coordinate system according to some embodiments of the present disclosure;

FIG. 19 is a flowchart illustrating an exemplary motion monitoring and feedback method according to some embodiments of the present disclosure.

DETAILED DESCRIPTION

Figure 1:
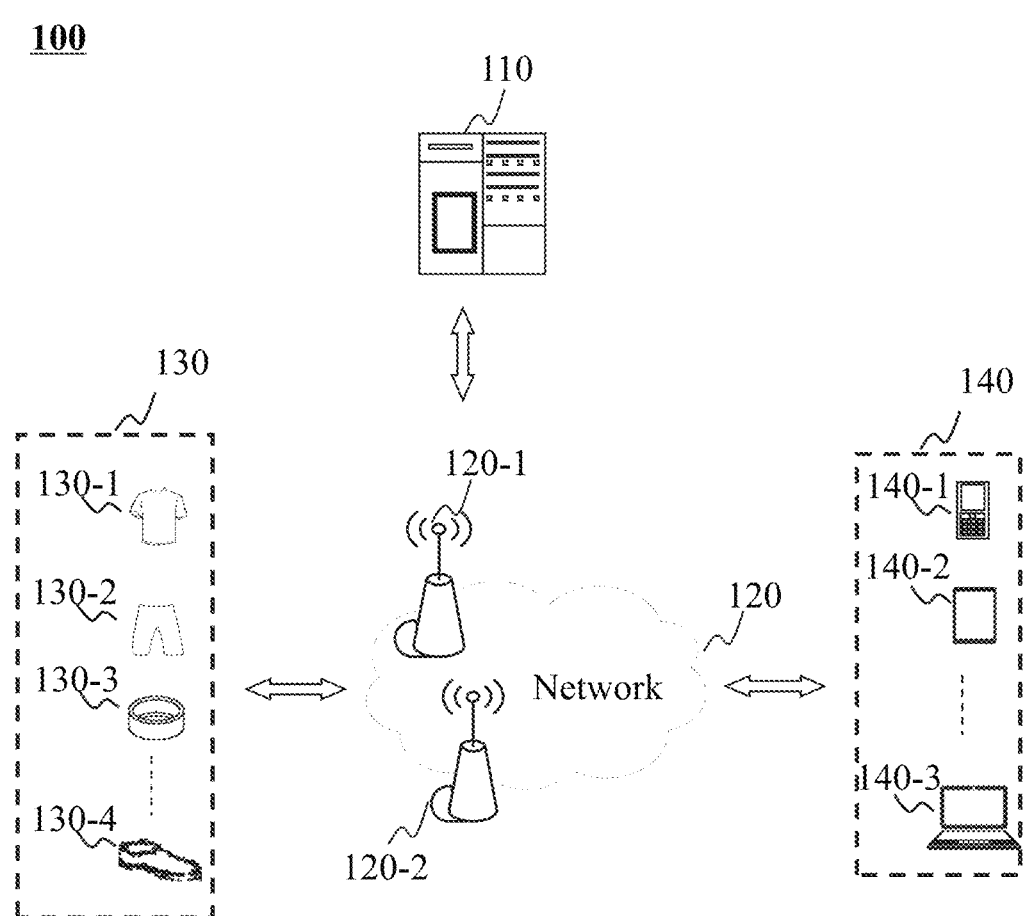
FIG. 1 is a schematic diagram illustrating an application scenario of a motion monitoring system according to some embodiments of the present disclosure.

To more clearly illustrate the technical solutions related to the embodiments of the present disclosure, a brief introduction of the drawings referred to the description of the embodiments is provided below. Obviously, the accompanying drawing in the following description is merely some examples or embodiments of the present disclosure, for those skilled in the art, the present disclosure may further be applied in other similar situations according to the drawings without any creative effort. Unless obviously obtained from the context or the context illustrates otherwise, the same numeral in the drawings refers to the same structure or operation.

It will be understood that the term "system," "device," "unit," and/or "module" used herein are one method to distinguish different components, elements, parts, sections or assemblies of different levels in ascending order. However, if other words may achieve the same purpose, the words may be replaced by other expressions.

As used in the disclosure and the appended claims, the singular forms "a," "an," and "the" include plural referents unless the content clearly dictates otherwise. Generally speaking, the terms "comprise," "comprises," and/or "comprising," "include," "includes," and/or "including," only imply that the clearly identified steps and elements are included, these steps and elements may not constitute an exclusive list, and the method or device may further include other steps or elements.

Flowcharts are used throughout the present disclosure to illustrate the operations performed by the system according to embodiments of the present disclosure. It should be understood that the preceding or following operations are not necessarily performed in precise order. Instead, the individual steps may be processed in reverse order or simultaneously. Other operations may be added to these processes or a step or steps of operations may be removed from these processes.

According to the present disclosure, a motion monitoring system is provided, which may obtain a movement signal of a user during motion. The movement signal includes at least an electromyographic signal, an attitude signal, an electro-cardio graphic signal, a respiratory rate signal, and the like. The motion monitoring system may monitor a movement of the user during motion based at least on feature information corresponding to the electromyographic signal or the feature information corresponding to an attitude signal. For example, the system may determine the type of movement of the user, the number of movement, the movement quality, movement time, or information of physiological parameters of the user when performing the movement through frequency information and amplitude information corresponding to the electromyographic signal, an angular velocity, an angular velocity direction and an angular velocity value of the angular velocity, an angle, displacement information, and stress, etc. corresponding to the attitude signal. In some embodiments, the motion monitoring system may further generate feedback to a user's fitness movement according to analysis results of the user's fitness movement to provide guidance to user's fitness. For example, when the user's fitness movement is not standard, the motion monitoring system can send a prompt message to the user (e.g., a voice prompt, a vibration prompt, current stimulation, etc.). The motion monitoring system may be applied to a wearable device (e.g., clothing, a wrist guard, a helmet), a medical testing device (e.g., an electromyography tester), a fitness device, etc. The motion monitoring system may accurately monitor and provide feedback on a user's movement by obtaining the movement signal of the user during motion without professional participation, which can improve the user's fitness efficiency and reduce a cost of the user fitness.

FIG. 1 is a schematic diagram illustrating an application scenario of a motion monitoring system according to some embodiments of the present disclosure. As shown in FIG. 1, the motion monitoring system 100 may include a processing device 110, a network 120, a wearable device 130, and a mobile terminal device 140. The motion monitoring system 100 may obtain a movement signal (e.g., an electromyographic signal, an attitude signal, an electro-cardio signal, a respiratory rate signal, etc.) representing a movement of user motion, and may monitor and provide feedback on the movement of the user during motion according to a user's movement signal.

For example, the motion monitoring system 100 may monitor and provide feedback on the movement of the user during fitness. When the user wears the wearable device 130 for fitness, the wearable device 130 may obtain the user's movement signal. The processing device 110 or a mobile terminal device may receive and analyze the user's movement signal to determine whether the user's fitness movement is standard, thereby monitoring the user's movement. Specifically, the monitoring of the user's movement may include determining a type of movement, a count of movement, quality of the movement, and timing of the movement, or information about the physiological parameters of the user at the time the movement is performed. Further, the motion monitoring system 100 may generate feedback on the user's fitness movement according to the analysis results of the user's fitness movement to provide guidance to the user.

Further, for example, the motion monitoring system 100 may monitor and provide feedback on the user's movement while running. For example, when the user wears the wearable device 130 for running exercise, the motion monitoring system 100 may monitor whether the user's running movement is standard and whether the running time meets a health standard. When a user's running time is too long or a running movement is incorrect, the fitness device may provide motion state to the user to prompt the user to adjust the running movement or the running time.

In some embodiments, the processing device 110 may be configured to process information and/or data related to the user's movement. For example, the processing device 110 may receive the movement signal of the user (e.g., an electromyographic signal, an attitude signal, an electro-cardio signal, a respiratory rate signal, etc.) and further extract the feature information corresponding to the movement signal (e.g., feature information corresponding to the electromyographic signal in the movement signal, the feature information corresponding to the attitude signal). In some embodiments, the processing device 110 may perform a specific signal processing, such as signal segmentation, signal pre-processing (e.g., signal correction processing, filtering processing, etc.), etc., on the electromyographic signal or the attitude signal obtained by the wearable device 130. In some embodiments, the processing device 110 may further determine whether the user movement is correct based on the user's movement signal. For example, the processing device 110 may determine whether the user movement is correct based on the feature information corresponding to the electromyographic signal (e.g., amplitude information, frequency information, etc.). For another example, the processing device 110 may determine whether the user movement is correct based on the feature information corresponding to the attitude signal (e.g., an angular velocity, a direction of angular velocity, an acceleration of angular velocity, an angle, displacement information, a stress, etc.). Further, for example, the processing device 110 may determine whether the user movement is correct based on the feature information corresponding to the electromyographic signal and the feature information corresponding to the attitude signal. In some embodiments, the processing device 110 may further determine whether information of physiological parameters of the user during motion meets the health standard. In some embodiments, the processing device 110 may further send a corresponding instruction configured to feed the user's movement back. For example, when the user is running and the motion monitoring system 100 monitors that the user's running time is too long, the processing device 110 may send the instruction to the mobile terminal device 140 to prompt the user to adjust the running time. It should be noted that the feature information corresponding to the attitude signal is not limited to above angular velocity, the direction of angular velocity, the acceleration of angular velocity, the angle, the displacement information, and the stress, etc., but can also be other feature information. For example, when an attitude sensor is a strain gauge sensor, a bending angle and a bending direction at a user's joint may be obtained by measuring the resistance in a strain gauge sensor that varies with a stretch length.

In some embodiments, the processing device 110 may be local or remote. For example, the processing device 110 may access information and/or materials stored in the wearable device 130 and/or the mobile terminal device 140 through the network 120. In some embodiments, the processing device 110 may be directly connected to the wearable device 130 and/or the mobile terminal device 140 to access the information and/or materials stored therein. For example, the processing device 110 may be located in the wearable device 130 and implement the information interact with the mobile terminal device 140 through the network 120. Further, for example, the processing device 110 may be located in the mobile terminal device 140 and implement the information interact with the wearable device 130 through a network. In some embodiments, the processing device 110 may be executed on a cloud platform. For example, the cloud platform may include one of a private cloud, a public cloud, a hybrid cloud, a community cloud, a decentralized cloud, an internal cloud, or any combination thereof.

In some embodiments, the processing device 110 may process data and/or information related to motion monitoring to perform one or more of the functions described in the present disclosure. In some embodiments, the processing device 110 may obtain the movement signal collected by the wearable device 130 while the user is in motion. In some embodiments, the processing device may send a control instruction to the wearable device 130 or the mobile terminal device 140. The control instruction may control an on/off state of the wearable device 130 and its respective sensor, and also control the mobile terminal device 140 to send a prompt message. In some embodiments, processing device 110 may include one or more sub-processing devices (e.g., a single-core processing device or a multi-core processing device). Merely by way of example, the processing device 110 may include a central processing unit (CPU), an application-specific integrated circuit (ASIC), an application-specific instruction processor (ASIP), a graphic processing unit (GPU), a physics processing Unit (PPU), a digital signal processor (DSP), a field-programmable gate array (FPGA), an programmable logic device (PLD), a controller, a micro-controller unit Reduced Instruction Set Computer (RISC), and a microprocessor, etc. or any combination of the above.

The network 120 may facilitate an exchange of data and/or information in the motion monitoring system 100. In some embodiments, one or more components of the motion monitoring system 100 (e.g., the processing device 110, the wearable device 130, the mobile terminal device 140) may send the data and/or the information to other components of the motion monitoring system 100 through network 120. For example, the movement signal collected by the wearable device 130 may be transmitted to the processing device 110 through the network 120. For another example, confirmation results regarding the movement signal in the processing device 110 may be transmitted to the mobile terminal device 140 through the network 120. In some embodiments, the network 120 may be any type of a wired or wireless network. For example, the network 120 may include a cable network, a wired network, a fiber optic network, a telecommunications network, an internal network, an inter-network, a regional network (LAN), a wide area network (WAN), a wireless regional network (WLAN), a metropolitan area network (MAN), a public switched telephone network (PSTN), a Bluetooth™ network, a ZigBee™ network, and a near field communication (NFC) network, or any combination of the above. In some embodiments, the network 120 may include one or more network entry and exit points. For example, network 120 may include wired or wireless network entry and exit points, such as a base station and/or inter-network exchange points 120-1, 120-2, . . . , through the entry and exit points, one or more components of motion monitoring system 100 may connect to the network 120 to exchange the data and/or the information.

The wearable device 130 is a garment or device that has a wearable function. In some embodiments, the wearable device 130 may include, but is not limited to, an upper garment device 130-1, a pant device 130-2, a wrist guard device 130-3, and a shoe 130-4, etc. In some embodiments, wearable device 130 may include a plurality of sensors. The sensors may obtain various movement signals (e.g., electro-myographic signals, attitude signals, temperature informa-tion, heart rate, electro-cardio signals, etc.) from the user during motion. In some embodiments, the sensors may include, but are not limited to, one or more of an electro-myographic sensor, an attitude sensor, a temperature sensor, a humidity sensor, an electro-cardio sensor, an oxygen saturation sensor, a Hall sensor, a Pico electric sensor, and a rotation sensor, etc. For example, an electromyographic sensor may be provided at a human muscle location (e.g., biceps, triceps, latissimus dorsi, trapezius, etc.) in an upper garment device 130-1, and the electromyographic sensor may fit to user's skin and collect the electromyographic signal from the user during motion. For example, the upper garment device 130-1 may be provided with an electro-cardio sensor near the left pectoral muscle of the human body, and the electromyographic sensor may collect the electro-cardio signal of the user. Further, for example, the attitude sensor may be provided at a human body muscle location (e.g., gluteus maximus, lateral femoris, medial femoris, gastrocnemius, etc.) in a pants device 130-2, and the attitude sensor may collect a user's attitude signal. In some embodiments, the wearable device 130 may further provide feedback on the user's movement. For example, if the user's movement of a body part during motion does not meet the standard, the electromyographic sensor corre-sponding to that part may generate a stimulation signal (e.g., a current stimulation or a strike signal) to prompt the user.

It should be noted that the wearable device 130 is not limited to the upper garment device 130-1, the pants device 130-2, a wrist guard device 130-3, and a shoe device 130-4 shown in FIG. 1, but may further include a device that are applied to other devices that require motion monitoring, such as, for example, helmet devices, knee pads, etc., which will not be limited herein, and any device that can use the motion monitoring method contained in the disclosure is within the scope of protection of the present disclosure.

In some embodiments, the mobile terminal device 140 may access information or data in the motion monitoring system 100. In some embodiments, the mobile terminal device 140 may receive motion data processed by the processing device 110, and feed motion records back based on processed motion data. An exemplary feedback manner may include, but are not limited to, a voice prompt, an image prompts, a video display, and a text prompt, etc. In some embodiments, the user may obtain movement records during an own movement through the mobile terminal device 140. For example, the mobile terminal device 140 may be con-nected to the wearable device 130 through the network 120 (e.g., the wired connection, the wireless connection), and the user may obtain the movement records during the user's movement through the mobile terminal device 140, which may be transmitted to the processing device 110 through the mobile terminal device 140. In some embodiments, the mobile terminal device 140 may include a mobile device 140-1, a tablet 140-2, a laptop 140-3, etc., or any combina-tion thereof. In some embodiments, mobile device 140-1 may include a cell phone, a smart home device, a smart mobility device, a virtual reality device, an augmented reality device, etc., or any combination thereof. In some embodiments, the smart home device may include a control device of a smart appliance, a smart monitoring device, a smart TV, a smart camera, etc., or any combination thereof. In some embodiments, the smart mobility device may include a smart phone, a personal digital assistant (PDA), a gaming device, a navigation device, a POS device, etc., or any combination thereof. In some embodiments, a virtual reality device and/or an augmented reality device may include a virtual reality helmet, virtual reality glasses, a virtual reality eye-mask, an augmented reality helmet, an augmented reality glasses, and an augmented reality eye-mask, etc., or any combination thereof.

In some embodiments, the motion monitoring system 100 may further include a database. The database may store the information (e.g., a threshold condition of an initially set, etc.) and/or the instruction (e.g., a feedback instruction). In some embodiments, the database may store the information obtained from the wearable device 130 and/or the mobile terminal device 140. In some embodiments, the database may store the information and/or the instruction configured for the processing device 110 to execute or use to perform the exemplary methods described in the present disclosure. In some embodiments, the database may include a mass storage, a removable memory, a volatile read-write memory (e.g., random access memory RAM), a read-only memory (ROM), etc., or any combination thereof. In some embodi-ments, the database may be implemented on a cloud plat-form. For example, the cloud platform may include the private cloud, the public cloud, the hybrid cloud, the com-munity cloud, the decentralized cloud, the internal cloud, or any combination thereof.

In some embodiments, the database may be connected to the network 120 to communicate with one or more compo-nents of the motion monitoring system 100 (e.g., the pro-cessing device 110, the wearable device 130, the mobile terminal device 140, etc.). The one or more components of the motion monitoring system 100 may access information or instruction stored in the database through the network 120. In some embodiments, the database may be directly connected or communicate with one or more components of the motion monitoring system 100 (e.g., the processing device 110, the wearable device 130, the mobile terminal device 140). In some embodiments, the database may be a part of the processing device 110.

Figure 2:
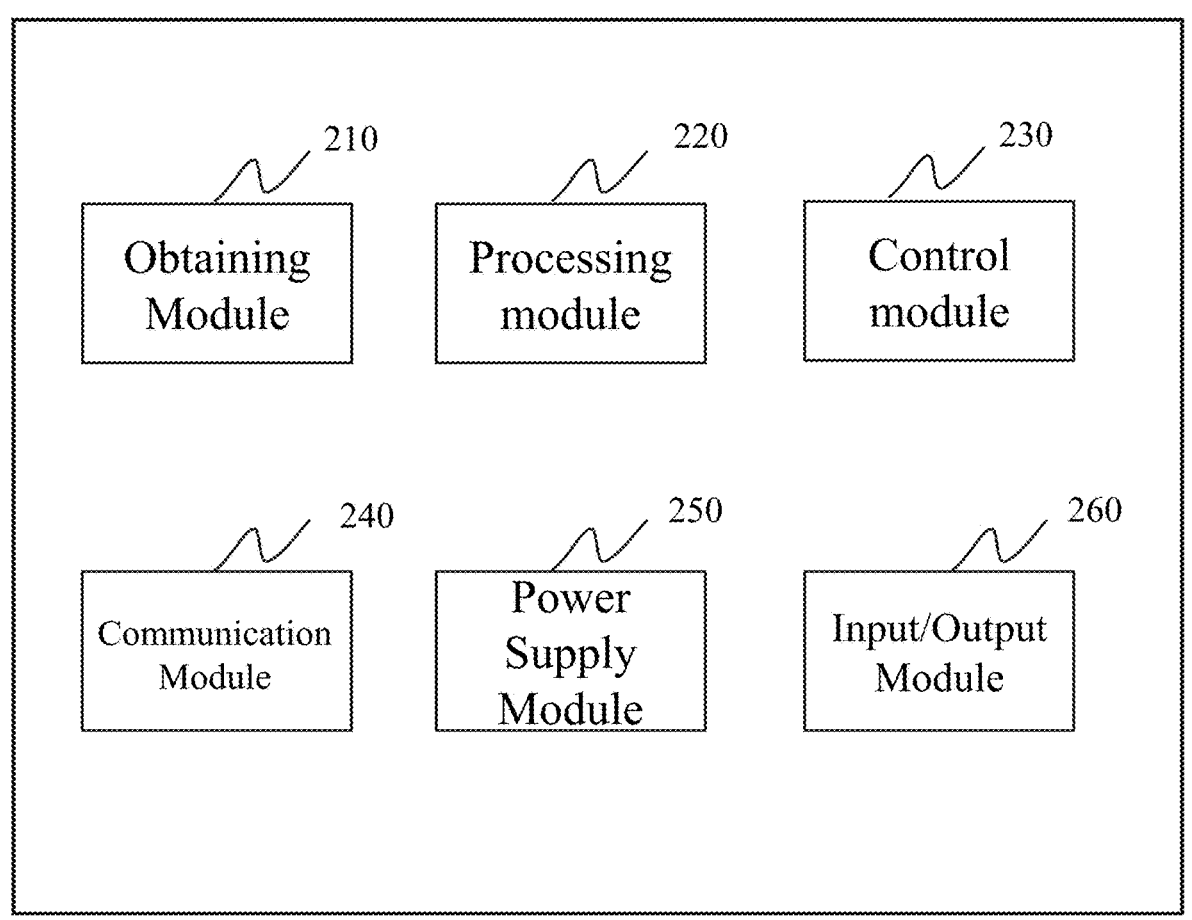
FIG. 2 is a schematic diagram illustrating an exemplary hardware and/or software of a wearable device according to some embodiments of the present disclosure.

FIG. 2 is a schematic diagram illustrating an exemplary hardware and/or software of a wearable device according to some embodiments of the present disclosure. As shown in FIG. 2, the wearable device 130 may include an obtaining module 210, a processing module 220 (also referred to as a processor), a control module 230 (also referred to as a master, MCU, a controller), a communication module 240, a power supply module 250, and an input/output module 260.

The obtaining module 210 may be configured to obtain a movement signal of a user during motion. In some embodi-ments, the obtaining module 210 may include a sensor unit, and the sensor unit may be configured to obtain one or more movement signals while the user is in motion. In some embodiments, the sensor unit may include, but is not limited to, one or more electromyographic sensors, attitude sensors, cardiac sensors, respiration sensors, temperature sensors, humidity sensors, inertial sensors, blood oxygen saturation sensors, Hall sensors, piezoelectric sensors, and rotation sensors, and the like. In some embodiments, the movement signal may include one or more electromyographic signals, attitude signals, cardiac signals, respiratory rates, temperature signals, and humidity signals, etc. The sensor unit may be placed at different locations of the wearable device 130 according to a type of a movement signal to be obtained. For example, in some embodiments, the electromyographic sensor (also referred to as an electrode element) may be placed at a human muscle location, and the electromyographic sensor may be configured to collect the electromyographic signal of the user during motion. The electromyographic signal and its corresponding feature information (e.g., frequency information, amplitude information, etc.) may reflect a state of muscle during a user's movement. The attitude sensor may be provided at different locations on a human body (e.g., locations of the wearable device 130 corresponding to the torso, limbs, and joints), and the attitude sensor may be configured to capture the attitude signal of the user during the user's movement. The attitude signal and its corresponding feature information (e.g., angular velocity direction, angular velocity value, acceleration value of angular velocity, angle, displacement information, stress, etc.) may reflect the attitude of the user's movement. The electromyographic sensor may be set at a location on the circumferential side of the human chest, and the electromyographic sensor may be configured to collect electro cardio data of the user during motion. The respiration sensor may be arranged on a circumferential side of the body's chest, and the respiration sensor may be configured to collect respiration data (e.g., respiration rate, respiration amplitude, etc.) from the user during motion. The temperature sensor may be configured to collect temperature data (e.g., a body surface temperature) of the user during motion. The humidity sensor may be configured to collect humidity data of an external environment of the user during motion.

The processing module 220 may process data from the obtaining module 210, the control module 230, the communication module 240, the power supply module 250, and/or the input/output module 260. For example, the processing module 220 may process the movement signal of the user during a process of motion from the obtaining module 210. In some embodiments, the processing module 220 may pre-process the movement signal (e.g., the electromyographic signal, the attitude signal) obtained by the obtaining module 210. For example, the processing module 220 segments the electromyographic signal or the attitude signal of the user during motion. For another example, the processing module 220 may perform a pre-processing (e.g., a filtering processing, a signal correction processing) on the electromyographic signal of the user during motion to improve quality of the electromyographic signal. Further, for example, the processing module 220 may determine the feature information corresponding to the attitude signal based on a user's attitude signal during motion. In some embodiments, the processing module 220 may process an instruction or operation from an input/output module 260. In some embodiments, processed data may be stored in a memory or a hard disk. In some embodiments, the processing module 220 may transmit its processed data to one or more components in the motion monitoring system 100 through the communication module 240 or the network 120. For example, the processing module 220 may send monitoring results of the user during motion to the control module 230, which may execute subsequent operations or instructions according to motion determination results.

The control module 230 may be connected to other modules in the wearable device 130. In some embodiments, the control module 230 may control an operation state of other modules (e.g., the communication module 240, the power supply module 250, the input/output module 260) in the wearable device 130. For example, the control module 230 may control a power supply state (e.g., a normal mode, a power saving mode), power supply time, and the like, of the power supply module 250. When remaining power of the power supply module 250 reaches a certain threshold (e.g., 10%) or less, the control module 230 may control the power supply module 250 to enter a power saving mode or send a prompt message about replenishment of power. For another example, the control module 230 may control the input/output module 260 based on user's movement determination results, and further control the mobile terminal device 140 to send feedback results of the user's movement. When there is a problem with the user's movement (e.g., movement not meeting the standard), the control module 230 may control the input/output module 260 to control the mobile terminal device 140 to provide feedback to the user, allowing the user to understand own motion movement in real time and make some adjustments. In some embodiments, the control module 230 may also control one or more sensors or other modules in the obtaining module 210 to provide feedback to the human body. For example, when a muscle of the user is exercising too strong during motion, the control module 230 may control an electrode module at a location of the muscle to stimulate the user to prompt the user to adjust the movement in time.

In some embodiments, the communication module 240 may be configured for an exchange of information or data. In some embodiments, the communication module 240 may be configured for communication between components (e.g., the obtaining module 210, the processing module 220, the control module 230, the power supply module 250, the input/output module 260) within a wearable device 130. For example, the obtaining module 210 may send a movement signal (e.g., the electromyographic signal, the attitude signal, etc.) to the communication module 240, and the communication module 240 may send the movement signal to the processing module 220. For example, the communication module 240 may send state information (e.g., a switch state) of the wearable device 130 to the processing device 110, and the processing device 110 may monitor the wearable device 130 based on the state information. The communication module 240 may employ wired, wireless, and hybrid wired/wireless technologies. The wired technology may be based on one or more combinations of fiber optic cables such as metallic cables, hybrid cables, fiber optic cables, etc. The wireless technologies may include Bluetooth (Bluetooth™), wireless network (Wi-Fi), purple bee (ZigBee™), Near Field Communication (NFC), Radio Frequency Identification (RFID), cellular networks (including GSM, CDMA, 3G, 4G, 5G, etc.), and cellular-based Narrow Band Internet of Things (NBIoT), etc. In some embodiments, the communication module 240 may use one or more coding methods to encode transmitted information, for example, the coding methods may include phase coding, non-zeroing coding, differential Manchester coding, and the like. In some embodiments, the communication module 240 may select different transmission and encoding methods according to a type of data or a type of network to be transmitted. In some embodiments, the communication module 240 may include one or more communication interfaces for different communication methods. In some embodiments, illustrated other modules of the motion monitoring system 100 may be dispersed on a plurality of devices, in this case, each of a plurality of other modules may each include one or more communication modules 240 for an inter-module information transmission. In some embodiments, the communication module 240 may include a receiver and a transmitter. In other embodiments, the communication module 240 may be a transceiver.

In some embodiments, the power supply module 250 may provide power to other components in the motion monitoring system 100 (e.g., the obtaining module 210, the processing module 220, the control module 230, the communication module 240, and the input/output module 260). The power supply module 250 may receive the control signal from the processing module 220 to control a power output of the wearable device 130. For example, if the wearable device 130 does not receive any operation (e.g., no movement signal is detected by the obtaining module 210) for a certain period (e.g., 1 s, 2 s, 3 s, or 4 s), the power supply module 250 may supply power to the memory merely, putting the wearable device 130 into a standby mode. For example, if the wearable device 130 does not receive any operation (e.g., no movement signal is detected by the obtaining module 210) for a certain period (e.g., 1 s, 2 s, 3 s, or 4 s), the power supply module 250 may disconnect power to other components and the data in the motion monitoring system 100 may be transmitted to a hard disk, putting the wearable device 130 into the standby mode or a sleeping mode. In some embodiments, the power supply module 250 may include at least one battery. The battery may include one or more combinations of a dry cell, a lead battery, a lithium battery, a solar cell, a wind energy generation battery, a mechanical energy generation battery, a thermal energy generation battery, etc. Light energy maybe converted into electrical energy by the solar battery and stored in the power supply module 250. Wind energy may be converted into the electrical energy by the wind power generation battery and stored in the power supply module 250. Mechanical energy may be converted into the electrical energy by the mechanical energy generation battery and stored in the power supply module 250. The solar cell may include a silicon solar cell, a thin film solar cell, a nanocrystalline chemical solar cell, a fuel sensitized solar cell, and a plastic solar cell, etc. The solar cell may be distributed on the wearable device 130 in a form of panel. A user's body temperature may be converted into the electrical energy by the thermal power cell and stored in the power supply module 250. In some embodiments, the processing module 220 may send the control signal to the power supply module 250 when the power supply module 250 is less than a power threshold (e.g., 10% of the total power). The control signal may include information that the power supply module 250 is low on power. In some embodiments, the power supply module 250 may include a backup power source. In some embodiments, the power supply module 250 may further include a charging interface. For example, the power supply module 250 may be temporarily charged by using an electronic device (e.g., a cell phone, a tablet computer) or a rechargeable battery carried by the user to temporarily charge the power supply module 250 in an emergency (e.g., the power supply module 250 is at zero power and an external power system is out of power).

The input/output module 260 may obtain, transmit, and send a signal. The input/output module 260 may connect or communicate with other components in the motion monitoring system 100. The other components in the motion monitoring system 100 may be connected or communicated through the input/output module 260. The input/output module 260 may be a wired USB interface, a serial communication interface, a parallel communication port, or a wireless Bluetooth, infrared-frequency identification, radio-frequency identification (RFID), WLAN Authentication and Privacy Infrastructure (WAPI), General Packet Radio Service (GPRS), Code Division Multiple Access (CDMA), or any combination thereof. In some embodiments, the input/output module 260 may be connected to the network 120 and obtain the information through the network 120. For example, the input/output module 260 may obtain the movement signal from the obtaining module 210 of the user during motion and output user movement information through the network 120 or the communication module 240. In some embodiments, the input/output module 260 may include VCC, GND, RS-232, RS-485 (e.g., RS485-A, RS485-B), and a universal network interface, or any combination thereof. In some embodiments, the input/output module 260 may transmit obtained user motion information, through the network 120, to the obtaining module 210. The encoding methods may include the phase coding, the nonzeroing system encoding, the differential Manchester encoding, etc., or any combination thereof.

It should be understood that the system and its modules shown in FIG. 2 may be implemented by using a plurality of methods. For example, in some embodiments, the system and its modules may be implemented by hardware, software, or a combination of software and hardware. In particular, a hardware portion may be implemented by using dedicated logic. A software portion may be stored in memory and executed by an appropriate instruction execution system, such as a microprocessor or dedicated design hardware. Those skilled in the art may understand that the above methods and the system can be implemented by using a computer executable instruction and/or contained in a processor control code, for example, such encoding provided on a carrier medium such as a disk, CD or DVD-ROM, a programmable memory such as a read-only memory (firmware), or a data carrier such as an optical or electronic signal carrier. The system and its modules in one or more embodiments of the present disclosure may be implemented by a hardware circuit, e.g., ultra-large scale integrated circuit or gate array, a semiconductor such as a logic chip, a transistor, etc., or a programmable hardcore device such as a field programmable gate array, a programmable logic device, etc., implemented by software executed by various types of processors, or implemented by a combination of above hardware circuit and software (e.g., firmware).

It should be noted that the above description of the motion monitoring system and its modules is merely for descriptive convenience and does not limit one or more embodiments of the present disclosure within the scope of the embodiments. Understandably, for those skilled in the art, after understanding a principle of the system, they may make any combination of the modules, or to form a sub-system to connect with other modules, or to omit one or more modules thereof, without departing from this principle. For example, the obtaining module 210 and the processing module 220 may be one module that may have a function of obtaining and processing the user movement signal. Another example is that the processing module 220 may not be provided in the wearable device 130, but integrated in the processing device 110. Variations such as these are within the scope of protection of one or more embodiments of the present disclosure.

Figure 3:
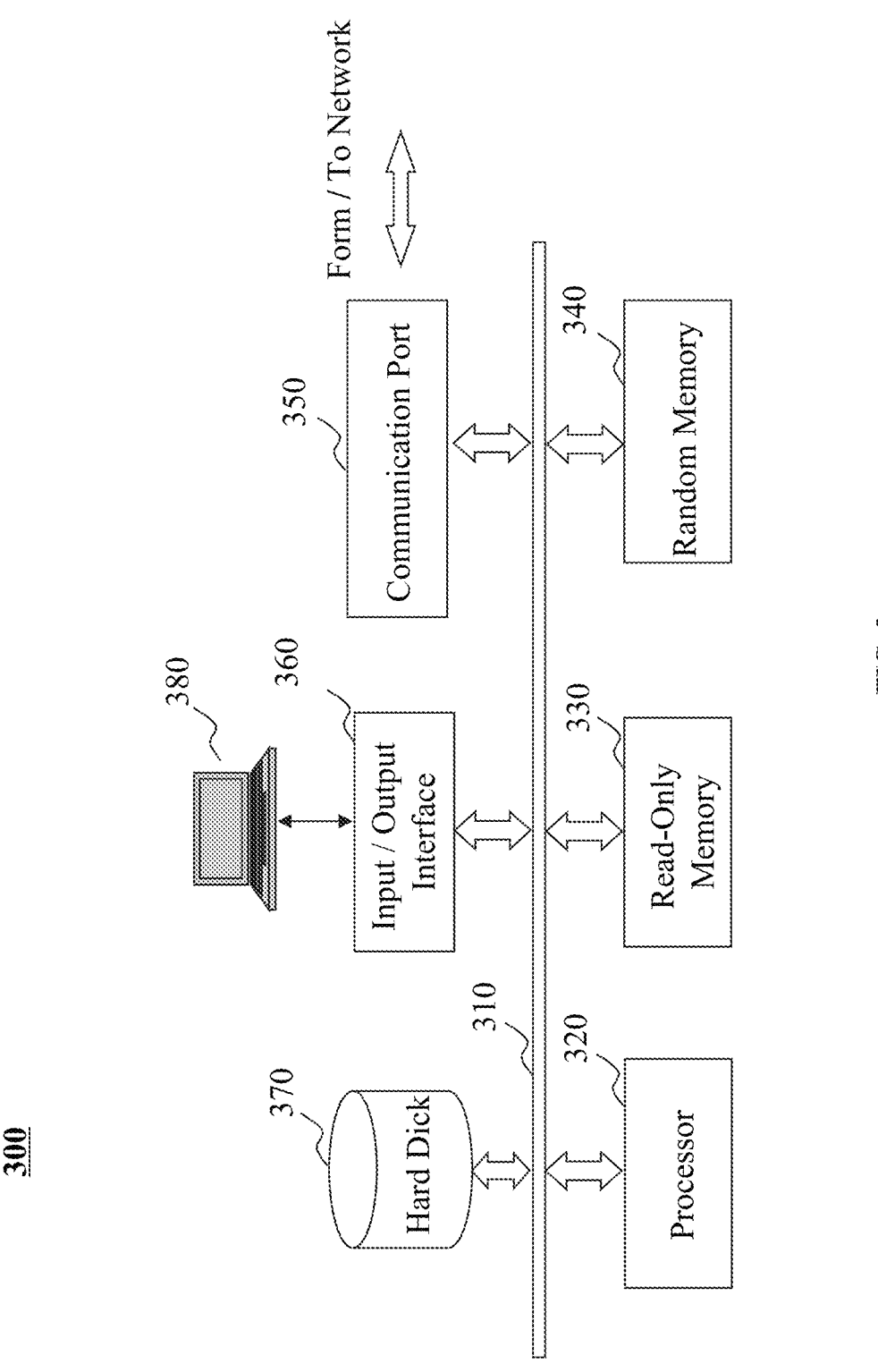
FIG. 3 is a schematic diagram illustrating an exemplary hardware and/or software of a computing device according to some embodiments of the present disclosure.

FIG. 3 is a schematic diagram illustrating an exemplary hardware and/or software of a computing device according to some embodiments of the present disclosure. In some embodiments, the processing device 110 and/or the mobile terminal device 140 may be implemented on a computing device 300. As shown in FIG. 3, the computing device 300 may include an internal communication bus 310, a processor 320, a read-only memory 330, a random memory 340, a communication port 350, an input/output interface 360, a hard disk 370, and a user interface 380.

The internal communication bus 310 may enable data communication between components in the computing device 300. For example, the processor 320 may send data to other hardware such as a memory or the input/output interface 360 through the internal communication bus 310. In some embodiments, the internal communication bus 310 may be an industry standard architecture (ISA) bus, an extended industry standard architecture (EISA) bus, a video electronics standard architecture (VESA) bus, and a peripheral component interconnect (PCI) bus, etc. In some embodiments, the internal communication bus 310 may be configured to connect various modules (e.g., obtaining module 210, processing module 220, control module 230, communication module 240, input and output module 260) of the motion monitoring system 100 shown in FIG. 1.

The processor 320 may execute a computing instruction (a program code) and perform functions of the motion monitoring system 100 described in the present disclosure. The computing instruction may include a program, an object, a component, a data structure, process, modules, and functions (the functions refer to specific functions described in the present disclosure). For example, processor 320 may process the obtained movement signal (e.g., the electromyographic signal, the attitude signal) of a user during motion from the wearable device 130 or/and the mobile terminal device 140 of the motion monitoring system 100, and monitor the movement of the user during motion based on the movement signal during motion. In some embodiments, the processor 320 may include a microcontroller, a microprocessor, a reduced instruction set computer (RISC), an application-specific integrated circuit (ASIC), an application-specific instruction-set processor (ASIP), a central processing unit (CPU), a graphics processing unit (GPU), a physical processing unit (PPU), a microcontroller unit, a digital signal processor (DSP), a field Programmable Gate Array (FPGA), an Advanced RISC Machine (ARM), a programmable logic device, and any circuit and processor capable of performing one or more functions, or any combination thereof. For illustrative purposes only, the computing device 300 in FIG. 3 depicts only one processor, but it should be noted that the computing device 300 in the present disclosure may further include a plurality of processors.

A memory of computing device 300 (e.g., a read-only memory (ROM) 330, a Random Access Memory (RAM) 340, a hard disk 370, etc.) may store data/information obtained from any other components of the motion monitoring system 100. In some embodiments, the memory of the computing device 300 may be located in the wearable device 130 or the processing device 110. An exemplary ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. An exemplary RAM may include a dynamic RAM (DRAM), a double-rate synchronous dynamic RAM (DDR SDRAM), a static RAM (SRAM), a thyristor RAM (T-RAM), and a zero-capacitor RAM (Z-RAM), etc.

The input/output interface 360 may input or output signals, data, or information. In some embodiments, the input/output interface 360 may enable a user to interact with the motion monitoring system 100. For example, the input/output interface 360 may include a communication module 240 to enable the communication function of the motion monitoring system 100. In some embodiments, the input/output interface 360 may include an input device and an output device. Exemplary input devices may include a keyboard, a mouse, a touch screen, and a microphone, etc., or any combination thereof. Exemplary output devices may include a display device, a loudspeaker, a printer, a projector, etc., or any combination thereof. Example display devices may include a liquid crystal display (LCD), a light-emitting diode (LED)-based display, a flat panel display, a curved display, a television device, a cathode ray tubes (CRT), etc., or any combination thereof. The communication port 350 may be connected to a network for data communication. Connection may be a wired connection, a wireless connection, or a combination of both. The wired connection may include a cable, a fiber optic cable, or telephone line, or any combination thereof. The wireless connection may include Bluetooth™, Wi-Fi, WiMAX, WLAN, ZigBee™, a mobile network (e.g., 3G, 4G, or 5G, etc.), or any combination thereof. In some embodiments, the communication port 350 may be a standard port, such as RS232, RS485, etc. In some embodiments, the communication port 350 may be a specially designed port.

The hard disk 370 may be configured to store the information and the data generated by or received from the processing device 110. For example, the hard disk 370 may store confirmation information of a user. In some embodiments, the hard disk 370 may include a hard disk drive (HDD), a solid-state drive (SSD), or a hybrid hard disk (HHD), etc. In some embodiments, the hard disk 370 may be provided in the processing device 110 or in the wearable device 130. The user interface 380 may enable an interact and information exchange between the computing device 300 and the user. In some embodiments, the user interface 380 may be configured to present motion recordings generated by the motion monitoring system 100 to the user. In some embodiments, the user interface 380 may include a physical display such as a display with speakers, an LCD display, an LED display, an OLED display, an electronic ink display (E-Ink), etc.

Figure 4:
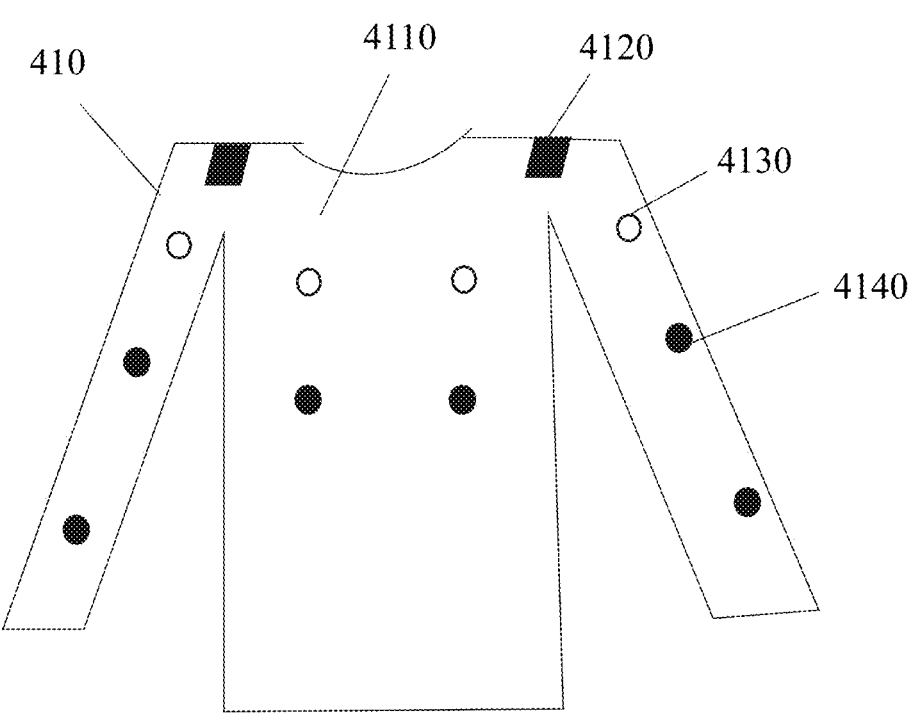
FIG. 4 is a structure diagram of an exemplary wearable device according to some embodiments of the present disclosure.

FIG. 4 is a structure diagram of an exemplary wearable device according to some embodiments of the present disclosure. To further describe the wearable device, the upper garment is illustrated as an example, as shown in FIG. 4. The wearable device 400 may include an upper garment 410. The upper garment 410 may include an upper garment substrate 4110, at least one upper garment processing module 4120, at least one upper garment feedback module 4130, at least one upper garment obtaining module 4140, etc. The upper garment substrate 4110 may refer to clothe worn on an upper body of a human body. In some embodiments, the upper garment substrate 4110 may include a short sleeve T-shirt, a long sleeve T-shirt, a shirt, and a jacket, etc. The at least one upper garment processing module 4120, the at least one upper garment obtaining module 4140 may be located in areas of the upper garment substrate 4110 that fit to different parts of the human body. The at least one upper garment feedback module 4130 may be located at any location on the upper garment substrate 4110, and the at least one upper garment feedback module 4130 may be configured to provide feedback on information about a user's upper body movement state. Exemplary feedback manners may include, but are not limited to, voice prompts, text prompts, pressure prompts, electrical stimulation, etc. In some embodiments, the at least one upper garment obtaining module 4140 may include, but is not limited to, one or more of an attitude sensor, an electro-cardio sensor, an electromyographic sensor, a temperature sensor, a humidity sensor, an inertial sensor, an acid-base sensor, an acoustic transducer, and etc. The sensor(s) in the upper garment obtaining module 4140 may be placed at different locations on user's body according to a signal to be measured. For example, when the attitude sensor is configured to obtain the attitude signal of a user during motion, the attitude sensor can be placed in the upper garment substrate 4110 at a location corresponding to the human torso, arms, and joints. For another example, when the electromyographic sensor is configured to obtain Electromyographic signal of the user during motion, the Electromyographic sensor may be located near the muscles to be measured. In some embodiments, the attitude sensor may include, but is not limited to, an acceleration triaxial sensor, an angular velocity tri-axial sensor, a magnetic sensor, etc., or any combination thereof. For example, an attitude sensor may include an acceleration triaxial sensor, an angular velocity triaxial sensor. In some embodiments, an attitude sensor may further include a strain gauge sensor. A strain gauge sensor may be a sensor based on strain generated by deformation of an object to be measured caused by a force. In some embodiments, the strain gauge sensor may include, but is not limited to, one or more of a strain-gauge force sensor, a strain-gauge pressure sensor, a strain-gauge torque sensor, a strain-gauge displacement sensor, a strain-gauge acceleration sensor, etc. For example, the strain gauge sensor may be arranged at a joint location of the user, and a bending angle and a bending direction at the user's joint can be obtained based on the resistance in the strain gauge sensor that varies with a stretch length at the joint. It should be understood that the upper garment 410 may include other modules, such as a power supply module, a communication module, an input/output module, and etc., in addition to the upper garment substrate 4110, the upper garment processing module 4120, the upper garment feedback module 4130, and the upper garment obtaining module 4140 described above. The upper garment processing module 4120 is similar to the processing module 220 shown in FIG. 2, and the upper garment obtaining module 4140 is similar to the obtaining module 210 shown in FIG. 2. Specific descriptions regarding various modules in the upper garment 410 may be found in FIG. 2 and its relevant descriptions of the present disclosure, which will not be repeated herein.

FIG. 5 is a flowchart illustrating an exemplary motion monitoring method according to some embodiments of the present disclosure. As shown in FIG. 5, process 500 may include the following steps.

In step 510, obtaining a movement signal of a user during motion.

In some embodiments, the step 510 may be performed by the obtaining module 210. The movement signal refers to human body parameter information of the user during motion. In some embodiments, the human body parameter information may include, but is not limited to, one or more of an electromyographic signal, an attitude signal, an electro-cardio signal, a temperature signal, a humidity signal, a blood oxygen concentration, and a respiration rate, etc. In some embodiments, an electromyographic sensor in the obtaining module 210 may collect the electromyographic signal of the user during motion. For example, when the user performs a seated chest press, the electromyographic sensors in a wearable device corresponding to human pectoral muscles, latissimus dorsi, etc. may obtain the electromyographic signals of corresponding muscle positions of the user. For another example, when a user performs a deep squat, the electromyographic sensors in the wearable device corresponding to gluteus maximus and quadriceps can collect the electromyographic signals of the corresponding muscle positions. For another example, when the user is running, the electromyographic sensors in the wearable device corresponding to a gastrocnemius muscle and other positions can obtain the electromyographic signals of the corresponding muscle positions. In some embodiments, the attitude sensor in the obtaining module 210 may obtain an attitude signal of the user during motion. For example, when the user performs a barbell bench press, the attitude sensor in the wearable device corresponding to the human triceps, etc., can obtain the attitude signal of the triceps, etc. For example, when the user performs a dumbbell flyover, the attitude sensor set at a position such as a human deltoid muscle may obtain the attitude signal of the corresponding position. In some embodiments, a plurality of attitude sensors may obtain attitude signals of a plurality of portions of the user during motion, and the attitude signals of a plurality of portions may reflect a relative movement between different parts of the body. For example, an attitude signal at an arm and an attitude signal at a torso can reflect a movement condition of the arm relative to the torso. In some embodiments, the attitude signal is associated with a type of the attitude sensor. For example, when the attitude sensor is an angular velocity tri-axis sensor, an obtained attitude signal is angular velocity information. For another example, when the attitude sensor is the angular velocity tri-axis sensor and an acceleration tri-axis sensor, the obtained attitude signal is the angular velocity information and acceleration information. For example, when the attitude sensor is a strain gauge sensor, the strain gauge sensor can be arranged at a user's joint position, by measuring the resistance in the strain gauge sensor that varies with the stretch length, the obtained attitude signal may be displacement information, stress, etc., and a bending angle and a bending direction at the user's joint may be represented through these attitude signals. It is important to note that the parameter information configured to reflect the relative motion of the user's body may be feature information corresponding to the attitude signal, which can be obtained by using different types of attitude sensors according to the type of the feature information.

In some embodiments, the movement signal may include the electromyographic signal and an attitude signal of a particular part of the user's body. The electromyographic signal and the attitude signal can reflect a movement state of the particular part of the user's body from different angles. In simple terms, the attitude signal of a specific part of the user's body can reflect the type of movement, movement amplitude, movement frequency, etc. of the specific part. The electromyographic signal may reflect a muscle state of the particular part during motion. In some embodiments, by measuring the electromyographic signal and/or the attitude signal of the same body part, whether the movement of that part is standard can be better assessed.

In step 520, monitoring the movement of the user during motion based at least on feature information corresponding to the electromyographic signal or feature information corresponding to the attitude signal.

In some embodiments, the step 520 may be performed by the processing module 220 and/or the processing device 110. In some embodiments, the feature information corresponding to the electromyographic signal may include, but is not limited to, one or more of frequency information, amplitude information, etc. The feature information corresponding to the attitude signal is parameter information configured to represent the relative motion of the user's body. In some embodiments, the feature information corresponding to the attitude signal may include, but is not limited to, one or more of an angular velocity direction, an angular velocity value, an acceleration value of angular velocity, etc. In some embodiments, the feature information corresponding to the attitude signal may further include an angle, displacement information (e.g., a stretch length in a strain gauge sensor), stress, etc. For example, when the attitude sensor is a strain gauge sensor, the strain gauge sensor may be set at the user's joint position, and by measuring the resistance in the strain gauge sensor that varies with the stretch length, the obtained attitude signal may be displacement information, stress, etc., which may represent the bending angle and the bending direction at the user's joint. In some embodiments, the processing module 220 and/or the processing device 110 may extract the feature information corresponding to the electromyographic signal (e.g., frequency information, amplitude information) or the feature information corresponding to the attitude signal (e.g., the angular velocity direction, the angular velocity value, the acceleration value of angular velocity, the angle, the displacement information, the stress, etc.), and monitor the movement of the user during motion based on the feature information corresponding to the electromyographic signal or the feature information corresponding to the attitude signal. The monitoring of the movement during motion includes user's movement-related information. In some embodiments, movement-related information may include one or more of a movement type, number of movements, a movement quality (e.g., whether the movement meets a standard), a movement time, etc. The movement type is a fitness movement performed by the user during motion. In some embodiments, the movement type may include, but is not limited to, one or more of seated chest presses, deep squats, hard pulls, plank supports, running, swimming, etc. The number of movements refers to the number of times the user performs the movement during motion. For example, if the user performs 10 seated chest clamps during motion, 10 is the number of movements. The movement quality refers to the standard degree of the fitness movement performed by the user related to a standard fitness movement. For example, when the user performs a deep squat movement, the processing device 110 may determine a movement type of the user based on the feature information corresponding to the movement signal (the electromyographic signal and the attitude signal) of a particular specific muscle location (gluteus maximus, quadriceps, etc.) and determine the movement quality of the user during performing the deep squat movement based on the movement signal. The movement time is the time corresponding to one or more movement types of the user or the total time of the movement process. Detailed descriptions of monitoring the movement of the user during motion based on the feature information corresponding to the electromyographic signal and/or the feature information corresponding to the attitude signal may be found in FIG. 6 and its relevant descriptions of the present disclosure.

In some embodiments, the processing device 110 may use one or more movement recognition models to recognize and monitor the movement of the user during motion. For example, the processing device 110 may input the feature information corresponding to the electromyographic signal and/or the feature information corresponding to the attitude signal into a movement recognition model, and the movement recognition model outputs information related to the user's movement. In some embodiments, the movement recognition model may include different types of movement recognition models, for example, a model configured to recognize the movement type of the user, or a model configured to identify movement quality of the user, etc.

It should be noted that the above description regarding process 500 is for exemplary and illustrative purpose only, and does not limit the scope of application of the present disclosure. For those skilled in the art, various amendments and changes can be made to the process 500 under the guidance of the present disclosure. However, these amendments and changes remain within the scope of the present disclosure. For example, extraction of the feature information corresponding to the electromyographic signal or the feature information corresponding to the attitude signal in step 520 may be performed through the processing device 110, or in some embodiments, by processing module 220. For example, the user's movement signal is not limited to the above electromyographic signal, attitude signal, electro-cardio signal, temperature signal, humidity signal, blood oxygen concentration, respiration rate, but may also include other human physiological parameter signal, and the physiological parameter signals involved in human movement can be all considered as the movement signal in the embodiments of the present disclosure.

FIG. 6 is a flowchart of an exemplary process for monitoring a movement of a user during motion according to some embodiments of the present disclosure. As shown in FIG. 6, process 600 may include the following steps.

In step 610, segmenting, based on the feature information corresponding to the electromyographic signal or the feature information corresponding to the attitude signal, the movement signal.

In some embodiments, the step may be performed by the processing module 220 and/or the processing device 110. The process of obtaining the movement signal (e.g., the electromyographic signal, the attitude signal) of the user during motion is continuous, and a movement of the user during motion may be a combination of a plurality of sets of movement or a combination of different movement types. To analyze each movement of the user during motion, the processing module 220 may segment the movement signal of the user based on the feature information corresponding to the electromyographic signal or the feature information corresponding to the attitude signal. The segmenting the movement signal of the user herein refers to dividing the movement signal into signal segments having same or different durations, or extract one or more signal segments having a specific duration from the movement signal. In some embodiments, each segment of the movement signal may correspond to one or more complete movement of the user. For example, when a user performs a deep squat, the user's movement from a standing position to a squat position and then getting up to return to the standing position can be considered as completing the deep squat, and the movement signal collected by the obtaining module 210 during this process can be considered as one segment (or one cycle) of the movement signal, after which the movement signal collected by the obtaining module 210 from the next deep squat completed by the user can be considered as another segment of the movement signal. In some embodiments, each movement signal may also correspond to a portion of the user's movement, where a portion of the movement may be understood as a portion of a complete movement. For example, when a user performs a deep squat, the user's movement from a standing position to a squat position may be considered as one segment of the movement, and getting up to return to the standing position may be considered as another segment of the movement. A change in each movement of the user during motion may cause the electromyographic signal and the attitude signal of a corresponding body part to change. For example, when the user performs a squat, the electromyographic signal and the attitude signal of the muscles in the corresponding parts of the user's body (e.g., arms, legs, hips, abdomen) fluctuate less when the user stands; when the user squats from the standing position, the electromyographic signal and the attitude signal of the muscles in the corresponding parts of the user's body fluctuate more, e.g., amplitude information corresponding to signals of different frequencies of the electromyographic signal becomes greater, or an angular velocity value, a direction of angular velocity, an acceleration value of angular velocity, an angle, displacement information, stress, etc. of the attitude signal may also change. When the user gets up from a squatting state to a standing state, the amplitude information corresponding to the electromyographic signal and the angular velocity value, the direction of angular velocity, the acceleration value of angular velocity, the angle, the displacement information, and the stress corresponding to the attitude signal may change again. Based on this situation, the processing module 220 may segment, based on the feature information corresponding to the electromyographic signal or the feature information corresponding to the attitude signal, the movement signal. Detailed descriptions of segmenting the movement signal based on the feature information corresponding to the electromyographic signal or the feature information corresponding to the attitude signal may be found in FIG. 7 and FIG. 8 of the present disclosure and their related descriptions.

In step 620, monitoring, based on at least one segment of the movement signal, the movement of the user during motion.

The step may be performed by processing module 220 and/or processing device 110. In some embodiments, monitoring of the movement of the user based on at least one segment of the movement signal may include matching the at least one segment of the movement signal with at least one segment of a preset movement signal to determine the movement type of the user. The at least one segment of the preset movement signal is standard movement signals corresponding to different movements that are preset in a database. In some embodiments, a movement type of the user during motion may be determined by determining a matching degree of the at least one segment of the movement signal and the at least one segment of the preset movement signal. Further, the movement type of the user may be determined by determining whether the matching degree of the movement signal and the preset movement signal is within a first matching threshold range (e.g., greater than 80%). If so, the movement type of the user during motion is determined based on the movement type corresponding to the preset movement signal. In some embodiments, monitoring the movement of the user during motion based on the at least one segment of the movement signal may further include determining the movement type of the user during motion by matching the feature information corresponding to the at least one segment of the electromyographic signal and feature information corresponding to an electromyographic signal of the at least one segment of the preset movement signal. For example, match degree(s) between one or more feature information (e.g., frequency information, amplitude information) of the segment of the electromyographic signal and the one or more feature information of the segment of the preset movement signal may be calculated respectively, and a determination is made as to whether a weighted matching degree of the one or more feature information or an average matching degree of the one or more feature information is within a first matching threshold. If so, the movement type of the user during motion is determined based on the movement type corresponding to the preset movement signal. In some embodiments, monitoring the movement of the user during motion based on the at least one segment of the movement signal may further include determining the movement type of the user during motion by matching the feature information corresponding to the at least one segment of the attitude signal with the feature information corresponding to the attitude signal of the at least one segment of the preset movement signal. For example, the matching degree of the one or more feature information (e.g., the angular velocity value, the angular velocity direction and the acceleration value of the angular velocity, the angle, the displacement information, the stress, etc.) of one segment of the attitude signal and the one or more feature information of one segment of the preset movement signal are calculated respectively to determine whether the weighted matching degree or the average matching degree of the one or more feature information is within the first matching threshold. If so, the movement type of the user is determined according to preset a movement type corresponding to the preset movement signal. In some embodiments, monitoring the movement of the user during motion based on the at least one segment of the movement signal may further include determining the movement type of the user during motion by matching the feature information corresponding to the electromyographic signal and the feature information corresponding to the attitude signal of the at least one segment of the movement signal and the feature information corresponding to the electromyographic signal and the feature information corresponding to the attitude signal of the at least one segment of the preset movement signal.

In some embodiments, monitoring the movement of the user during motion based on the at least one segment of the movement signal may include determining the movement quality of the user by matching the at least one segment of the movement signal with the at least one segment of the preset movement signal. Further, if a matching degree of the movement signal and the preset movement signal is within a second matching threshold range (e.g., greater than 90%), the movement quality of the user during motion meets the standard. In some embodiments, determining the movement of the user during motion based on the movement signal of the at least one segment may include determining the movement quality of the user during motion by matching the one or more feature information of the movement signal of the at least one segment with the one or more feature information of the at least one segment of the preset movement signal. It should be noted that a segment of the movement signal may be a movement signal of a complete movement or a movement signal of a partial of a complete movement. In some embodiments, for a complex complete movement, there may be different ways of force generation at different stages of the complete movement, that is, there may be different movement signals at the different stages of the movement, and the user movement can be monitored in real time, and thus, the accuracy of the monitored movement signal at the different stages of the complete movement can be improved.

It should be noted that the above description of the process 600 is for example and illustration purposes only and does not limit the scope of application of the present disclosure. For those skilled in the art, various amendments and changes can be made to process 600 under the guidance of the present disclosure. However, these amendments and changes remain within the scope of the present disclosure. For example, in some embodiments, the user's movement may also be determined through a movement recognition model or a manually preset model.

FIG. 7 is a flowchart of an exemplary process for segmenting a movement signal according to some embodiments of the present disclosure. As shown in FIG. 7, process 700 may include the following steps.

In step 710, determining, based on a time domain window of the electromyographic signal or the attitude signal, at least one target feature point from within the time domain window according to a preset condition.

In some embodiments, the step may be performed by the processing module 220 and/or the processing device 110. The time domain window of the electromyographic signal includes an electromyographic signal over a range of time, and the time domain window of the attitude signal includes an attitude signal over a same range of time. A target feature point refers to a signal of the movement signal with a target feature, which may represent a stage of the user's movement. For example, when a user performs a seated chest press, at the beginning, the user's arms are extended outward horizontally, begin to rotate internally, come together, and finally return to the extended state again in the horizontal direction, this process is a complete seated chest press movement. When the user performs a seated chest press movement, the feature information corresponding to the electromyographic signal or the attitude signal is different in each stage. By analyzing the feature information corresponding to the electromyographic signal (e.g., amplitude information, frequency information) or the feature information corresponding to the attitude signal (e.g., the angular velocity value, the direction of angular velocity, the acceleration value of angular velocity, the angle, the displacement information, the stress, etc.), the target feature point corresponding to a stage of the user's movement may be determined. In some embodiments, one or more target feature points may be determined from the time domain window based on the preset condition. In some embodiments, the preset condition may include one or more of a change in the direction of the angular velocity corresponding to the attitude signal, the angular velocity corresponding to the attitude signal being greater than or equal to an angular velocity threshold, the angle corresponding to the attitude signal reaching an angular threshold, the change of the angular velocity value corresponding to the attitude signal being the extreme value, and the amplitude information corresponding to the electromyographic signal being greater than or equal to an electromyographic threshold. In some embodiments, the target feature points at the different stages of a movement may correspond to different preset conditions. For example, in the seated chest press, a preset condition for a target feature point when the user's arms are horizontally extended outward and then start to internally rotate is different from a preset condition for a target feature point when the arms are brought together. In some embodiments, the target feature points of different movements may correspond to different preset conditions. For example, the chest press movement and bent-over movement are different, and the preset conditions regarding the respective preset target feature points in these two movements are also different. Exemplary descriptions of the preset condition may refer to the description of a movement start point, a movement middle point and a movement end point in the present disclosure.

In other embodiments, the at least one target feature point may be determined, based on the both time domain windows of the electromyographic signal and the attitude signal, from the time domain windows according to the preset condition. The time domain windows of the electromyographic signal and the attitude signal both include the electromyographic signal and the attitude signal over a range of time. The time of the electromyographic signal corresponds to the time of the attitude signal. For example, a time point of the electromyographic signal when the user starts to move is the same as a time point of the attitude signal when the user starts to move. The target feature point here may be determined by combining the feature information corresponding to the electromyographic signal (e.g., the amplitude information) and the feature information corresponding to the attitude signal (e.g., the angular velocity value, the direction of angular velocity, the acceleration value of angular velocity, the angle, etc.).

In step 720, segmenting, based on the at least one target feature point, the movement signal.

In some embodiments, the step 720 may be performed by the processing module 220 and/or the processing device 110. In some embodiments, the target feature point in the electromyographic signal or the attitude signal may be one or more, and the movement signal may be divided into multiple segments by one or more target feature points. For example, when there is a target feature point in the electromyographic signal, the target feature point may divide the electromyographic signal into two segments, where the two segments may include the electromyographic signal before the target feature point and the electromyographic signal after the target feature point. Alternatively, the processing module 220 and/or the processing device 110 may extract the electromyographic signal for a certain time range around the target feature point as a segment of the electromyographic signal. For another example, when the electromyographic signal has a plurality of target feature points (e.g., n-target feature points, and the first target feature point is not a beginning of the time domain window and the $n^{th}$ target feature point is not an end of the time domain window), the electromyographic signal may be divided into (n+1) segments based on the n target feature points. For another example, when the electromyographic signal has the plurality of target feature points (e.g., n-target feature points, and the first target feature point is the beginning of the time domain window and the $n^{th}$ target feature point is not the end of the time domain window), the electromyographic signal may be divided into n segments based on the n target feature points. As a further example, when the electromyographic signal has the plurality of target feature points (e.g., n-target feature points, and the first target feature point is the beginning of the time domain window and the $n^{th}$ target feature point is the end of the time domain window), the electromyographic signal may be divided into (n−1) segments based on the n target feature points. It should be noted that the movement stage corresponding to the target feature point may include one or more types, and a plurality of movement stages corresponding to the target feature point may be used as a benchmark for segmenting the movement signal. For example, the movement stage corresponding to the target feature point may include the movement start point and the movement end point, with the movement start point preceding the movement end point, and the movement signal here between the movement start point and a next movement start point may be considered as a segment of the movement signal.

In some embodiments, the target feature point may include one or more of the movement start point, the movement middle point, or the movement end point.

To describe the segmentation of the movement signal, take the target feature point including all of the movement start point, the movement middle point and the movement end point as an exemplary illustration. The movement start point may be considered as a start point of a user movement cycle. In some embodiments, different movements may correspond to the different preset conditions. For example, in the seated chest press, the preset condition may be that the direction of the angular velocity of the movement after the movement start point changes relative to the direction of the angular velocity of the movement before the movement start point, or that the value of the angular velocity at the movement start point is approximately 0 and the acceleration value of the angular velocity at the movement start point is greater than 0. In other words, when the user performs the seated chest press, the movement starting point may be set to the point when the arms are extended outward horizontally and start to internally rotate. For another example, in a bent-over movement, the preset condition may be that the angle of arm lift is greater than or equal to an angle threshold. Specifically, when the user performs a bent-over movement, the angle of arm lift when the user's arm is horizontal is 0°, the angle of arm lift when the arm is down is negative, and the angle of arm lift when the arm is up is positive. When the user's arm is raised from the horizontal position, the arm is raised at an angle greater than 0. The point in time when the angle of the arm lift reaches the angle threshold may be considered as the movement start point. The angle threshold may be −70° to −20°, or as a preference, the angle threshold may be −50° to −25°. In some embodiments, to further ensure the accuracy of a selected movement start point, the preset condition may also include that the angular velocity of the arm within a specific range of time after the movement start point may be greater than or equal to an angular velocity threshold. The angular velocity threshold may range from 5°/s~50°/s. According to preference of example, the angular velocity threshold may range from 10°/s~30°/s. For example, when a user performs a bent-over movement, the angular velocity of the arm is continuously greater than the angular velocity threshold for a specific time range (e.g., 0.05 s, 0.1 s, 0.5 s) after an angular threshold is reached and the user's arm is continuously raised upward. In some embodiments, if the angular velocity of the selected movement start point according to the preset condition is less than the angular velocity threshold within a specific range of time, the preset condition continues until a movement start point is determined.

In some embodiments, the movement middle point may be a point within one movement cycle from the start point. For example, when the user performs the seated chest press, a start point of the movement may be set to the time when the arms extend outward horizontally and begin to internally rotate, and the time when the arms come together may be used as a movement middle point of the user. In some embodiments, the preset condition may be that a direction of the angular velocity at the point in time after the movement middle point changes relative to a direction of the angular velocity at the point in time before the movement middle point, and an angular velocity value at the movement middle point is approximately zero, wherein the direction of the angular velocity at the movement middle point is opposite to the direction of the angular velocity at the movement start point. In some embodiments, to improve the accuracy of the selection of the movement middle point, a change of the angular velocity (acceleration of angular velocity) in a first specific time range after the movement middle point (e.g., 0.05 s, 0.1 s, 0.5 s) may be greater than an acceleration threshold of angular velocity (e.g., 0.05 rad/s). In some implementations, the amplitude information in the electromyographic signal corresponding to the movement middle point is greater than the electromyographic threshold while the movement middle point satisfies the preset condition described above. Since the different movements correspond to different electromyographic signals, the electromyographic threshold is related to the user movement and the target electromyographic signal. In the seated chest press, the electromyographic signal at the pectoral muscle is the target electromyographic signal. In some embodiments, the position corresponding to the middle point of the movement (also may be called as "middle position") may be approximated as a maximum point of muscle force, where the electromyographic signal may have a relatively great value. It should be noted that the electromyographic signal at the part of the user's body when the user performs the movement during motion is substantially higher than the electromyographic signal at the part of the user's body when the user does not perform the movement during motion (when the muscle in the particular part may be considered as a resting state). For example, an amplitude of the electromyographic signal at the part of the user's body when the user's movement reaches the middle position is 10 times higher than that in the resting state. In addition, the relationship between the amplitude of the electromyographic signal at the part of the user when the movement position reaches the middle position (the movement middle point) and the amplitude of the electromyographic signal in the resting state may be different according to the different movement types performed by the user, and the relationship between the two may be adapted according to the actual movement. In some embodiments, to improve the accuracy of the selection of the movement middle point, the amplitude corresponding to a second specific time range after the movement middle point (e.g., 0.05 s, 0.1 s, 0.5 s) may be continuously greater than the electromyographic threshold. In some embodiments, in addition to the above preset condition (e.g., the angular velocity and an amplitude condition of the electromyographic signal), a Euler angle (also referred to as angle) of the movement middle point and the start position satisfies a certain condition preset to determine the movement middle point. For example, in the seated chest press, the Euler angle at the movement middle point relative to the movement start point may be greater than one or more Euler angle thresholds (also known as angle thresholds). For example, with a front-to-back direction of the human body as an X-axis, a left-right direction of the human body as a Y-axis, and a height direction of the human body as a Z-axis, an Euler angle changed in the X and Y directions may be less than 25°, and the Euler angle changed in the Z direction may be greater than 40° (the movement of the seated chest press is mainly related to the rotation at the Z-axis direction, the above parameters are only reference examples). In some embodiments, the electromyographic thresholds and/or the Euler angle thresholds may be stored in advance in the memory or hard drive of the wearable device 130, or in the processing device 110, or calculated based on an actual condition and adjusted in real time.

In some embodiments, the processing module 220 may determine, based on the time domain window of the electromyographic signal or the attitude signal, the movement middle point from a time domain window at a time point after the movement start point according to a preset condition. In some implementations, after the movement middle point is determined, whether there are other time points that meet the preset condition within the time range from the movement start point to the movement middle point may be re-verified, and if so, a movement start point closest to the movement middle point may be selected as the best movement start point. In some embodiments, if the difference between the time of the movement middle point and the time of the movement start point is greater than a specific time threshold (e.g., ½ or ⅔ of a movement cycle), the movement middle point is invalid, and the movement start point and movement middle point are re-determined based on preset condition.

In some embodiments, the movement end point may be a time point that is within one movement cycle from the movement start point and after the movement middle point. For example, the movement end point may be set to as a point that is one movement cycle from the movement start point, and the movement end point herein may be considered the end of a movement cycle of the user. For example, when the user performs the seated chest press, the movement start point may be set as a time point when the arms extend horizontally to the left and right and start internal rotation, the time point when the arms close together may be the movement middle point of the user, and the time point when the arms return to the extended state again from the horizontal direction may correspond to the movement end point of the user. In some embodiments, the preset condition may be that a changed angular velocity value corresponding to the attitude signal is an extreme value. In some embodiments, to prevent jitter misjudgment, the change in Euler angle should exceed a certain Euler angle threshold, e.g., 20°, in the time range from the movement middle point to the movement end point. In some embodiments, the processing module 220 may determine the movement end point from the time domain window after the movement middle point based on the time domain windows of the electromyographic signal and the attitude signal according to the preset condition. In some embodiments, if the difference between the time of the movement end point and the time of the movement middle point is greater than a specific time threshold (e.g., ½ of a movement cycle), the movement start point and the movement middle point are invalid, and the movement start point, movement middle point, and movement end point are re-determined based on the preset condition.

In some embodiments, at least one set of the movement start point, the movement middle point, and the movement end point in the movement signal may be repeatedly determined, and the movement signal may be segmented based on the at least one set of the movement start point, the movement middle point, and the movement end point as the target feature points. The step may be performed by the processing module 220 and/or the processing device 110. It should be noted that segmentation of the movement signal is not limited to be based on the above movement start point, movement middle point and movement end point, but may also include other time points. For example, for the seated chest press, 5 time points may be selected according to the above steps, a first time point may be a movement start point, a second time point may be a moment of the maximum angular velocity of the internal rotation, a third time point may be the movement middle point, a fourth time point may be the moment of the maximum angular velocity of external rotation, a fifth time point may be the moment when the arms return to extend left and right, and the angular velocity is 0, that is, the movement end point. In this example, compared to the movement start point, movement middle point and movement end point in the above steps, the second time point is added as a ¼ marker point of the movement cycle, the movement end point described in the above embodiments is used as the fourth time point for marking the ¾ position of the movement cycle, and the fifth time point is added as an end point of the complete movement. For the seated chest press, more time points are used here, and a recognition of the movement quality may be done based on the signal of the first ¾ of the movement cycle (i.e., the recognition of the movement quality for a single cycle does not depend on a complete analysis of the signal of a whole cycle), which can complete the monitoring and feedback of the user's movement without the end of a current cycle. At same time, all signals of the process of the whole movement may be completely recorded to be easily uploaded to the cloud or the mobile terminal device, thus more methods may be adopted to monitor the user's movement. For more complex movement, the cycle of the movement may be quite long, and the stages for the movement have different force pattern. In some embodiments, the above method of determining each time point may be adopted to divide the movement into multiple stages, and the signal for each stage may be recognized and fed back separately to improve timeliness of feedback of the user's movement.

It should be noted that the above segmentation and monitoring of the movement signal based on the movement start point, movement middle point and movement end point as a set of target feature point is only an exemplary illustration. In some embodiments, the user's movement signal may also be segmented and monitored based on any one or more of the movement start point, the movement middle point and the movement end point as the target feature point. For example, the movement signal may be segmented and monitored by using the movement start point as the target feature point. For another example, the movement start point and the movement end point may be used as a set of target feature points to segment and monitor the movement signal, and other time point or time ranges that can be used as the target feature point are within the scope of protection of the present disclosure.

It should be noted that the above description of the process 700 is for example and illustration purposes only and does not limit the scope of application of the present disclosure. For those skilled in the art, various amendments and changes can be made to the process 700 under the guidance of the present disclosure. However, these amendments and changes remain within the scope of the present disclosure. For example, step 710 and step 720 may be performed simultaneously in the processing module 220. For another example, step 710 and step 720 may be performed simultaneously in the processing module 220 and the processing device 110, respectively.

Figure 8:
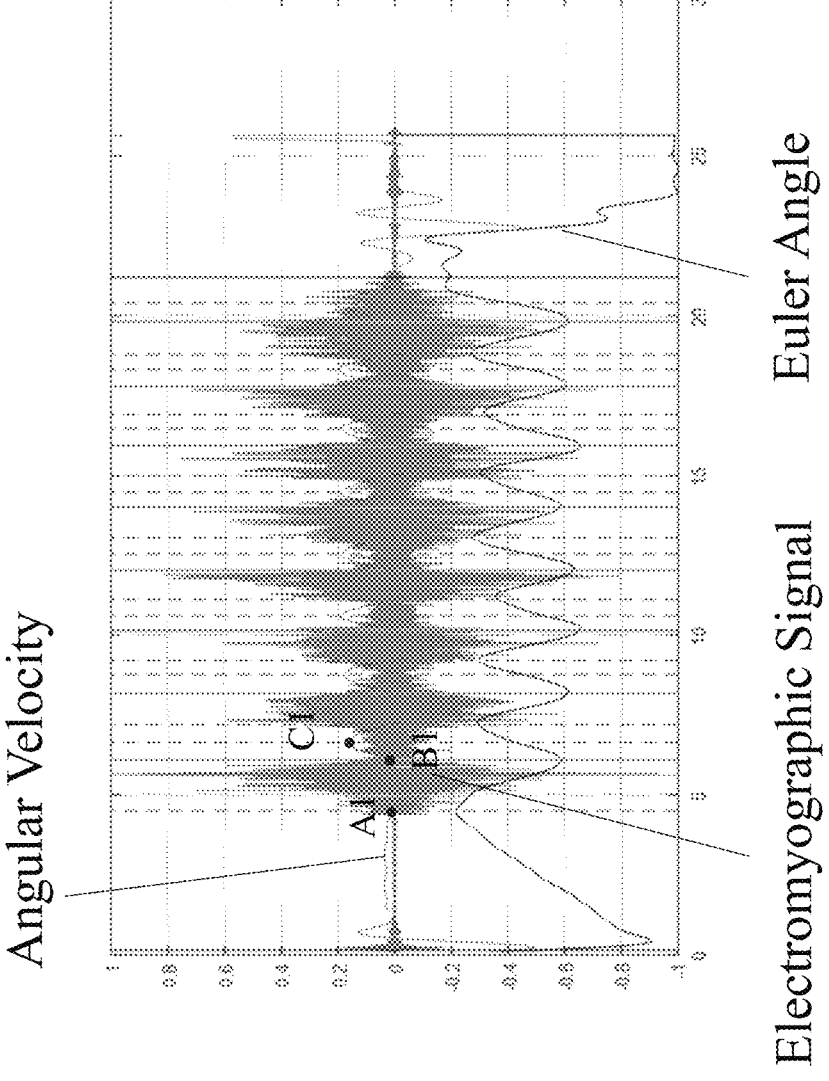
FIG. 8 is a diagram illustrating exemplary normalized results of segmenting a movement according to some embodiments of the present disclosure.

FIG. 8 is a diagram illustrating exemplary movement signal segmentation according to some embodiments of the present disclosure. A horizontal coordinate in FIG. 8 may indicate a motion time of a user, and a vertical coordinate may indicate amplitude information of an electromyographic signal of a muscle part (e.g., pectoralis major) during seated chest press. Also included in FIG. 8 are an angular velocity curve and a Euler angle curve corresponding to an attitude signal of the wrist position of the user during motion. The angular velocity curve is configured to represent a velocity change of the user during motion and the Euler angle curve is configured to represent a position situation of a user's body part during motion. As shown in FIG. 8, point A1 is determined as the movement start point according to the preset condition. Specifically, a direction of the angular velocity at a time point after the user's movement start point A1 changes relative to the direction of the angular velocity at a time point before the movement start point A1. Further, the angular velocity value at the movement start point A1 is approximately 0, and an acceleration value of the angular velocity at the movement start point A1 is greater than 0.

Refer to FIG. 8, point B1 is determined as the movement middle point according to the preset condition. Specifically, the direction of the angular velocity at the time point after the user's movement middle point B1 changes relative to the direction of the angular velocity at the time point before the movement middle point B1, and the angular velocity value at the movement middle point B1 is approximately 0. The direction of the angular velocity at the movement middle point B1 is opposite to the direction of the angular velocity at the movement start point A1. In addition, the amplitude of the electromyographic signal (shown as the "electromyographic signal" in FIG. 8) corresponding to the movement middle point B1 is greater than the electromyographic threshold.

Continue to refer to FIG. 8, point C1 is determined as the movement end point according to the preset condition. Specifically, a changed angular velocity value at the movement end point C1 is the extreme value from the movement start point A1 to the movement end point C1. In some embodiments, the process 700 may complete the movement segmentation shown in FIG. 8, such that the movement signal from the movement start point A1 to the movement end point C1 shown in FIG. 8 may be considered as a segment of the motion.

It is noted that in some embodiments, if a time interval between the movement middle point and the movement start point is greater than a specific time threshold (e.g., ½ of a movement cycle), the processing module 220 may re-determine the movement start point to improve the accuracy of the movement segmentation. The specific time threshold here may be stored in the memory or the hard drive of the wearable device 130, or in the processing device 110, or calculated or adjusted based on the actual situation of the user during motion. For example, if the time interval between the movement start point A1 and the movement middle point B1 in FIG. 8 is greater than a specific time threshold, the processing module 220 may re-determine the movement start point, thereby improving the accuracy of the movement segmentation. In addition, the segmentation of the movement signal is not limited to be based on the above movement start point A1, movement middle point B1 and movement end point C1, but may also include other time points, and selection of the time points may be made according to complexity of the movement.

When obtaining the user's movement signal, other physiological parameter information of the user (e.g., a heart rate signal), external condition such as a relative movement of the obtaining module 210 and the human body during motion or compression of the obtaining module 210 may affect the quality of the movement signal, for example, resulting in an abrupt change in the electromyographic signal, thereby affecting the monitoring of the movement. For ease of description, an abrupt electromyographic signal may be described by using a singularity, and an exemplary singularity may include a burr signal, a discontinuous signal, etc. In some embodiments, monitoring the movement of the user during motion based at least on the feature information corresponding to the electromyographic signal or the feature information corresponding to the attitude signal may further include: pre-processing the electromyographic signal in a frequency domain or a time domain, obtaining, based on the pre-processed electromyographic signal, the feature information corresponding to the electromyographic signal, and monitoring, based on the feature information corresponding to the electromyographic signal or the feature information corresponding to the attitude signal, the movement of the user during motion. In some embodiments, pre-processing the electromyographic signal in the frequency domain or the time domain may include filtering the electromyographic signal in the frequency domain to select or retain components of the electromyographic signal in a particular frequency range in the frequency domain. In some embodiments, the obtaining module 210 may obtain an electromyographic signal in a frequency range of 1 Hz-1000 Hz, filter the electromyographic signal and select an electromyographic signal in a specific frequency range (e.g., 30 Hz-150 Hz) for subsequent processing. In some embodiments, the specific frequency range may be 10 Hz-500 Hz. According to preference of example, the specific frequency range may be 15 Hz-300 Hz or 30 Hz-150 Hz. In some embodiments, a filtering process may include a low-pass filter processing. In some embodiments, the low-pass filter may include an LC passive filter, an RC passive filter, an RC active filter, a passive filter composed of special elements. In some embodiments, the passive filter composed of the special elements may include one or more of a piezoelectric ceramic filter, a crystal filter, and an acoustic surface filter. It should be noted that the specific frequency range is not limited to the above range, but may also be other ranges, which may be selected according to the actual situation. More descriptions of monitoring, according to the feature information corresponding to the electromyographic signal or the feature information corresponding to the attitude signal, the movement of the user during motion may be found in FIG. 5, FIG. 6 of the present disclosure and their relevant descriptions.

In some embodiments, pre-processing the electromyographic signal in the frequency domain or the time domain may further include signal correction processing of the electromyographic signal in the time domain. The signal correction processing refers to a correction to the singularity (e.g., the burr signal, the discontinuous signal, etc.) in the electromyographic signal. In some embodiments, the signal correction processing of the electromyographic signal in the time domain may include determining the singularity in the electromyographic signal, i.e., determining the abrupt signal in the electromyographic signal. The singularity may be a sudden change in the amplitude of an electromyographic signal within a certain moment, causing a discontinuity in the signal. For another example, the electromyographic signal is morphologically smooth and there is no abrupt change in the amplitude of the electromyographic signal, but there is the abrupt change in the first-order differential of the electromyographic signal, and the first-order differential is discontinuous. In some embodiments, the method of determining the singularity in the electromyographic signal may include, but is not limited to, one or more of Fourier transform, wavelet transform, fractal dimension, etc. In some embodiments, the signal correction processing of the electromyographic signal in the time domain may include removing the singularity in the electromyographic signal, for example, removing signals within a period of time at and near the singularity. Alternatively, the signal correction processing of the electromyographic signal in the time domain may include correcting the singularity of the electromyographic signal according to the feature information of the electromyographic signal in the specific time range, such as adjusting the amplitude of the singularity based on the signals around the singularity. In some embodiments, the feature information of the electromyographic signal may include the amplitude information, the statistic information of the amplitude information, etc. The statistic information of amplitude information (also known as amplitude entropy) refers to a distribution of the amplitude information of the electromyographic signal in the time domain. In some embodiments, after a location (e.g., the time point) of the singularity in the electromyographic signal is determined through a signal processing algorithm (e.g., the Fourier transform, the wavelet transform, the fractal dimension), the singularity may be corrected based on the electromyographic signal in the specific time range before or after the location of the singularity. For example, when the singularity is an abrupt trough, the electromyographic signal at the abrupt trough can be supplemented based on the feature information (e.g., the amplitude information, the statistic information of the amplitude information) of the electromyographic signal in a specific time range (e.g., 5 ms-60 ms) before or after the abrupt trough.

Exemplary illustration with the singularity as the burr signal, FIG. 9 is a flowchart of an exemplary process for pre-processing an electromyographic signal according to some embodiments of the present disclosure. As shown in FIG. 9, the process 900 may include:

Step 910, selecting, based on the time domain window of the electromyographic signal, different time windows from the time domain window of the electromyographic signal, wherein the different time windows respectively cover different time ranges.

In some embodiments, the step may be performed by the processing module 220 and/or the processing device 110. In some embodiments, the different windows may include at least one specific window. A specific window is a window with a specific time length selected from the time domain window. For example, a time length of the specific window may be 100 ms when the time length of the time domain window of the electromyographic signal is 3 s. In some embodiments, a specific window may include a plurality of different time windows. Merely as way of exemplary illustration, the specific window may include a first time window and a second time window, and the first time window may refer to a window corresponding to a partial time length of the specific window, for example, when the time length of the specific window is 100 ms, the time length of the first time window may be 80 ms. The second time window may be another window corresponding to the partial time length of the specific window. For example, when the specific window is 100 ms, the second time window may be 20 ms. In some embodiments, the first time window and the second time window may be consecutive time windows within a same specific window. In some embodiments, the first time window and the second time window may also be two discrete or overlapping time windows within the same specific window. For example, when the time length of the specific window is 100 ms, the time length of the first time window may be 80 ms and the time length of the second time window may be 25 ms, in which case the second time window is overlapped with the first time window in 5 ms. In some embodiments, the processing module 220 may slide and update the specific window sequentially from an initially time point of the time domain window of the electromyographic signal according to the specific time length based on the time domain window of the electromyographic signal, and may continue to divide an updated specific window into the first time window and the second time window. The specific time length mentioned here may be less than 1 s, 2 s, 3 s, etc. For example, the processing module 220 may select a specific window of a specific time length of 100 ms and divide that specific window into a first time window of 80 ms and a second time window of 20 ms. Further, the specific window may be updated by sliding along the time direction. A sliding distance here may be a time length of the second time window (e.g., 20 ms) or other suitable time lengths, e.g., 30 ms, 40 ms, etc.

Step 920, determining, based on the feature information corresponding to the electromyographic signal in the different time windows, the burr signal.

In some embodiments, the step may be performed by the processing module 220 and/or the processing device 110. In some embodiments, the feature information corresponding to the electromyographic signal may include at least one of the amplitude information, the statistic information of the amplitude information. In some embodiments, the processing module 220 may obtain the amplitude information or the statistic information of the amplitude information corresponding to the electromyographic signal in different time windows (e.g., the first time window, the second time window) to determine the location of the burr signal. Detailed descriptions of determining, based on the feature information corresponding to the electromyographic signal in different time windows, the location of the burr signal may be found in FIG. 10 and its relevant descriptions.

It should be noted that the above description of the process 900 is for example and illustration purposes only and does not limit the scope of application of the present disclosure. For those skilled in the art, various amendments and changes can be made to process 900 under the guidance of the present disclosure. For example, the specific window is not limited to include the first time window and the second time window described above, but may also include other time windows, for example, a third time window, a fourth time window, etc. In addition, the specific range of moments before or after the position of the burr signal may be adapted according to the length of the burr signal, which will not be further limited herein. However, these amendments and changes remain within the scope of the present disclosure.

Figure 10:
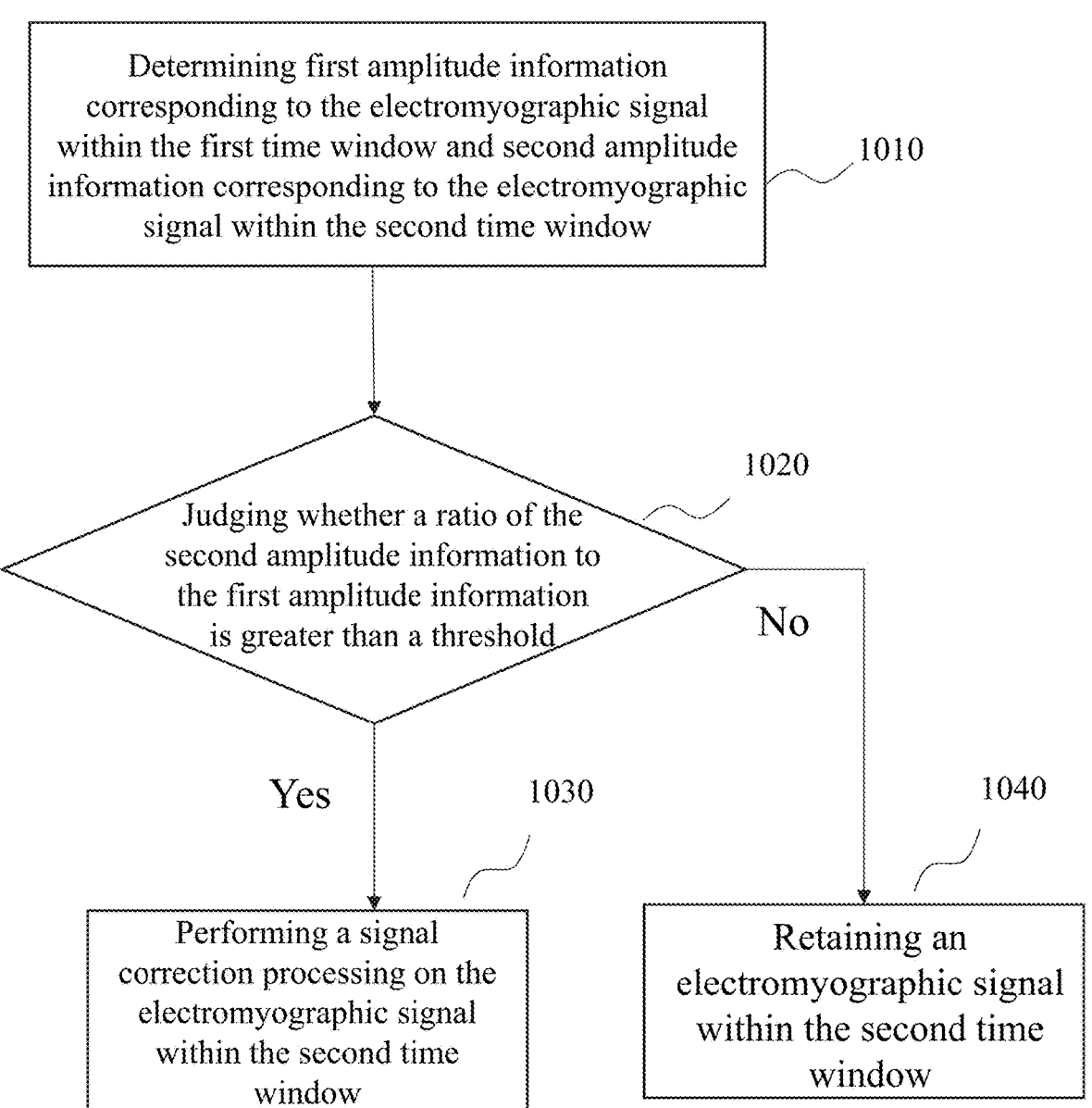
FIG. 10 is a flow chart illustrating an exemplary burr signal according to some embodiments of the present disclosure.

FIG. 10 is a flow chart illustrating an exemplary process for determining a burr signal according to some embodiments of the present disclosure.

Step 1010, determining first amplitude information corresponding to the electromyographic signal within the first time window and second amplitude information corresponding to the electromyographic signal within the second time window.

In some embodiments, the step may be performed by the processing module 220 and/or the processing device 110. In some embodiments, the processing module 220 may select the time length of the first time window and the second time window and extract the first amplitude information corresponding to the electromyographic signal during the time length of the first time window and the second amplitude information corresponding to the electromyographic signal during the time length of the second time window. In some embodiments, the first amplitude information may include an average amplitude of the electromyographic signal during the first time window, and the second amplitude information may include the average amplitude of the electromyographic signal during the second time window. For example, the processing module 220 may select a time length of a first time window as 80 ms and extract the first amplitude information corresponding to the electromyographic signal within the first time window, and the processing module 220 may select a time length of a second time window as 20 ms and extract the second amplitude information corresponding to the electromyographic signal within the second time window.

In some embodiments, a selection of the time length of the first time window and the time length of the second time window is related to the shortest burr signal length and amount of computation of the system. In some embodiments, the time length of the first time window and the time length of the second time window may be selected according to the feature of the burr signal. The time length of an electro-cardio burr signal is 40 ms-100 ms, the time interval between two burr signals in the electro-cardio signal may be about 1 s, a peak point of the burr signal is basically symmetrical on both sides, an amplitude distribution of the burr signal is relatively even on both sides, etc. In some embodiments, when the burr signal is the electro-cardio signal, a time length less than the length of the burr signal, e.g., half the length of the burr signal, may be selected as the time length of the second time window, and the time length of the first time window may be greater than (e.g., four times) the time length of the second time window. In some embodiments, the time length of the first time window may be within a range of an interval (about 1 s) between burr signals minus the time length of the second time window. It should also be noted that the above selected time length of the first time window and the time length of the second time window are not limited to the above description, as long as a sum of the time length of the second time window and the time length of the first time window is less than time intervals of adjacent two burr signals, or the time length of the second time window is less than the single burr signal length, or an amplitude of the electromyographic signal within the second time window and an amplitude of the electromyographic signal the first time window may be discriminated.

Step 1020, judging whether a ratio of the second amplitude information to the first amplitude information is greater than a threshold.

In some embodiments, the step may be performed by the processing module 220 and/or the processing device 110. In some embodiments, the processing module 220 may determine whether the ratio of the second amplitude information corresponding to the electromyographic signal in the second time window to the first amplitude information corresponding to the electromyographic signal in the first time window is greater than the threshold. The threshold here may be stored in the memory or the hard drive of the wearable device 130, or in the processing device 110, or adjusted according to the actual situation. In some embodiments, the step 1020 may proceed to step 1030 if the processing module 220 judges that the ratio of the second amplitude information to the first amplitude information is greater than the threshold. In other embodiments, if the processing module 220 determines that the ratio of the second amplitude information to the first amplitude information is not greater than the threshold, step 1020 may proceed to step 1040.

Step 1030, performing a signal correction processing on the electromyographic signal within the second time window.

In some embodiments, the step may be performed by the processing module 220 and/or the processing device 110. In some embodiments, the processing module 220 may perform the signal correction processing on the electromyographic signal within the second time window based on the comparison result of the ratio of the second amplitude information to the first amplitude information and the threshold in step 1020. For example, in some embodiments, if the ratio of the second amplitude information to the first amplitude information is greater than the threshold, then the electromyographic signal in the second time window corresponding to the second amplitude information is a burr signal. In some embodiments, processing the electromyographic signal within the second time window may include performing signal correction processing on the electromyographic signal within the second time window based on the electromyographic signal within a specific time range before or after the second time window. In some embodiments, the signal correction processing of the electromyographic signal within the second time window may include, but is not limited to, padding, interpolation, etc. In some embodiments, the specific time range herein may be 5 ms-60 ms. According to preference of example, the specific time range may be 10 ms-50 ms or 20 ms-40 ms. It should be noted that the specific time range is not limited to the above range, for example, the specific time range may be greater than 60 ms, less than 5 ms, or other ranges. In practical application scenarios, the specific time range may be adapted based on the duration of the burr signal.

In step 1040, retaining an electromyographic signal within the second time window.

In some embodiments, the step may be performed by the processing module 220 and/or the processing device 110. In some embodiments, the processing module 220 may perform retention on the electromyographic signal within the second time window according to the comparison result of the ratio of the second amplitude information to the first amplitude information and the threshold in step 1020. For example, in some embodiments, the ratio of the second amplitude information to the first amplitude information is not greater than the threshold, then the electromyographic signal within the second time window corresponding to the second amplitude information is a normal electromyographic signal, and the normal electromyographic signal may be retained, i.e., the electromyographic signal within the second time window is retained.

It should be noted that the amplitude of the electromyographic signal is gradually increasing since electrical charges gradually accumulates during muscular exertion, so that the amplitude of the electromyographic signal within two adjacent time windows (e.g., the first time window and the second time window) does not change abruptly in the absence of a burr signal. In some embodiments, whether there is the burr signal in the electromyographic signal may be determined and the burr signal may be removed based on the process 1000 to realize a real-time processing of the burr signal, thereby enabling the wearable device 130 or the mobile terminal device 140 to provide a real-time feedback of the motion state to the user, and helping the user to perform motion more scientifically.

In some embodiments, the time length corresponding to the first time window may be greater than the time length corresponding to the second time window. In some embodiments, a specific time length corresponding to a specific window may be less than 1 s. In some embodiments, the ratio of the time length corresponding to the first time window to the time length corresponding to the second time window may be greater than 2. In some embodiments, the time length corresponding to the first time window, the time length corresponding to the second time window, and the specific time length corresponding to the specific window are selected to ensure that the shortest burr signal (e.g., 40 ms) can be removed, and the system has a high signal-to-noise ratio, calculation volume of the system can be decreased, repeated calculation of the system can be avoided, the time complexity can be reduced, thereby improving calculation efficiency and calculation accuracy of the system.

It should be noted that the above description of the process 1000 is for example and illustration purposes only, and does not limit the scope of application of the present disclosure. For those skilled in the art, various amendments and changes may be made to process 1000 under the guidance of the present disclosure. For example, the above process 1000 is only an example where the singularity is the burr signal, and when the singularity is a trough signal, each of the above steps (e.g., step 1010, step 1020, step 1030, etc.) and the technical schemes may be adjusted or other methods may be used to perform signal correction processing. However, these amendments and changes remain within the scope of the present disclosure.

In some embodiments, the signal correction processing on the singularity of the electromyographic signal may further be performed by the other methods, e.g., a high-pass method, a low-pass method, a band-pass method, a wavelet transform reconstruction method, etc. In some embodiments, for an application scenario where a low-frequency signal is not sensitive, a 100 Hz high-pass filter may be used for a removal of the burr signal. In some embodiments, in addition to the signal correction processing of the electromyographic signal, the other methods of the signal processing of the electromyographic signal, such as a filtering processing, a signal amplification, a phase adjustment, etc., may also be performed. In some embodiments, the electromyographic signal of the user collected by the electromyographic sensor may be converted into a digital electromyographic signal by an analog-to-digital converter (ADC), and the converted digital electromyographic signal may be subjected to a filtering process, which can filter out an industrial frequency signal and its harmonic signal, etc. In some embodiments, the processing of the electromyographic signal may further include removing motion artifacts of the user. The motion artifacts here refer to signal noise generated by a relative movement of the muscles at the position to be measured relative to the electromyographic module during an obtaining process of the electromyographic signal while the user in motion.

In some embodiments, the attitude signal may be obtained by the attitude sensor on the wearable device 130. The attitude sensor on the wearable device 130 may be distributed on the limb areas (e.g., arms, legs, etc.), the trunk areas (e.g., chest, abdomen, back, waist, etc.), and the head, etc. The attitude sensor enables the collection of the attitude signal from other parts of the body such as limb parts and trunk parts. In some embodiments, the attitude sensor may be a sensor of an Attitude and heading reference system (AHRS) with an attitude fusion algorithm. The attitude fusion algorithm may fuse data from a nine-axis inertial measurement unit (IMU) with a three-axis acceleration sensor, a three-axis angular velocity sensor, and a three-axis geomagnetic sensor into Euler angles or quaternions to obtain the attitude signal of the user's body part where the attitude sensor is located. In some embodiments, the processing module 220 and/or the processing device 110 may determine the feature information corresponding to the attitude based on the attitude signal. In some embodiments, the feature information corresponding to the attitude signal may include, but is not limited to, the angular velocity value, the direction of angular velocity, the acceleration value of angular velocity, etc. In some embodiments, the attitude sensor may be a strain sensor, and the strain sensor may obtain a bending direction and bending angle at the user's joints, thereby obtaining the attitude signal during the user's motion. For example, the strain sensor may be set at the knee joint of the user, and when the user is in motion, the user's body part acts on the strain sensor, and the bending direction and the bending angle at the knee joint of the user may be calculated based on the change in resistance or length of the strain sensor, thereby obtaining the attitude signal of the user's leg. In some embodiments, the attitude sensor may also include a fiber optic sensor, and the attitude signal may be represented by a change in direction after bending of a fiber from the fiber optic sensor. In some embodiments, the attitude sensor may also be a magnetic flux sensor, and the attitude signal may be represented by transformation of the magnetic flux. It should be noted that the type of attitude sensor is not limited to the above sensors, but can also be other sensors, the sensors that can obtain the user's attitude signal are within the scope of the attitude sensor of the present disclosure.

FIG. 11 is a flowchart of an exemplary process for determining feature information corresponding to an attitude signal according to some embodiments of the present disclosure. As shown in FIG. 11, the process 1100 may include:

Step 1110, obtaining a target coordinate system and a conversion relationship between the target coordinate system and at least one original coordinate system.

In some embodiments, the step may be performed by the processing module 220 and/or the processing device 110. In some embodiments, the original coordinate system is a coordinate system corresponding to the attitude sensor set on the human body. When the user uses the wearable device 130, each attitude sensor on the wearable device 130 is distributed on different parts of the human body, so that installation angles of the attitude sensors are different, and the attitude sensors in different parts use their own coordinate systems as the original coordinate systems, so the attitude sensors in different parts have different original coordinate systems. In some embodiments, an obtained attitude signal of the each attitude sensor may be represented in its corresponding original coordinate system. By transforming the attitude signal in different original coordinate systems into a same coordinate system (e.g., the target coordinate system), it is easy to determine relative motion between different parts of the human body. In some embodiments, the target coordinate system refers to a human coordinate system established based on the human body. For example, a length direction of the human torso (i.e., a direction perpendicular to a transverse plane of the body) can be used as the Z-axis, an anterior-posterior direction of the human torso (i.e., the direction perpendicular to the coronal plane of the body) as the X-axis, and the left-right direction of the human torso (i.e., the direction perpendicular to the sagittal plane of the body) as the Y-axis in the target coordinate system. In some embodiments, there is a conversion relationship between the target coordinate system and the original coordinate system by which the coordinate information in the original coordinate system can be converted to the coordinate information in the target coordinate system. In some embodiments, the conversion relationship may be expressed as one or more rotation matrices. More descriptions of determining the conversion relationship between the target coordinate system and the original coordinate system may be found in FIG. 13 of the present disclosure and its relevant descriptions.

Step 1120, converting, based on the conversion relationship, the coordinate information in the at least one original coordinate system to the coordinate information in the target coordinate system.

In some embodiments, the step may be performed by the processing module 220 and/or the processing device 110. The coordinate information in the original coordinate system is three-dimensional coordinate information in the original coordinate system. The coordinate information in the target coordinate system is the three-dimensional coordinate information in the target coordinate system. Merely as way of exemplary illustration, the coordinate information $v_1$ in the original coordinate system may be converted to the coordinate information $v_2$ in the target coordinate system according to the conversion relationship. Specifically, a conversion between the coordinate information $v_1$ and the coordinate information $v_2$ may be performed by using a rotation matrix, the rotation matrix here can be understood as the conversion relationship between the original coordinate system and the target coordinate system. Specifically, the coordinate information $v_1$ in the original coordinate system may be converted to coordinate information $v_1-1$ by a first rotation matrix, the coordinate information $v_1-1$ may be converted to coordinate information $v_1-2$ by a second rotation matrix, and the coordinate information $v_1-2$ may be converted to coordinate information $v_1-3$ by a third rotation matrix. The coordinate information $v_1-3$ is the coordinate information $v_2$ in the target coordinate system. It should be noted that the rotation matrices are not limited to the above first rotation matrix, the second rotation matrix and the third rotation matrix, but may also include fewer or more rotation matrices. In some alternative embodiments, the rotation matrix may be a rotation matrix or a combination of a plurality of rotation matrices.

Step 1130, determining, based on the coordinate information in the target coordinate system, the feature information corresponding to the attitude signal.

In some embodiments, the step may be performed by the processing module 220 and/or the processing device 110. In some embodiments, determining, based on the coordinate information in the target coordinate system, the feature information corresponding to the attitude signal comprises determining based on a plurality of coordinate information in the target coordinate system of the user during motion, the feature information corresponding to the attitude signal of the user. For example, when the user performs a seated chest press, the user's arm may correspond to the first coordinate information in the target coordinate system when the user's arm is held forward, and the user's arm can correspond to the second coordinate information in the target coordinate system when the user's arm is opened in a same plane as the torso. Based on the first coordinate information and the second coordinate information, the feature information (for example, the angular velocity, the angular velocity direction, and the acceleration value of the angular velocity) corresponding to the attitude signal may be calculated.

It should be noted that the above description of the process 1100 is for example and illustration purposes only and does not limit the scope of application of the present disclosure. For those skilled in the art, various amendments and changes can be made to process 1100 under the guidance of the present disclosure. However, these amendments and changes remain within the scope of the present disclosure.

In some embodiments, the relative motion between different motion parts of the user's body may be determined by the feature information corresponding to the attitude sensors located at the different motion parts of the user's body. For example, by using the feature information corresponding to the attitude sensor at the user's arm and the feature information corresponding to the attitude sensor at the user's torso, the relative motion between the user's arm and torso during motion can be determined. FIG. 12 is a flowchart of an exemplary process for determining relative motion between the different motion parts of the user according to some embodiments of the present disclosure. As shown in FIG. 12, the process 1200 may include:

Step 1210, determining, based on the conversion relationships between the different original coordinate systems and the target coordinate system, the feature information corresponding to at least two sensors respectively.

In some embodiments, the step may be performed by the processing module 220 and/or the processing device 110. In some embodiments, different sensors have different conversion relationships between the original coordinate systems corresponding to the sensors and the target coordinate system due to the different installation positions at the human body. In some embodiments, the processing device 110 may convert the coordinate information in the original coordinate systems corresponding to the sensors of different parts of the user (e.g., small arm, large arm, torso, etc.) to the coordinate information in the target coordinate system, respectively, so that the feature information corresponding to at least two sensors can be determined respectively. More descriptions of the conversion of the coordinate information in the original coordinate system to coordinate information in the target coordinate system may be found elsewhere in the present disclosure, e.g., FIG. 11, which will not be repeated herein.

Step 1220, determining, based on the feature information corresponding to the at least two sensors respectively, the relative motion between the different motion parts.

In some embodiments, the step may be performed by the processing module 220 and/or the processing device 110. In some embodiments, a motion part may refer to a limb on the human body that can move independently, for example, a small arm, a large arm, a small leg, a thigh, etc. Merely as way of exemplary illustration, when the user performs an arm lifting dumbbell, the coordinate information in the target coordinate system corresponding to the sensor set at the small arm part and the coordinate information in the target coordinate system corresponding to the sensor set at the large arm part are combined to determine the relative motion between the small arm and the large arm of the user, thereby determining the arm lifting dumbbell movement of the user.

In some embodiments, a same motion part of the user may be arranged with a plurality of sensors of the same or different types, and the coordinate information in the original coordinate systems corresponding to a plurality of sensors of same or different types may be converted to the coordinate information in the target coordinate system, respectively. For example, a plurality of sensors of the same or different types can be arranged at different locations of the user's small arm part, and a plurality of coordinates in the target coordinate system corresponding to a plurality of sensors of the same or different types may simultaneously represent the movement of the user's small arm part. For example, the coordinate information in the target coordinate systems corresponding to a plurality of sensors of the same type can be averaged, thereby improving the accuracy of the coordinate information of the motion parts during the user's motion. For example, the coordinate information in the target coordinate system can be obtained by performing a fusion algorithm (e.g., Kalman filtering, etc.) on the coordinate information in coordinate systems corresponding to a plurality of the different types of sensors.

It should be noted that the above description of the process 1100 is for example and illustration purposes only and does not limit the scope of application of the present disclosure. For those skilled in the art, various amendments and changes can be made to process 1100 under the guidance of the present disclosure. However, these amendments and changes remain within the scope of the present disclosure.

Figure 13:
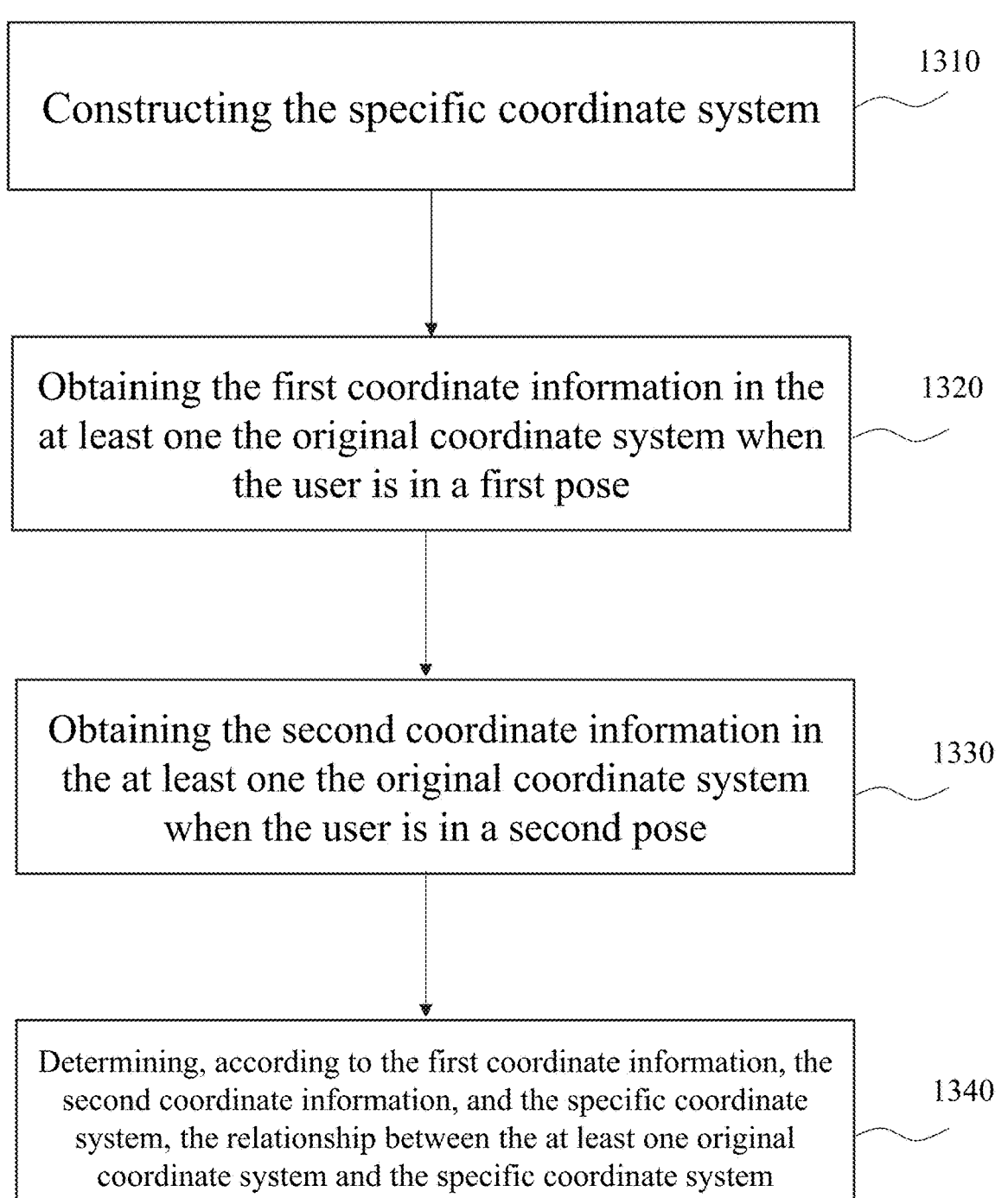
FIG. 13 is a flowchart of an exemplary process for determining a conversion relationship between an original coordinate system to a particular coordinate system according to some embodiments of the present disclosure.

FIG. 13 is a flowchart of an exemplary process for determining a conversion relationship between an original coordinate system to a specific coordinate system according to some embodiments of the present disclosure. In some embodiments, the process of determining the conversion relationship between the original coordinate system to a specific coordinate system may also be called a calibration process. As shown in FIG. 13, the process 1300 may include:

Step 1310, constructing the specific coordinate system.

In some embodiments, the step may be performed by the processing module 220 and/or the processing device 110. In some embodiments, the conversion relationship between at least one original coordinate system and the target coordinate system may be obtained by the calibration process. The specific coordinate system is a reference coordinate system configured to determine the conversion relationship between the original coordinate system and the target coordinate system during the calibration process. In some embodiments, a constructed specific coordinate system may have the length direction of the torso when the human body is standing as the Z-axis, the front-to-back direction of the human body as the X-axis, and the left-to-right direction of the human torso as the Y-axis. In some embodiments, the specific coordinate system is related to the orientation of the user during the calibration process. For example, if the user's body is facing a fixed direction (e.g., north) during the calibration process, the direction in front of the body (north) is the X-axis.

Step 1320, obtaining the first coordinate information in the at least one original coordinate system when the user is in a first pose.

In some embodiments, the step may be performed by the obtaining module 210. The first pose may be a pose that the user approximately remains standing. The obtaining module 210 (e.g., the sensor) may obtain the first coordinate information in the original coordinate system based on the user's first pose.

Step 1330, obtaining the second coordinate information in the at least one original coordinate system when the user is in a second pose.

In some embodiments, the step may be performed by the obtaining module 210. The second pose may be a pose that the user's body part (e.g., arm) where the sensor is located is tilted forward. In some embodiments, the obtaining module 210 (e.g., the sensor) may obtain the second coordinate information in the original coordinate system based on the user's second pose (e.g., a forward leaning pose).

Step 1340, determining, according to the first coordinate information, the second coordinate information, and the specific coordinate system, the relationship between the at least one original coordinate system and the specific coordinate system.

In some embodiments, the step may be performed by the processing module 220 and/or processing device 110. In some embodiments, the first rotation matrix may be determined through the first coordinate information corresponding to the first pose. In the first pose, since the Euler angle in a X and Y direction of the specific coordinate system in a ZYX rotation order are 0, and the Euler angle in the X and Y direction of the original coordinate system is not necessarily 0, then the first rotation matrix is the rotation matrix obtained by reversing the original coordinate system around the X-axis and then around the Y-axis. In some embodiments, the second rotation matrix may be determined through the second coordinate information of the second pose (e.g., the body part where the sensor is located is tilted forward). Specifically, in the second pose, it is known that the Euler angle of the specific coordinate system in a Y and $Z_3$ direction is 0 under the ZYZ rotation order, and the Euler angle of the original coordinate system in a Y and $Z_3$ direction is not necessarily 0, then the second rotation matrix is the rotation matrix obtained by reversing the original coordinate system around the Y direction and then around the $Z_3$ direction. The conversion relationship between the original coordinate system and the specific coordinate system may be determined through the above first rotation matrix and second rotation matrix. In some embodiments, when there are a plurality of original coordinate systems (sensors), the above method may be configured to determine the conversion relationship between each original coordinate system and the specific coordinate system.

It should be noted that the above first pose is not limited to an approximately standing pose, and the second pose is not limited to the pose that the user's body part (e.g., arm) where the sensor is located is tilted forward, the first and second poses herein may be approximated as being stationary during the calibration process. In some embodiments, the first pose and/or the second pose may also be a dynamic pose during the calibration process. For example, the user's walking attitude is a relatively fixed attitude, the angle and angular velocity of the arms, legs and feet during walking can be extracted to recognize the movement, such as forward stride, forward arm swing and the like, and the user's forward walking attitude can be used as the second pose in the calibration process. In some embodiments, the second pose is not limited to one movement, but a plurality of movements can also be extracted as the second pose. For example, the coordinate information of a plurality of movements may be fused to obtain a more accurate rotation matrix.

In some embodiments, the rotation matrix may be dynamically corrected during the calibration process by using some signal processing algorithms (e.g., using Kalman filtering algorithm) to obtain a better transformation matrix throughout the calibration process.

In some embodiments, machine learning algorithms, or other algorithms may be configured for automatic recognition of some specific movements to update the rotation matrix in real time. For example, if the machine learning algorithm recognizes that a current user is walking, or standing, the calibration process is automatically started. In this case, the wearable device does not need an explicit calibration process anymore, and the rotation matrix is dynamically updated when the user uses the wearable device.

In some embodiments, the installation position of the attitude sensor may be relatively fixed and a rotation matrix may be preset, which can make the recognition process of the specific movement more accurate. Further, the rotation matrix continues to be corrected as the user using the wearable device, so that an obtained rotation matrix is closer to the real situation.

It should be noted that the above description of the process 1300 is for example and illustration purposes only, and does not limit the scope of application of the present disclosure. For those skilled in the art, various amendments and changes can be made to process 1300 under the guidance of the present disclosure. However, these amendments and changes remain within the scope of the present disclosure.

FIG. 14 is a flowchart of an exemplary process for determining a conversion relationship between an original coordinate system and a target coordinate system according to some embodiments of the present disclosure. As shown in FIG. 14, the process 1400 may include:

Step 1410, obtaining the conversion relationship between the specific coordinate system and the target coordinate system.

In some embodiments, the step may be performed by the processing module 220 and/or the processing device 110. Both the specific coordinate system and the target coordinate system take the length direction of the human torso as the Z-axis, so that through the conversion relationship between the X-axis of the specific coordinate system and the X-axis of the target coordinate system and the conversion relationship between the Y-axis of the specific coordinate system and the Y-axis of the target coordinate system, the conversion relationship between the specific coordinate relationship and the target coordinate system can be obtained. The principle of obtaining the conversion relationship between the specific coordinate relationship and the target coordinate system may be found in FIG. 13 and its relevant descriptions.

In some embodiments, the specific coordinate system may take the length direction of the human torso as the Z-axis and a front-to-back direction of the human body as a calibrated X-axis. Since the front-to-back direction of the user's body changes during motion (e.g., a turning movement) and cannot be fixed in the calibrated coordinate system, it is necessary to determine the coordinate system that can rotate with the body, i.e., the target coordinate system. In some embodiments, the target coordinate system may change as the user's orientation changes, with the X-axis of the target coordinate system always being directly in front of the human torso.

Step 1420, determining, according to the conversion relationship between the at least one original coordinate system and the specific coordinate system, and the conversion relationship between the specific coordinate system and the target coordinate system, the conversion relationship between the at least one original coordinate system and the target coordinate system.

In some embodiments, the step may be performed by the processing module 220 and/or the processing device 110. In some embodiments, the processing device 110 may determine the conversion relationship between the at least one original coordinate system and the target coordinate system according to the conversion relationship between the at least one original coordinate system and the specific coordinate system determined in the process 1300 and the conversion relationship between the specific coordinate system and the target coordinate system determined in step 1410, such that the coordinate information in the original coordinate system may be converted to the target coordinate information in the target coordinate system.

It should be noted that the above description of the process 1400 is for example and illustration purposes only and does not limit the scope of application of the present disclosure. For those skilled in the art, various amendments and changes can be made to the process 1400 under the guidance of the present disclosure. However, these amendments and changes remain within the scope of the present disclosure.

In some embodiments, the position of the attitude sensors set on the wearable device 130 may change and/or the attitude sensors may be installed at different angles on the human body, so that the user performs the same motion, the attitude data returned by the attitude sensors may have a relatively big difference.

Figure 15A:
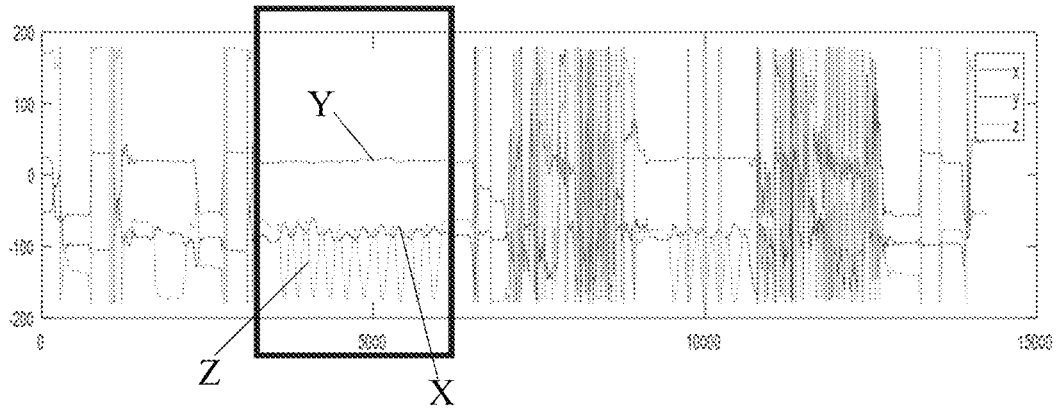
FIG. 15A is an exemplary vector coordinate diagram illustrating Euler angle data in an original coordinate system at a position of a small arm of a human body according to some embodiments of the present disclosure.

FIG. 15A is an exemplary vector coordinate diagram illustrating Euler angle data in an original coordinate system at a position of a small arm of a human body according to some embodiments of the present disclosure. A boxed part may represent the Euler angle data (the coordinate information) in the original coordinate system corresponding to the position of the small arm at the time the user does the same movement. As shown in FIG. 15A, the results of the Euler angle vector in the Z-axis direction (shown as "Z" in FIG. 15A) in the boxed part are approximately in the range of −180° to (−80°). The results of the Euler angle vector in the Y-axis direction (shown as "Y" in FIG. 15A) fluctuate approximately around 0°, and the results of the Euler angle vector in the X-axis direction (shown as "X" in FIG. 15A) fluctuate approximately around −80°. A fluctuation range here may be 20°.

Figure 15B:
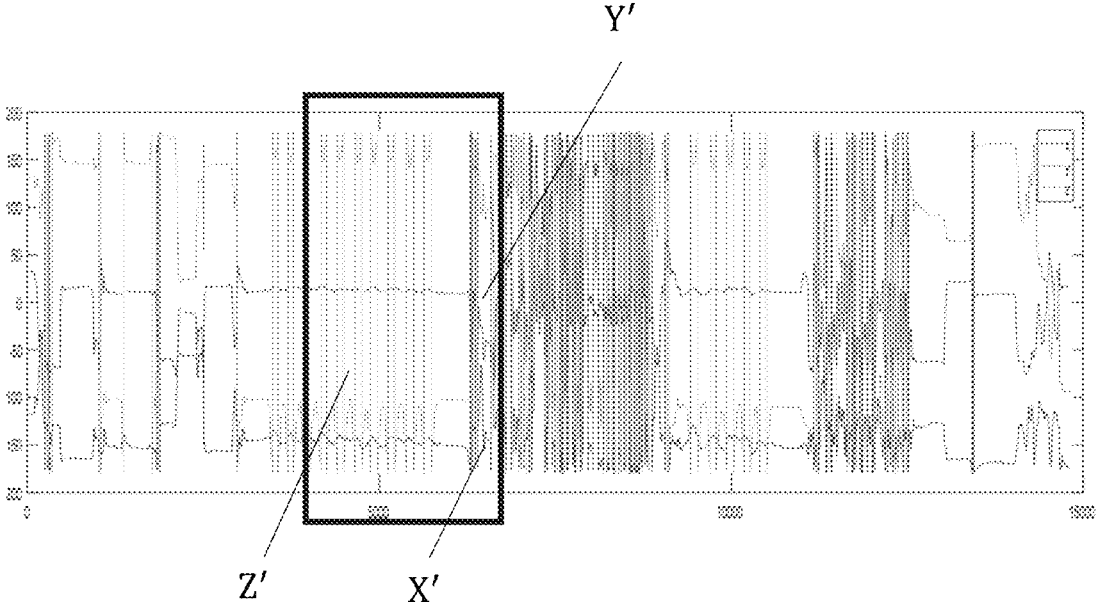
FIG. 15B is an exemplary vector coordinate diagram illustrating Euler angle data in another original coordinate system for a position of a small arm of ae human body according to some embodiments of the present disclosure.

FIG. 15B is an exemplary vector coordinate diagram illustrating Euler angle data in another original coordinate system at a position of a small arm of a human body according to some embodiments of the present disclosure. The boxed part may represent the Euler angle data in the original coordinate system corresponding to the other position of the small arm when the user performs the same movement (the same movement as shown in FIG. 15A). As shown in FIG. 15B, the results of the Euler angle vector in the Z-axis direction (shown as "Z'" in FIG. 15B) in the boxed section are approximately in a range of −180° to 180°. The results of the Euler angle vector in the Y-axis direction (shown as "Y'" in FIG. 15B) fluctuate approximately around 0°. And the results of the Euler angle vector in the X-axis direction (shown as "X'" in FIG. 15B) fluctuate approximately around −150°. The fluctuation range here may be 20°.

The Euler angle data shown in FIG. 15A and FIG. 15B are the Euler angle data (coordinate information) respectively obtained in the original coordinate system when the user performs the same movement at different positions of the human small arm (which can also be interpreted as different installation angles of the attitude sensor at the human small arm position). Comparing FIG. 15A with FIG. 15B, it can be seen that the when the user does the same movement, the angles at which the attitude sensor is installed on the human body are different, causing difference in the Euler angle data in the original coordinate system returned by the attitude sensor. For example, the results of the Euler angle vector in the Z-axis direction in FIG. 15A are approximately in the range of −180°-(−80°), and the results of the Euler angle vector in the Z-axis direction in FIG. 15B are approximately in the range of −180°-180°, which are quite different from each other.

Figure 16A:
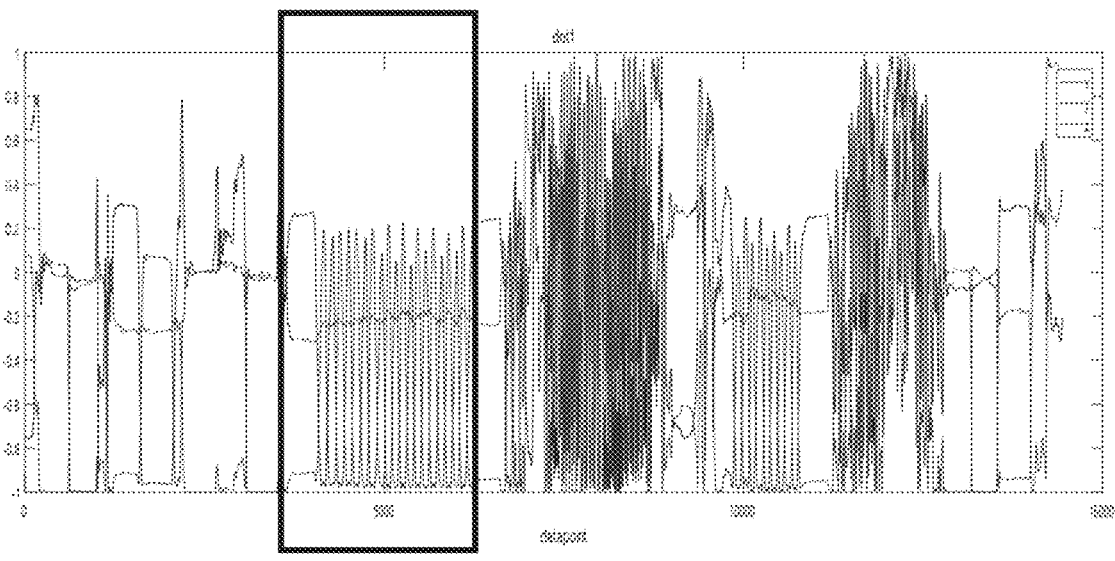
FIG. 16A is an exemplary vector coordinate diagram of Euler angle data in a target coordinate system at a position of a small arm of a human body according to some embodiments of the present disclosure.

In some embodiments, the Euler angle data in the original coordinate system corresponding to sensors with different installation angles may be converted to the Euler angle data in the target coordinate system, thereby facilitating analysis of the attitude signal of the sensors at different positions. Merely as way of exemplary illustration, a line where the left arm is located can be abstracted as a unit vector pointing from the elbow to the wrist, which is a coordinate value in the target coordinate system. The target coordinate system here includes the axis pointing to the rear of the body as the X-axis, the axis pointing to the right side of the body as the Y-axis, and the axis pointing to the top of the body as the Z-axis, which conforms to the right-handed coordinate system. For example, a coordinate value [−1, 0, 0] in the target coordinate system indicates that the arm is held forward flat. A coordinate value [0, −1, 0] of the target coordinate system indicates that the arm is held flat to the left. FIG. 16A is a curve obtained based on the vector coordinates in the target coordinate system converted from the Euler angle data of the small arm in the original coordinates in FIG. 15A. The boxed portion can represent the Euler angle data in the target coordinate system at the position of the small arm when the user performs the movement. As shown in FIG. 16A, a small arm vector [x, y, z] in the boxed portion moves reciprocally between the first position and the second position, where a first position is [0.2, −0.9, −0.38] and the second position is [0.1, −0.95, −0.3]. It should be noted that for each reciprocal movement of the small arm, there will be a small deviation between the first position and the second position.

Figure 16B:
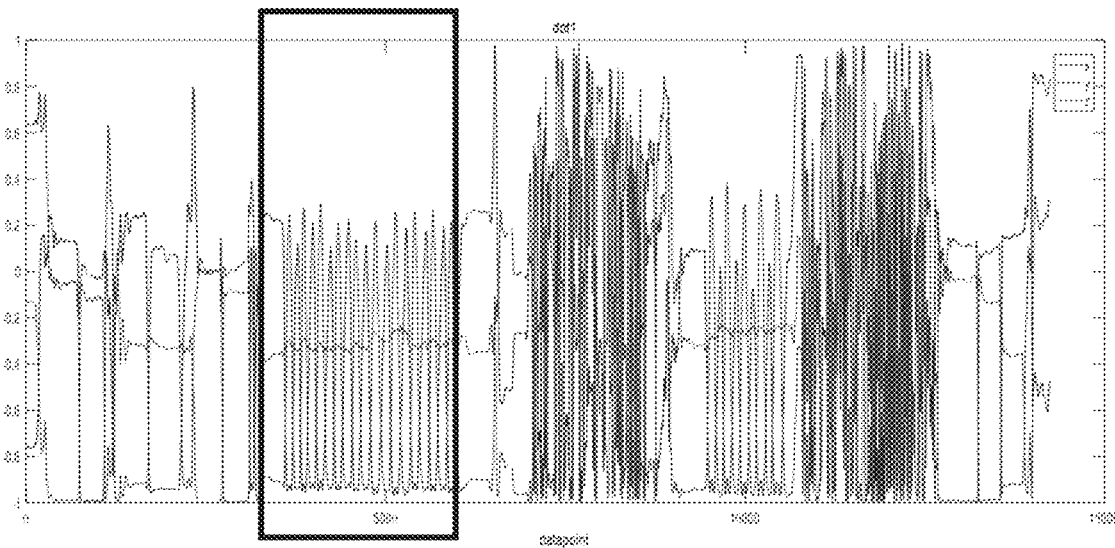
FIG. 16B is an exemplary vector coordinate diagram of Euler angle data in a target coordinate system at another location of a small arm of a human body according to some embodiments of the present disclosure.

FIG. 16B is an exemplary vector coordinate diagram of Euler angle data in a target coordinate system at another location of a small arm of a human body according to some embodiments of the present disclosure. FIG. 16B is a curve obtained based on the vector coordinates in the target coordinate system converted from Euler angle data of the small arm in the original coordinates in FIG. 15B. The boxed part may represent the Euler angle data in the target coordinate system at another location of the small arm when the user performs the same movement (the same movement as the movement shown in FIG. 16A). As shown in FIG. 16B, a small arm vector [x, y, z] similarly reciprocates between the first position and the second position, where a first position is [0.2, −0.9, −0.38] and a second position is [0.1, −0.95, −0.3].

Combining FIG. 15A to FIG. 16B, it can be seen from FIGS. 15A and 15B that the Euler angles in the original coordinate system have a great difference in the range of values and fluctuation forms due to the different installation positions of the two attitude sensors. After converting the coordinate information of the original coordinate system corresponding to the two attitude sensors to the vector coordinates corresponding to the target coordinate system (e.g., the vector coordinates in FIGS. 16A and 16B) respectively, two approximately same vector coordinates may be obtained. That is to say, the method may ensure the feature information corresponding to the attitude signal to be independent of the sensor installation position. Specifically, in FIG. 16A and FIG. 16B, it can be seen that the two attitude sensors are installed in different positions on the small arm, and after the above coordinate conversion, the same vector coordinates are obtained, i.e., during the process of the seated chest press, they can represent the process of switching back and forth between the two states, state 1 (arm held flat to the right) and state 2 (arm held flat to the front).

Figure 17:
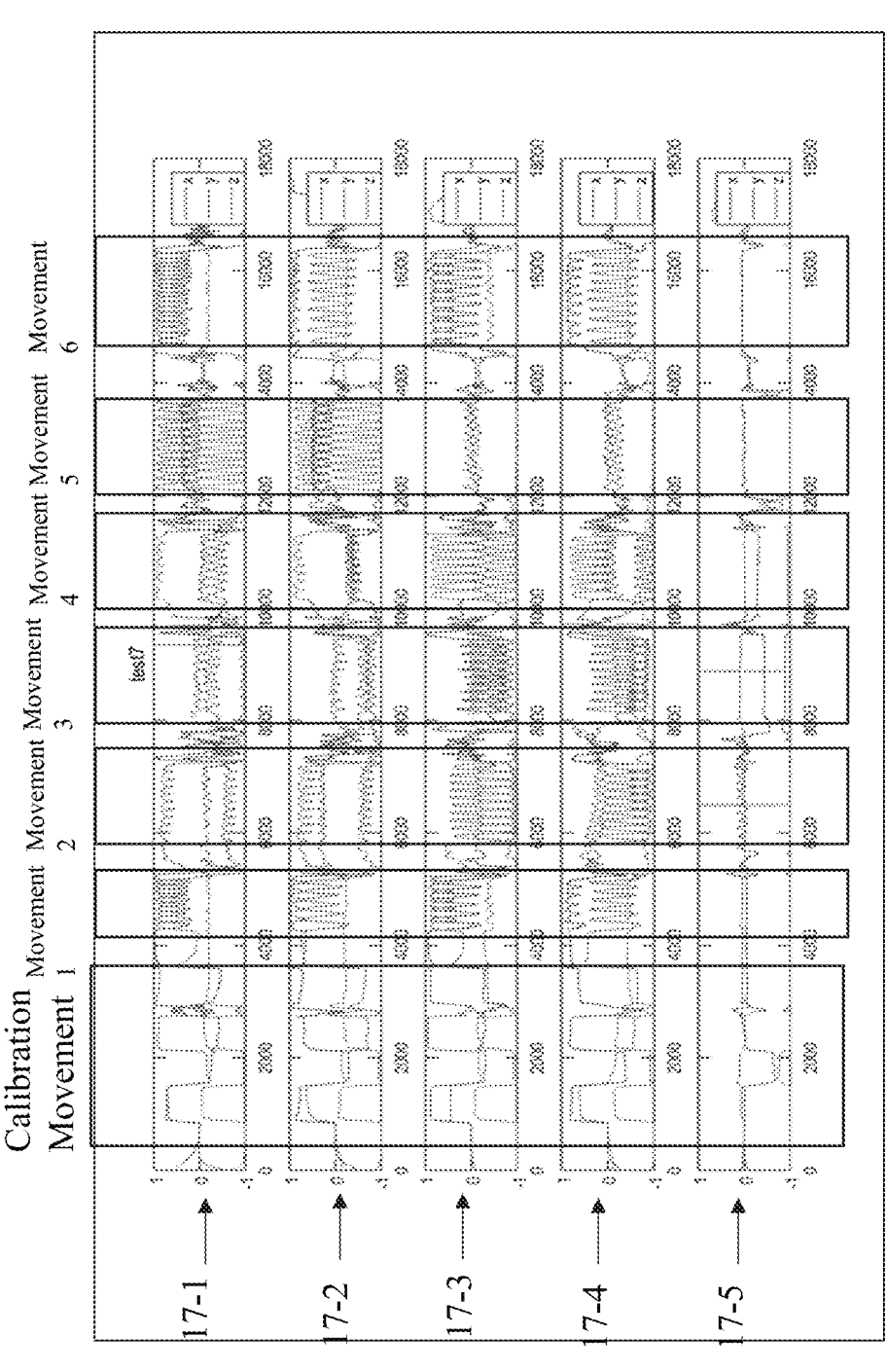
FIG. 17 is an exemplary vector coordinate diagram of Euler angle data in a target coordinate system of a multi-sensor according to some embodiments of the present disclosure.

FIG. 17 is an exemplary vector coordinate diagram of a limb vector in a target coordinate system according to some embodiments of the present disclosure. As shown in FIG. 17, the vector coordinates of the attitude sensors in the target coordinate system at the positions of the left small arm (17-1), right small arm (17-2), left large arm (17-3), right large arm (17-4), and torso (17-5) of the human body can be represented from top to bottom, respectively. The vector coordinates of each position (e.g., 17-1, 17-2, 17-3, 17-4, 17-5) in the target coordinate system of human during motion are illustrated in FIG. 17. The first 4200 points in FIG. 17 correspond to the calibration movements needed to calibrate the limbs, such as standing, torso forward, arm forward, arm side planks, etc. To use the first 4200 points corresponding to the calibration movements to calibrate, raw data collected by the attitude sensors may be converted to the Euler angles in the target coordinate system. To facilitate performing analysis on the data, the coordinate vector of the arm vector in the target coordinate system may be further converted. The target coordinate system here is pointing to the front of the torso as the X-axis, to the left of the torso as the Y-axis, and to the top of the torso as the Z-axis. The reciprocal movements in FIG. 17 are, from left to right, movement 1, movement 2, movement 3, movement 4, movement 5, and movement 6: seated chest press, high pull-down, seated chest thrust, seated shoulder thrust, barbell dip head curl, and seated chest press, respectively. As can be seen in FIG. 17, different movements have different movement patterns, which can be clearly recognized by using the limb vectors. At the same time, the same movement also has good repeatability, for example, the movement 1 and the movement 6 both represent the seated chest press, and the curves of these two movements have the good repeatability.

In some embodiments, the attitude data (e.g., the Euler angles, the angular velocities, etc.) directly output in the original coordinate system may be converted to the attitude data in the target coordinate system by the processes 1300 and 1400, so that highly consistent attitude data (e.g., Euler angles, angular velocities, limb vector coordinates, etc.) can be obtained.

Figures 18A, 18B:
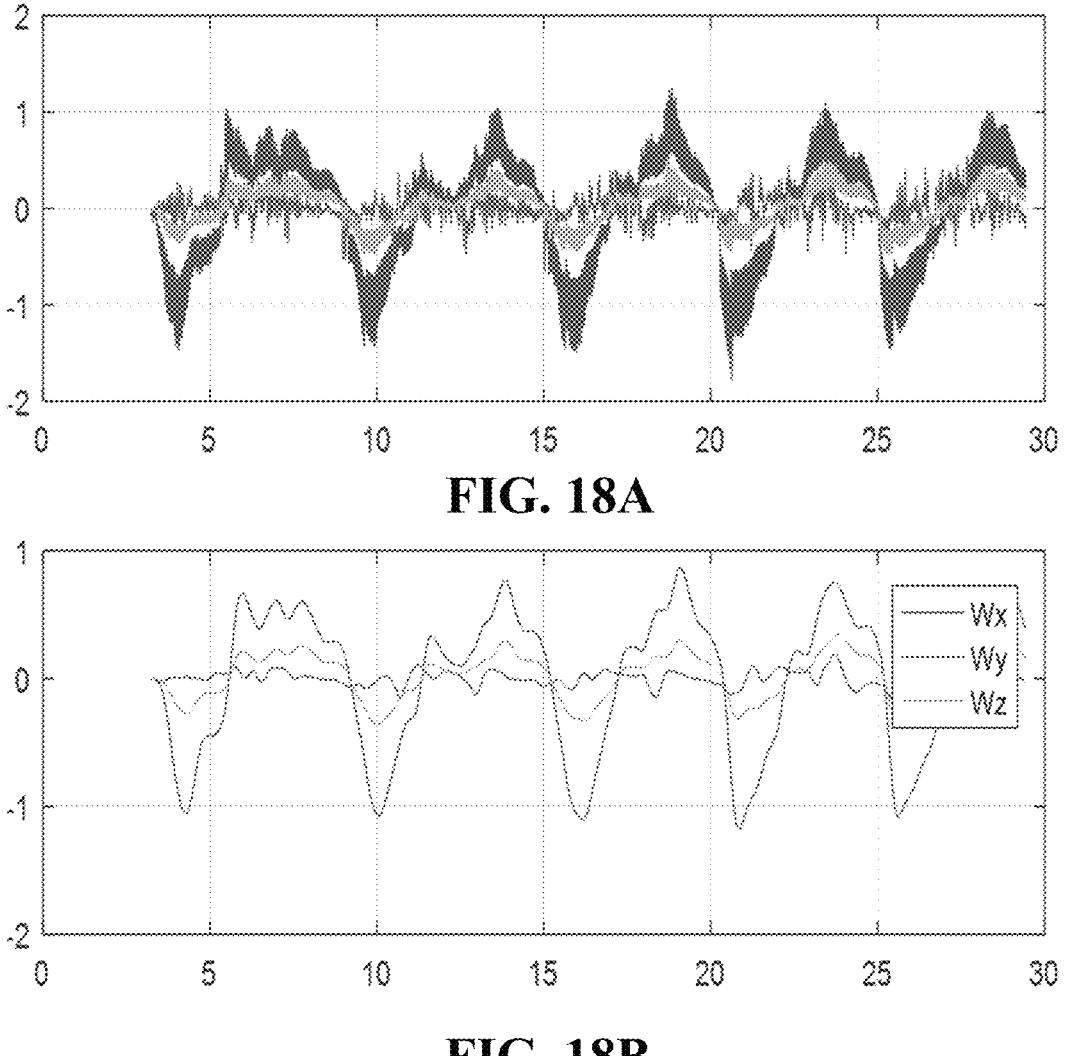
FIG. 18A is a diagram illustrating exemplary results of an original angular velocity according to some embodiments of the present disclosure.
FIG. 18B is a diagram illustrating exemplary results of an angular velocity after filtering processing according to some embodiments of the present disclosure.

FIG. 18A is a diagram illustrating an exemplary coordinate vector of an original angular velocity according to some embodiments of the present disclosure. The original angular velocity may be understood as the conversion of the Euler angle data in the original coordinate systems corresponding to the sensors with different installation angles to the Euler angle data in the target coordinate system. In some embodiments, factors such as jitter during user movement may affect the results of the angular velocity in the attitude data. As shown in FIG. 18A, the original angular velocity shows a more obvious unsmooth curve in its vector coordinate curve under an influence of jitter, etc. For example, a presence of an abrupt signal in the vector coordinate curve of the original angular velocity makes the vector coordinate curve of the original angular velocity unsmooth. In some embodiments, a jittered angular velocity needs to be corrected to obtain a smooth vector coordinate curve because of an effect of jitter, etc. on the angular velocity results. In some embodiments, the original angular velocity may be filtered by using a 1 Hz-3 Hz low-pass filtering method. FIG. 18B is an exemplary diagram illustrating results of an angular velocity after filtering processing according to some embodiments of the present disclosure. As shown in FIG. 18B, performing a low-pass filtering from 1 Hz to 3 Hz on the original angular velocity may eliminate the effect of jitter and other effects on the angular velocity (e.g., abrupt signals), so that the vector coordinate curve corresponding to the angular velocity is displayed smoother. In some embodiments, performing the low-pass filtering from 1 Hz to 3 Hz on the angular velocity may effectively prevent the effects of jitter, etc. on the attitude data (e.g., the Euler angles, the angular velocity, etc.), which makes it easier to follow the process of segmenting the signal. In some embodiments, the filtering process may also filter out an industrial frequency signal and its harmonic wave signal, burr signal, etc. from the movement signal. It should be noted that low-pass filtering at 1 Hz-3 Hz introduces time delay, which makes a movement point of the attitude signal and a movement point of a real electromyographic signal misaligned in time. Therefore, the time delay generated during the low-pass filtering process is subtracted from the vector coordinate curve after the low-pass filtering processing to ensure synchronization of the attitude signal and the electromyographic signal in time. In some embodiments, the time delay is associated with a center frequency of the filter, and when the attitude signal and the electromyographic signal are processed with different filters, and the time delay is adapted according to the center frequency of the filter. In some embodiments, since the angular range of the Euler angle is [−180°, +180° ], an obtained Euler angle may have a change of −180° to +180° or +180° to −180° when an actual Euler angle is not in this angular range. For example, when the angle is −181°, the Euler angle changes to 179°. In the practical application the angle change can affect the calculation of the angle difference, and it is necessary to correct the angle change first.

In some embodiments, a movement recognition model may also be configured to analyze the user's movement signal or the feature information corresponding to the movement signal to recognize the user's movement. In some embodiments, the movement recognition model includes a trained machine learning model configured to recognize the user's movement. In some embodiments, the movement recognition model may include one or more machine learning models. In some embodiments, the movement recognition model may include, but is not limited to, one or more of a machine learning model that classifies the user's movement signal, a machine learning model that recognizes the movement quality of the user, a machine learning model that recognizes the number of the user's movements, and a machine learning model that recognizes a fatigue index of the user performing the movement. In some embodiments, the machine learning model may include one or more of a linear classification model (LR), a support vector machine model (SVM), a plain Bayesian model (NB), a K-nearest neighbor model (KNN), a decision tree model (DT), ae random forest/a gradient boosting decision tree (RF/GDBT, etc.), etc. More descriptions regarding the movement recognition model may be found elsewhere in the present disclosure, such as FIG. 20 and its relevant descriptions.

FIG. 19 is a flowchart illustrating an exemplary motion monitoring and feedback method according to some embodiments of the present disclosure. As shown in FIG. 19, the process 1900 may include:

Step 1910, obtaining the movement signal of the user during motion.

In some embodiments, the step may be performed by the obtaining module 210. In some embodiments, the movement signal includes at least the feature information corresponding to the electromyographic signal and the feature information corresponding to the attitude signal. The movement signal refers to human body parameter information of the user during motion. In some embodiments, the human body parameter information may include, but is not limited to, one or more of the electromyographic signals, the attitude signals, the heart rate signals, the temperature signals, the humidity signals, the blood oxygen concentration, etc. In some embodiments, the movement signal may include at least the electromyographic signal and the attitude signal. In some embodiments, the electromyographic sensor in the obtaining module 210 may collect the electromyographic signal of the user during motion, and the attitude sensor in the obtaining module 210 may collect the attitude signal of the user during motion.

Step 1920, monitoring, based on the movement signal, the user's movement during motion through the movement recognition model, and giving, based on the output of the movement recognition model, the movement feedback.

In some embodiments, the step may be performed by the processing module 220 and/or the processing device 110. In some embodiments, the output of the movement recognition model may include, but is not limited to, one or more of the movement type, the movement quality, the number of movements, a fatigue index, etc. For example, the movement recognition model may recognize the user's movement type as the seated chest press based on the movement signal. For another example, one machine learning model of the movement recognition model may first recognize the user's movement type as the seated chest press based on the movement signal, and another machine learning model of the movement recognition model may output the movement quality of the user's movement as a standard movement or an incorrect movement according to the movement signal (e.g., amplitude information of the electromyographic signal, the frequency information, and/or the angular velocity, the angular velocity direction, and the acceleration value of angular velocity of the attitude signal). In some embodiments, the movement feedback may include sending the prompt message. In some embodiments, the prompt message may include, but is not limited to, the voice prompt, the message prompt, the image prompt, the video prompt, etc. For example, if the output result of the movement recognition model is the incorrect movement, the processing device 110 may control the wearable device 130 or the mobile terminal device 140 to send a voice prompt (e.g., a message such as "nonstandard movement") to the user to remind the user to adjust the fitness movement in a timely manner. For another example, if the output of the movement recognition model is the standard movement, the wearable device 130 or the mobile terminal device 140 may not send a prompt message, or send a prompt message like "standard movement". In some embodiments, the motion feedback may also include the wearable device 130 stimulating the corresponding movement part of the user. For example, the components of the wearable device 130 stimulate the corresponding parts of the user's movements through a vibration feedback, an electrical stimulation feedback, a pressure feedback, etc. For example, the output results of the movement recognition model are the incorrect movement, and the processing device 110 may control the components of the wearable device 130 to stimulate the corresponding parts of the user's movement. In some embodiments, the movement feedback may also include outputting a motion record of the user during motion. The motion record here may refer to one or more of the user's movement type, exercise duration, number of movements, movement quality, fatigue index, physiological parameter information during motion, etc. Descriptions regarding the movement recognition model may be found elsewhere in the present disclosure and will not be repeated herein.

It should be noted that the above description of the process 1900 is for example and illustration purposes only and does not limit the scope of application of the present disclosure. For those skilled in the art, various amendments and changes can be made to process 1900 under the guidance of the present disclosure. However, these amendments and changes remain within the scope of the present disclosure.

Figure 20:
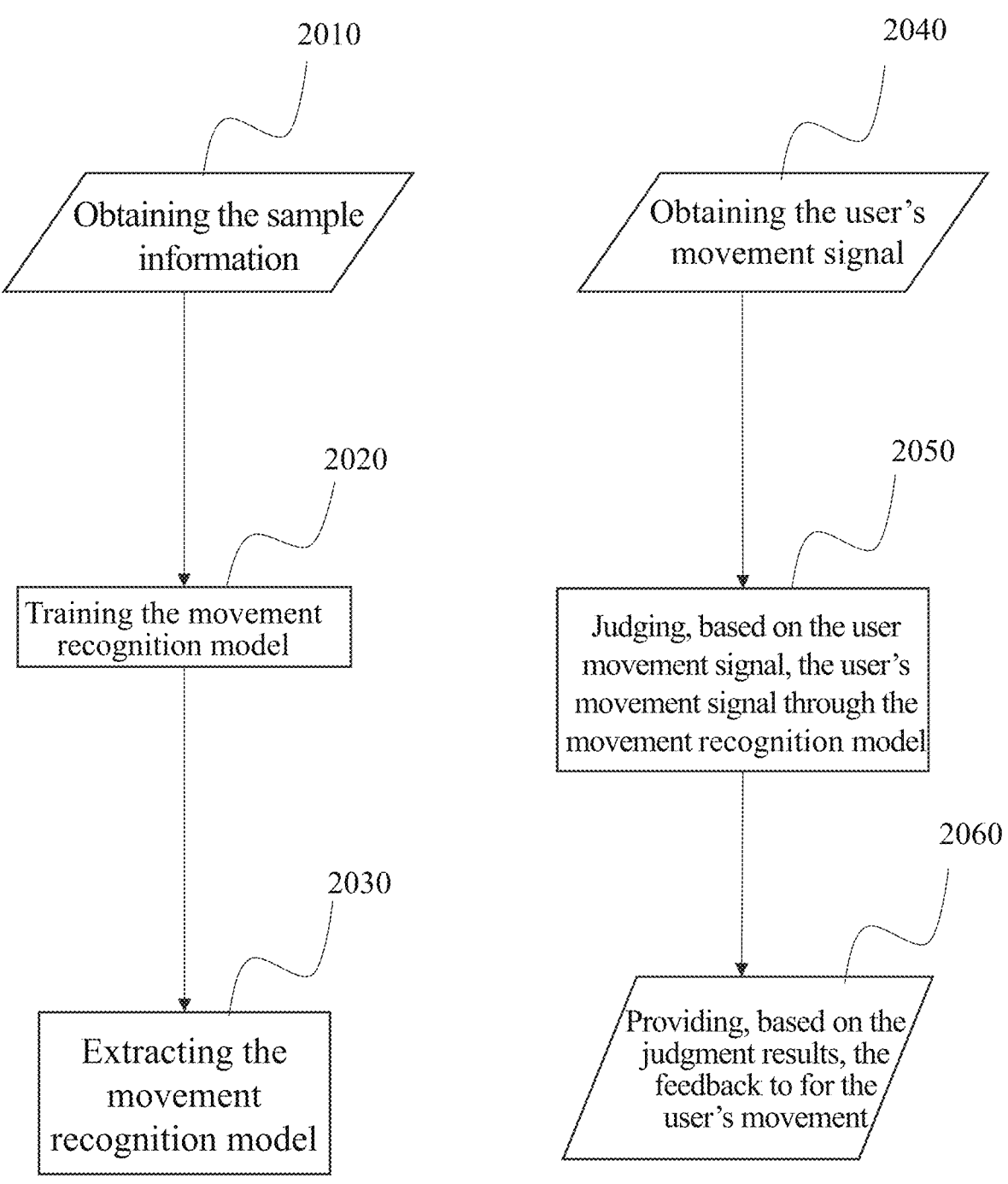
FIG. 20 is a flowchart illustrating exemplary process for model training according to some embodiments of the present disclosure.

FIG. 20 is a flowchart illustrating an exemplary process for model training according to some embodiments of the present disclosure.

In step 2010, obtaining the sample information.

In some embodiments, the step may be performed by the obtaining module 210. In some embodiments, the sample information may include the movement signal of professionals (e.g., fitness trainers) and/or non-professionals during motion. For example, the sample information may include the electromyographic signals and/or the attitude signals generated by the professionals and/or the non-professionals while performing the same movement type (e.g., the seated chest press). In some embodiments, the electromyographic signal and/or attitude signal in the sample information may undergo the segmentation processing of the process 700, the burr processing of the process 900, and the conversion processing of the process 1300, etc., to form at least one segment of the electromyographic signal and/or the attitude signal. The at least one segment of the electromyographic signal and/or the attitude signal may be used as the input of the machine learning model to train the machine learning model. In some embodiments, the feature information corresponding to the at least one segment of the electromyographic signal and/or the feature information corresponding to the attitude signal may also be used as the input of the machine learning model to train the machine learning model. For example, the frequency information and the amplitude information of the electromyographic signal can be used as the input of the machine learning model. For another example, the angular velocity of the attitude signal and the angular velocity direction/the acceleration value of the angular velocity can be used as the input of the machine learning model. For another example, the movement start point, the movement middle point and the movement end point signal can be used as the inputs to the machine learning model. In some embodiments, the sample information may be obtained from the storage device of the processing device 110. In some embodiments, the sample information may be obtained from the obtaining module 210.

In step 2020, training the movement recognition model.

The step may be performed by the processing device 110. In some embodiments, the movement recognition model may include one or more machine learning models. For example, the movement recognition model may include, but is not limited to, one or more of the machine learning model that classifies the user's movement signal, the machine learning model that recognizes the movement quality of the user, the machine learning model that recognizes the number of user's movement, and the machine learning model that recognizes the fatigue level of the user performing the movement. In some embodiments, the machine learning model may include one or more of the linear classification model (LR), the support vector machine model (SVM), the Native Bayesian model (NB), the K-nearest neighbor model (KNN), the decision tree model (DT), the random forest/the gradient boosting decision tree (RF/GDBT, etc.), etc.

In some embodiments, training of the machine learning model may include obtaining the sample information. In some embodiments, the sample information may include the movement signal of the professionals (e.g., fitness trainers) and/or non-professionals during motion. For example, the sample information may include electromyographic signal and/or postural signal generated by professionals and/or the non-professionals while performing the same movement type (e.g., the seated chest press). In some embodiments, the electromyographic signal and/or the attitude signal in the sample information may undergo the segmentation processing of the process 700, the burr processing of the process 900, and the conversion processing of the process 1300, etc., to generate at least one segment of the electromyographic signal and/or the attitude signal. The at least one segment of the electromyographic signal and/or the attitude signal may be used as the input to the machine learning model to train the machine learning model. In some embodiments, the feature information corresponding to the at least one segment of the electromyographic signal and/or the feature information corresponding to the attitude signal may also be used as the input of the machine learning model to train the machine learning model. For example, the frequency information and the amplitude information of the electromyographic signal can be used as the input of the machine learning model. For another example, the angular velocity of the attitude signal and the angular velocity direction/acceleration value of the velocity angle can be used as the input of the machine learning model. For another example, the signal corresponding to the movement start point, the movement middle point, and/or the movement end point signal (including the electromyographic signal and/or the attitude signal) can be used as the input of the machine learning model.

In some embodiments, when training a machine learning model for recognizing the user's movement type, the sample information from the different movement types (per segment of the electromyographic signal or/and the attitude signal) may be labelled and processed. For example, the sample information from the electromyographic signal and/or the attitude signal generated by the user performing a seated chest press may be marked as "1", where "1" is configured to represent the "seated chest press". The sample information from the electromyographic signal and/or the attitude signal generated when the user performs the bicep lifting maybe marked as "2", where "2" is configured to represent the "bicep lifting". The different movement types correspond to the different feature information (e.g., the frequency information, the amplitude information) of electromyographic signals, and feature information (e.g., angular velocity, angular velocity direction, angular velocity value of angular velocity) of attitude signals. Labeled sample information (e.g., feature information corresponding to electromyographic signal and/or attitude signal in the sample information) is used as the input of the machine learning model to train the machine learning model, so that the movement recognition model configured to recognize the user's movement type may be obtained, and by inputting the movement signal in the machine learning model, a corresponding movement type may be output.

In some embodiments, the movement recognition model may further include the machine learning model for determining the quality of the user's movement. The sample information here may include both the standard movement signal (also known as a positive sample) and a non-standard movement signal (also known as negative samples). The standard movement signal may include the movement signal generated by the professional performing the standard movement. For example, the movement signal generated by a professional performing the standard seated chest press is the standard movement signal. The non-standard movement signal may include the movement signal generated by the user performing the non-standard movement (e.g., an incorrect movement). In some embodiments, the electromyographic signal and/or the attitude signal in the sample information may undergo the segmentation processing of the process 700, the burr processing of the process 900, and the conversion processing of the process 1300, etc., to generate at least one segment of the electromyographic signal and/or the attitude signal. The at least one segment of the electromyographic signal and/or the attitude signal may be used as the input of the machine learning model to train the machine learning model. In some embodiments, the positive and negative samples of the sample information (per segment of the electromyographic signal or/the attitude signal) may be tagged. For example, a positive sample is marked as "1" and a negative sample is marked as "0". The "1" here is configured to represent the user's movement as a standard movement, and the "0" here is configured to represent the user's movement as a wrong movement. The trained machine learning model may output different labels based on the input sample information (e.g., the positive sample, the negative sample). It should be noted that the movement recognition model may include one or more machine learning models for analyzing and recognizing the quality of the user movement, and different machine learning models may analyze and recognize the sample information from the different movement types, respectively.

In some embodiments, the movement recognition model may also include a model that recognizes the number of movements of the user's fitness motion. For example, the movement signal (e.g., the electromyographic signal and/or the attitude signal) in the sample information is segmented by the process 700 to obtain at least one set of a movement start point, a movement middle point, and a movement end point, and each set of the movement start point, the movement middle point, and the movement end point is marked, for example, the movement start point is marked as 1, the movement middle point is marked as 2, and the movement end point is marked as 3, and the marks are used as the input to the machine learning model, and a set of consecutive "1", "2" and "3" are input to the machine learning model to output one movement. For example, three consecutive sets of "1", "2", and "3" are input into a machine learning model to output three movements.

In some embodiments, the movement recognition model may also include a machine learning model for identifying a user's fatigue index. The sample information here may also include signals of other physiological parameters such as the electro-cardio signals, the respiratory rates, the temperature signals, the humidity signals, etc. For example, different frequency ranges of the electro-cardio signal can be used as the input data for the machine learning model, with electro-cardio signal in the range of 60 beats/min-100 beats/min marked as "1" (normal) and less than 60 beats/min or more than 100 beats/min marked as "2" (abnormal). In some embodiments, a further segmentation can be performed and different indices can be labeled as the input data based on the user's electro-cardio signal frequency, and the trained machine learning model can output a corresponding fatigue index according to the frequency of the electro-cardio signal. In some embodiments, the machine learning model may also be trained in conjunction with the physiological parameter signal such as the respiratory rate and the temperature signal. In some embodiments, the sample information may be obtained from the storage device of processing device 110. In some embodiments, the sample information may be obtained from the obtaining module 210. It should be noted that the movement recognition model can be any one of the above machine learning models or a combination of a plurality of above machine learning models, or include other machine learning models, which can be selected according to the actual situation. In addition, a training input to the machine learning model is not limited to one segment (one cycle) of the movement signal, but can also be part of a segment of the movement signal, or a plurality of segments of the movement signal, etc.

Step 2030, extracting the movement recognition model.

In some embodiments, the step may be performed by the processing device 110. In some embodiments, the processing device 110 and/or the processing module 220 may extract the movement recognition model. In some embodiments, the movement recognition model may be stored to the processing device 110, the processing module 220, or the mobile terminal.

Step 2040, obtaining the user's movement signal.

In some embodiments, the step may be performed by the obtaining module 210. For example, in some embodiments, the electromyographic sensor in the obtaining module 210 may obtain the electromyographic signal of the user, and the attitude sensor in the obtaining module 210 may obtain the attitude signal of the user. In some embodiments, the user movement signal may also include other physiological parameter signals such as the electro-cardio signal, the respiration signal, the temperature signal, the humidity signal, etc. of the user during motion. In some embodiments, the obtained movement signal (e.g., the electromyographic signal and/or the attitude signal) may be subjected to the segmentation processing of the process 700, the burr processing of process the 900, and the conversion processing of the process 1300, etc., to form at least one segment of the electromyographic signal and/or the attitude signal.

Step 2050, judging, based on the user's movement signal, the movement through the movement recognition model.

The step may be performed by the processing device 110 and/or the processing module 220. In some embodiments, the processing device 110 and/or the processing module 220 may determine the user movement based on the movement recognition model. In some embodiments, the trained movement recognition model may include one or more machine learning models. In some embodiments, the movement recognition model may include, but is not limited to, one or more of the machine learning model that classifies the user's movement signal, the machine learning model that recognizes the movement of the user, the machine learning model that recognizes the number of user's movement, and the machine learning model that recognizes the fatigue index of the user performing the movements. The different machine learning models may have different recognition effects. For example, a machine learning model for classifying the movement signal may use the user's movement signal as input data and output the corresponding movement type. For example, a machine learning model that recognizes the quality of the user's movement can use the user's movement signal as input data and output the movement quality (e.g., standard movement, wrong movement). For example, the machine learning model that recognizes the fatigue index of a user performing a movement can use the user's movement signal (e.g., the electro-cardio signal frequency) as the input data and output the user's fatigue index. In some embodiments, the user's movement signal and the judgment results (output) of the machine learning model may also be used as the sample information of training the movement recognition model to optimize relevant parameters of the movement recognition model. It should be noted that the movement recognition model is not limited to the trained machine learning model described above, but can also be a preset model, e.g., a manually predefined conditional judgment algorithm or add an artificially added parameter (e.g., confidence level) to the trained machine learning model, etc.

Step 2060, providing, based on the judgment results, feedback for the user's movement.

In some embodiments, the step may be performed by the wearable device 130 and/or the mobile terminal device 140. Further, the processing device 110 and/or the processing module 220 sends a feedback instruction to the wearable device 130 and/or the mobile terminal device 140 based on the judgment results of the user's movement, and the wearable device 130 and/or the mobile terminal device 140 provides the feedback to the user based on the feedback instruction. In some embodiments, the feedback may include sending prompt messages (e.g., text information, picture information, video information, voice information, indicator information, etc.) and/or stimulating the user's body when performing the movement (in a form of electrical stimulation, vibration, pressure changes, heat change, etc.). For example, when a user performs a sit-up movement, the user's movement signal is monitored and it is determined that the user is exerting too much force on the oblique muscles during motion (i.e., a user's head and neck movement are not standard), in which case the input/output module 260 (e.g., a vibration prompter) in the wearable device 130 and the mobile terminal device 140 (e.g., a smartwatch, smartphone etc.) provide a corresponding feedback (e.g., perform the vibration on the user's body part, send the voice prompt, etc.) to prompt the user to adjust the force-exerting part of body in time. In some embodiments, during the user's movement, by monitoring the movement signal during the user's movement and determining the movement type, the movement quality, and the number of the user's movements during motion, the mobile terminal device 140 can output the corresponding movement record so that the user can understand its motion situation during motion.

In some embodiments, when the feedback is given to the user, the feedback may be matched to user perception. For example, if the user's movement is not standard, the user can know that the movement is not standard based on the vibration stimulation in the area corresponding to the user's movement, and the vibration stimulation is in an acceptable range of the user. Further, a matching model may be constructed based on user's movement signal and the user perception to find the best balance between the user perception and a real feedback.

In some embodiments, the movement recognition model may further be trained based on the user's movement signals. In some embodiments, training the movement recognition model according to the user's movement signal may include evaluating the user's movement signal to determine a confidence level of the user's movement signal. The confidence level may indicate the quality of the user's movement signal. For example, the higher the confidence level, the better the quality of the user's movement signal. In some embodiments, evaluation of the user's movement signal may be performed at the stages of the movement signal obtaining, pre-processing, segmentation, and/or recognition.

In some embodiments, training the movement recognition model according to the user's movement signal may further include determining whether the confidence level is greater than a confidence level threshold (e.g., 80), and if the confidence level is greater than or equal to the confidence level threshold, the movement recognition model is trained by using the user's movement signal corresponding to that confidence level as sample data. If the confidence level is less than the confidence level threshold, the user's movement signal corresponding to the confidence level is not used as sample data to train the movement recognition model. In some embodiments, the confidence level may include, but is not limited to, a confidence level at any of the stages of the movement signal obtaining, the movement signal pre-processing, movement signal segmentation, or the movement signal recognition. For example, the confidence level of the movement signal collected by the obtaining module 210 is used as a judgment criterion. In some embodiments, the confidence level may further be a combined confidence level at any of the above stages. The combined confidence level may be obtained by averaging or weighting the confidence levels of the stages, etc. In some embodiments, the movement recognition model according to the user's movement signal may be trained in real time, periodically (e.g., a day, a week, a month, etc.), or when a certain data size is met.

It should be noted that the above description of the process 1700 is merely provided for the purpose of illustration, and is not intended to limit the scope of the present disclosure. For those skilled in the art, various of amendments and changes may be made to the process 1700 under the guidance of the present disclosure. However, these amendments and changes remain within the scope of this disclosure.

The basic concepts have been described. Obviously, for those skilled in the art, the detailed disclosure may be only an example and does not constitute a limitation to the present disclosure. Although not explicitly stated here, those skilled in the art may make various modifications, improvements, and amendments to the present disclosure. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various parts of the present disclosure are not necessarily all referring to the same embodiment. In addition, some features, structures, or features in the present disclosure of one or more embodiments may be appropriately combined.

In addition, those skilled in the art can understand that various aspects of the present disclosure can be illustrated and described through several patentable categories or situations, including any new and useful processes, machines, products, or combinations of materials, or any new and useful improvements. Accordingly, all aspects of the present disclosure may be performed entirely by hardware, may be performed entirely by software (including firmware, resident software, microcode, etc.), or may be performed by a combination of hardware and software. The above hardware or software can be referred to as "data block", "module", "engine", "unit", "component" or "system". In addition, aspects of the present disclosure may appear as a computer product located in one or more computer-readable media, the product including computer-readable program code.

The computer storage medium may include a propagation data signal containing a computer program encoding, such as on a baseband or as part of a carrier. The propagation signal may have a variety of expressions, including electromagnetic form, optical form, or suitable combination form. The computer storage medium can be any computer-readable medium other than the computer-readable storage medium, which can be used to perform systems, devices, or devices to implement communication, propagating, or devices by connecting to an instruction. The program code located on the computer storage medium may be propagated through any suitable medium, including radio, cable, fiber optic cable, RF, or similar media, or any combination of the foregoing.

Computer program code for carrying out operations for aspects of the present disclosure may be written in any combination of one or more programming languages, including an object-oriented programming language such as Java, Scala, Smalltalk, Eiffel, JADE, Emerald, C++, C #, VB.NET, Python or the like, conventional procedural programming languages, such as the "C" programming language, Visual Basic, Fortran 2003, Perl, COBOL 2002, PHP, ABAP, dynamic programming languages such as Python, Ruby, and Groovy, or other programming languages. The program code may execute entirely on the user's computer, partly on the user's computer, as a stand-alone software package, partly on the user's computer, partly on a remote computer, or entirely on the remote computer or server. In the case of subsequent cases, the remote computer can be connected to the user computer through any network, such as a local area network (LAN) or a wide area network (WAN), or connected to an external computer (e.g., through the Internet), or in the cloud computing environment, or as a service Use Software, SaaS.

Moreover, unless otherwise specified in the claims, the sequence of the processing elements and sequences of the present disclosure, the use of digital letters, or other names are not used to define the order of the application flow and methods. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure and aiding in the understanding of one or more of the various embodiments. However, this disclosure does not mean that the present disclosure object requires more features than the features mentioned in the claims. Rather, claimed subject matter may lie in less than all features of a single foregoing disclosed embodiment.

In some embodiments, numbers expressing quantities of ingredients, properties, and so forth, configured to describe and claim certain embodiments of the application are to be understood as being modified in some instances by the term "about," "approximate," or "substantially". Unless otherwise stated, "approximately", "approximately" or "substantially" indicates that the number is allowed to vary by ±20%. Correspondingly, in some embodiments, the value parameters used in the present disclosure and claims are approximate values. The approximate values may be changed according to the characteristics of individual embodiments. In some embodiments, the numerical parameters should be construed in light of the number of reported significant digits and by applying ordinary rounding techniques. Although the numerical domains and parameters used in the present application are used to confirm the range of ranges, the settings of this type are as accurate in the feasible range within the feasible range in the specific embodiments.

For each patent, patent application, patent application publication, and other materials cited in the present disclosure, such as articles, books, specifications, publications, documents, etc., the entire contents are hereby incorporated by reference into the present disclosure. Except for application history documents that are inconsistent with or conflict with the contents of the present disclosure, the documents with the most limited scope of the claims of the present disclosure (current or later appended to the present disclosure) are also excluded. It should be noted that if the description, definition, and/or terms used in the appended application of the present disclosure are inconsistent or conflicting with the content described in the present disclosure, the use of the description, definition, and/or terms of the present disclosure shall prevail.

At last, it should be understood that the embodiments described in the present disclosure are merely illustrative of the principles of the embodiments of the present disclosure. Other modifications that may be employed may be within the scope of the present disclosure. Thus, by way of example, but not of limitation, alternative configurations of the embodiments of the present disclosure may be utilized in accordance with the teachings herein. Accordingly, the embodiments of the present disclosure are not limited to that precisely as shown and described.

What is claimed is:

1. A motion monitoring method, comprising:
obtaining a movement signal of a user during motion, the movement signal comprising at least an electromyographic signal and an attitude signal; and
segmenting, based on feature information corresponding to the electromyographic signal and feature information corresponding to the attitude signal, the movement signal, wherein the feature information corresponding to the electromyographic signal includes at least frequency information or amplitude information, and the feature information corresponding to the attitude signal includes at least one of an angular velocity direction, an angular velocity value, an acceleration of an angular velocity, an angle, displacement information, and stress;
determining, based on at least one segment of the movement signal through a movement recognition model, movement-related information, wherein the movement recognition model is a trained machine learning model, the movement-related information includes movement quality and the movement quality includes a standard movement or a wrong movement; and
in responding to determining that the movement quality is the wrong movement, controlling an electromyography sensor to generate an electrical stimulation signal to prompt the user to make a motion adjustment.

2. The motion monitoring method of claim 1, wherein the segmenting, based on the feature information corresponding to the electromyographic signal and the feature information corresponding to the attitude signal, the movement signal includes:
segmenting the attitude signal the feature information corresponding to the attitude signal according to operations including:
determining, based on a time domain window of the attitude signal, at least one target feature point from the time domain window according to a preset condition, wherein the at least one target feature point includes one of a movement start point, a movement middle point, and a movement end point; and
segmenting, based on the at least one target feature point, the attitude signal.

3. The motion monitoring method of claim 2, wherein the preset condition includes one or more of a change in the angular velocity direction corresponding to the attitude signal; the angular velocity corresponding to the attitude signal being greater than or equal to an angular velocity threshold; a changed value of the angular velocity value corresponding to the attitude signal being an extreme value; and the angle corresponding to the attitude signal reaching an angular threshold;

wherein the preset condition further includes the acceleration of the angular velocity corresponding to the attitude signal being continuously greater than or equal to an acceleration threshold of the angular velocity for a first specific time range.

4. The motion monitoring method of claim 1, wherein segmenting, based on the feature information corresponding to the electromyographic signal and the feature information corresponding to the attitude signal, the movement signal includes:

segmenting the electromyographic signal based on the feature information corresponding to the electromyographic signal according to operations including:

pre-processing the electromyographic signal in a frequency domain or a time domain;

obtaining, based on the pre-processed electromyographic signal, the feature information corresponding to the electromyographic signal; and segmenting the electromyographic signal based on the feature information corresponding to the electromyographic signal.

5. The motion monitoring method of claim 4, wherein the pre-processing the electromyographic signal in a frequency domain or a time domain includes:

filtering the electromyographic signal to select components of the electromyographic signal in a specific frequency range in the frequency domain.

6. The motion monitoring method of claim 4, wherein the pre-processing the electromyographic signal in a frequency domain or a time domain includes:

performing a signal correction processing on the electromyographic signal in the time domain.

7. The motion monitoring method of claim 6, wherein the performing a signal correction processing on the electromyographic signal in the time domain includes:

determining a singularity in the electromyographic signal, wherein the singularity corresponds to an abrupt signal of the electromyographic signal; and performing the signal correction processing on the singularity in the electromyographic signal;

wherein the performing the signal correction processing on the singularity in the electromyographic signal includes:

removing the singularity, or correcting the singularity according to a signal around the singularity.

8. The motion monitoring method of claim 7, wherein the singularity includes a burr signal, the determining the singularity in the electromyographic signal includes:

selecting, based on the time domain window of the electromyographic signal, different time windows from the time domain window of the electromyographic signal, wherein the different time windows respectively cover different time ranges; and determining, based on the feature information corresponding to the electromyographic signal in the different time windows, the burr signal.

9. The motion monitoring method of claim 8, wherein the determining, based on the feature information corresponding to the electromyographic signal in the different time windows, the burr signal, includes:

determining first amplitude information corresponding to the electromyographic signal within a first time window and second amplitude information corresponding to the electromyographic signal within a second time window, wherein the first time window and the second time window are two adjacent time windows;

determining whether a ratio of the second amplitude information to the first amplitude information is greater than a threshold:

in response to determining that the ratio of the second amplitude information to the first amplitude information is greater than the threshold, performing a signal correction processing on the electromyographic signal within the second time window;

in response to determining that the ratio of the second amplitude information to the first amplitude information is not greater than the threshold, retaining the electromyographic signal within the second time window.

10. The motion monitoring method of claim 1, further comprising determining, based on the attitude signal, the feature information corresponding to the attitude signal, wherein the attitude signal comprises coordinate information in at least one original coordinate system; and determining, based on the attitude signal, the feature information corresponding to the attitude signal comprises:

obtaining a target coordinate system and a conversion relationship between the target coordinate system and the at least one original coordinate system;

converting, based on the conversion relationship, the coordinate information in the at least one original coordinate system to coordinate information in the target coordinate system; and determining, based on the coordinate information in the target coordinate system, the feature information corresponding to the attitude signal;

wherein the target coordinate system changes as an orientation of the user changes.

11. The motion monitoring method of claim 10, wherein the attitude signal includes coordinate information generated by at least two sensors, the at least two sensors are located at different motion parts of the user and correspond to different original coordinate systems, the determining, based on the attitude signal, the feature information corresponding to the attitude signal includes:

determining feature information corresponding to each of the at least two sensors based on the conversion relationship between different original coordinate systems and the target coordinate system; and determining, based on the feature information respectively corresponding to the at least two sensors, a relative motion between the motion parts of the user.

12. The motion monitoring method of claim 10, wherein the conversion relationship between the at least one original coordinate system and the target coordinate system is obtained by a calibration process including:

constructing a specific coordinate system, the specific coordinate system being related to an orientation of the user during the calibration process;

obtaining first coordinate information of the at least one original coordinate system when the user is in a first pose;

obtaining second coordinate information of the at least one original coordinate system when the user is in a second pose; and determining the conversion relationship between the at least one original coordinate system and the specific coordinate system according to the first coordinate information, the second coordinate information, and the specific coordinate system;

wherein the calibration process further includes:

obtaining a conversion relationship between the specific coordinate system and the target coordinate system; and determining, according to the conversion relationship between the at least one original coordinate system and the specific coordinate system and the conversion relationship between the specific coordinate system and the target coordinate system, the conversion relationship between the at least one original coordinate system and the target coordinate system.

13. The motion monitoring method of claim 10, wherein the attitude signal includes coordinate information generated by at least two sensors, the at least two sensors are located at different locations of a same motion part of the user and correspond to different original coordinate systems, the determining, based on the coordinate information in the target coordinate system, the feature information corresponding to the attitude signal includes:

determining, based on the coordinate information in original coordinate systems corresponding to multiple sensors of different types by Kalman filtering, the coordinate information in the target coordinate system.

14. The motion monitoring method of claim 1, wherein the movement signal further comprising: an electro-cardio signal, a temperature signal, a humidity signal, a blood oxygen concentration, and a respiration rate; and the movement recognition model includes one or more of a machine learning model that classifies the movement signal of the user, a machine learning model that recognizes the movement quality of the user, a machine learning model that recognizes a number of movements of the user, and a machine learning model that recognizes a fatigue level of the user performing the movement.

15. The motion monitoring method of claim 1, wherein a training of the motion recognition model comprising:

determining a confidence level of the movement signal by evaluating the movement signal, and in response to determining the confidence level being greater than or equal to a confidence level threshold, training the motion recognition model in real time by using the motion signal as sample data.

16. The motion monitoring method of claim 1, wherein the segmenting, based on feature information corresponding to the electromyographic signal and feature information corresponding to the attitude signal, comprises:

pre-processing the electromyographic signal in a frequency domain or a time domain, according to operations including:

determining a singularity in the electromyographic signal, wherein the singularity corresponds to an abrupt signal of the electromyographic signal; and performing the signal correction processing on the singularity in the electromyographic signal;

wherein the performing the signal correction processing on the singularity in the electromyographic signal includes removing the singularity or performing the signal correction processing on the singularity according to a signal around the singularity includes:

correcting the singularity according to a signal around the singularity;

obtaining, based on the pre-processed electromyographic signal, the feature information corresponding to the electromyographic signal; and segmenting, based on feature information corresponding to the electromyographic signal and feature information corresponding to the attitude signal, the movement signal.

17. The motion monitoring method of claim 16, wherein the singularity includes a burr signal, the determining the singularity in the electromyographic signal includes:

selecting, based on the time domain window of the electromyographic signal, different time windows from the time domain window of the electromyographic signal, wherein the different time windows respectively cover different time ranges; and determining, based on the feature information corresponding to the electromyographic signal in the different time windows, the burr signal;

wherein the determining, based on the feature information corresponding to the electromyographic signal in the different time windows, the burr signal, includes:

determining first amplitude information corresponding to the electromyographic signal within a first time window and second amplitude information corresponding to the electromyographic signal within a second time window, wherein the first time window and the second time window are two adjacent time windows;

determining whether a ratio of the second amplitude information to the first amplitude information is greater than a threshold:

in response to determining that the ratio of the second amplitude information to the first amplitude information is greater than the threshold, performing a signal correction processing on the electromyographic signal within the second time window;

in response to determining that the ratio of the second amplitude information to the first amplitude information is not greater than the threshold, retaining the electromyographic signal within the second time window.

18. The motion monitoring method of claim 17, further comprising determining, based on the attitude signal, the feature information corresponding to the attitude signal, wherein the attitude signal comprises coordinate information in at least one original coordinate system; and determining, based on the attitude signal, the feature information corresponding to the attitude signal comprises:

obtaining a target coordinate system and a conversion relationship between the target coordinate system and the at least one original coordinate system;

converting, based on the conversion relationship, the coordinate information in the at least one original coordinate system to coordinate information in the target coordinate system; and determining, based on the coordinate information in the target coordinate system, the feature information corresponding to the attitude signal;

wherein the target coordinate system changes as an orientation of the user changes;

the attitude signal includes coordinate information generated by at least two sensors, the at least two sensors are located at different motion parts of the user and correspond to different original coordinate systems, the determining, based on the attitude signal, the feature information corresponding to the attitude signal includes:

determining feature information corresponding to each of the at least two sensors based on the conversion relationship between different original coordinate systems and the target coordinate system; and determining, based on the feature information respectively corresponding to the at least two sensors, a relative motion between the motion parts of the user.

19. The motion monitoring method of claim 18, wherein the conversion relationship between the at least one original coordinate system and the target coordinate system is obtained by a calibration process including:

constructing a specific coordinate system, the specific coordinate system being related to an orientation of the user during the calibration process;

obtaining first coordinate information of the at least one original coordinate system when the user is in a first pose;

obtaining second coordinate information of the at least one original coordinate system when the user is in a second pose; and determining the conversion relationship between the at least one original coordinate system and the specific coordinate system according to the first coordinate information, the second coordinate information, and the specific coordinate system;

wherein the calibration process further includes:

obtaining a conversion relationship between the specific coordinate system and the target coordinate system; and determining, according to the conversion relationship between the at least one original coordinate system and the specific coordinate system and the conversion relationship between the specific coordinate system and target coordinate system, the conversion relationship between the at least one original coordinate system and the target coordinate system.

20. A motion monitoring and feedback method, comprising:

obtaining movement signal of a user during motion, wherein the movement signal includes an electromyographic signal and an attitude signal;

segmenting, based on feature information corresponding to the electromyographic signal, the electromyographic signal to obtain electromyographic signal segments;

segmenting, based on feature information corresponding to the attitude signal, the attitude signal to obtain attitude signal segments, comprising:

determining, based on a time domain window of the attitude signal, at least one target feature point from the time domain window according to a preset condition, wherein the preset condition includes one or more of a change in an angular velocity direction corresponding to the attitude signal; an angular velocity corresponding to the attitude signal being greater than or equal to an angular velocity threshold; a changed value of an angular velocity value corresponding to the attitude signal being an extreme value; and an angle corresponding to the attitude signal reaching an angular threshold; and segmenting, based on the at least one target feature point, the attitude signal;

determining, based on the electromyographic signal segments and the attitude signal segment through a movement recognition model, a movement quality, wherein the movement quality includes a standard movement or a wrong movement, the movement recognition model is a trained machine learning model, a training of the motion recognition model comprising:

determining a confidence level of the movement signal by evaluating the movement signal, and in response to determining the confidence level being greater than or equal to a confidence level threshold, training the motion recognition model in real time by using the motion signal as sample data;

in response to determining the movement quality being the wrong movement, controlling a electromyography sensor to generate an electrical stimulation signal to prompt the user to make a motion adjustment.

* * * * *